United States Patent
Fischer et al.

(10) Patent No.: US 8,168,566 B2
(45) Date of Patent: May 1, 2012

(54) 4-BIPHENYL-SUBSTITUTED PYRAZOLIDIN-3,5-DIONE DERIVATIVES

(75) Inventors: Reiner Fischer, Monheim (DE);
Thomas Bretschneider, Lohmar (DE);
Ernst Rudolf F. Gesing,
Erkrath-Hochdahl (DE); Dieter Feucht,
Eschborn (DE); Karl-Heinz Kuck,
Langenfeld (DE); Peter Lösel,
Leverkusen (DE); Olga Malsam,
Rösrath (DE); Christian Arnold,
Langenfeld (DE); Thomas Auler,
Leichlingen (DE); Martin Jeffrey Hills,
Idstein (DE); Heinz Kehne, Hofheim
(DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/017,194

(22) Filed: Jan. 31, 2011

(65) Prior Publication Data

US 2012/0040963 A1 Feb. 16, 2012

Related U.S. Application Data

(62) Division of application No. 10/567,788, filed as application No. PCT/EP2004/008638 on Aug. 2, 2004, now Pat. No. 8,119,566.

(30) Foreign Application Priority Data

Aug. 14, 2003 (DE) .................................. 103 37 497

(51) Int. Cl.
*A01N 43/72* (2006.01)
*A01N 43/58* (2006.01)
*A01N 43/56* (2006.01)
*A01P 13/00* (2006.01)

(52) U.S. Cl. ........ 504/218; 504/236; 504/281; 514/248; 514/211.08; 514/403

(58) Field of Classification Search .................. None
See application file for complete search history.

(56) References Cited

U.S. PATENT DOCUMENTS 7,569,517 B2 * 8/2009 Fischer et al. ................ 504/218

FOREIGN PATENT DOCUMENTS

WO  WO 0117973 A2 * 3/2001

* cited by examiner

*Primary Examiner* — Yong Chu
(74) *Attorney, Agent, or Firm* — Sterne, Kessler, Goldstein & Fox PLLC

(57) ABSTRACT

The present invention relates to novel 4-biphenyl-substituted pyrazolidine-3,5-dione derivatives of the formula (I)

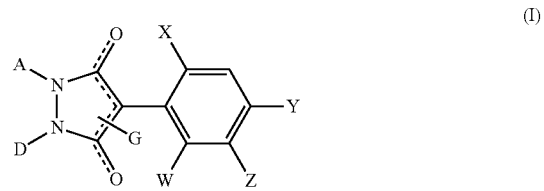

(I)

in which
A, D, G, W, X, Y and Z are as defined above,
to a plurality of processes for the preparation and to their use as pesticides and/or herbicides and/or microbicides.
Moreover, the invention relates to selective herbicidal compositions comprising both the 4-biphenyl-substituted pyrazolidine-3,5-dione derivatives of the formula (I) and a crop plant compatibility-improving compound.

5 Claims, No Drawings

4-BIPHENYL-SUBSTITUTED PYRAZOLIDIN-3,5-DIONE DERIVATIVES

The present invention relates to novel 4-biphenyl-substituted pyrazolidine-3,5-dione derivatives, to a plurality of processes for their preparation and to their use as pesticides and/or herbicides and/or microbicides. Moreover, the invention relates to novel selective herbicidal active compound combinations comprising both the 4-biphenyl-substituted pyrazolidine-3,5-dione derivatives and at least one crop plant compatibility-improving compound, which combinations can be used with particularly good results for the selective control of weeds in various crops of useful plants.

4-Arylpyrazolidine-3,5-dione derivatives having herbicidal, acaricidal and insecticidal properties are described in EP-A-508 126, WO 92/16 150, WO 96/721 652, WO 99/43 649, WO 99/47 525, WO 99/48 869, WO 99/55 673, WO 01/17 351, WO 01/17 352, WO 01/17 353, WO 01/17 972, WO 01/17 973, WO 03/062 244, WO 03/028 446. Also known are 4-arylpyrazolidines, which have been described to have fungicidal properties (WO 96/36 229, WO 96/36 615, WO 96/36 616, WO 96/36 633).

However, in particular at low application rates and concentrations, the activity and the activity spectrum of these compounds are not always entirely satisfactory. Furthermore, the plant compatibility of these compounds is not always sufficient.

This invention provides novel compounds of the formula (I)

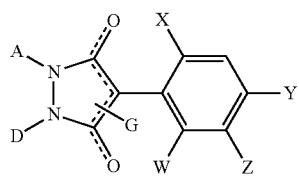

in which

X represents halogen, alkyl, alkoxy, alkenyloxy, alkylthio, alkylsulphinyl, alkylsulphonyl, haloalkyl, haloalkoxy, haloalkenyloxy, nitro, cyano, Z represents in each case optionally substituted aryl or hetaryl, W and Y independently of one another represent hydrogen, halogen, alkyl, alkoxy, alkenyloxy, haloalkyl, haloalkoxy, haloalkenyloxy, nitro or cyano, A represents in each case optionally halogen-substituted alkyl, alkenyl, alkoxyalkyl, saturated, optionally substituted cycloalkyl, D represents hydrogen or represents in each case optionally halogen-substituted alkyl, alkenyl or alkoxyalkyl, A and D together with the atoms to which they are attached represent a saturated or unsaturated 6- or 7-membered ring which optionally contains at least one further heteroatom and which is unsubstituted or substituted in the A, D moiety or represent an optionally substituted 5-membered ring;

G represents hydrogen (a) or represents one of the groups

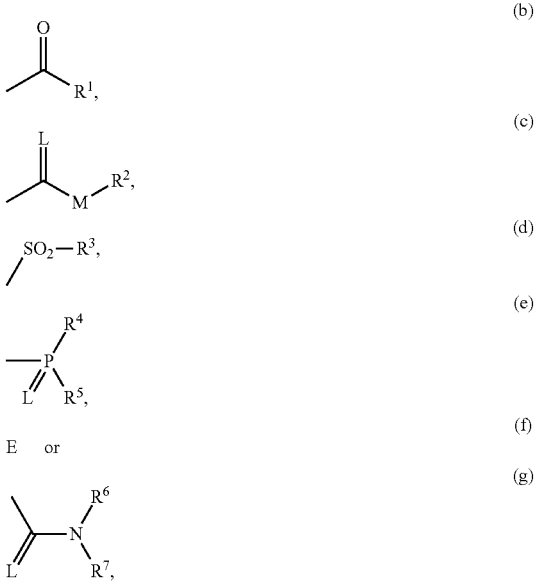

in which

E represents a metal ion or an ammonium,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, represents in each case optionally substituted phenyl, phenylalkyl, hetaryl, phenoxyalkyl or hetaryloxyalkyl, $R^2$ represents in each case optionally halogen-substituted alkyl, alkenyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the N atom to which they are attached represent a, ring which is optionally interrupted by oxygen or sulphur.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, their preparation and use and compositions comprising them. However, hereinbelow, for the sake of simplicity, only compounds of the formula (I) are referred to, although what is meant are both the pure compounds and, if appropriate, also mixtures having varying proportions of isomeric compounds.

Depending on the position of the substituent G, the compounds of the formula (I) can be present in the two isomeric forms of the formulae (I-A) and (I-B)

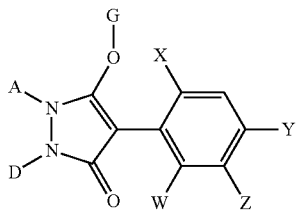
(I-A)

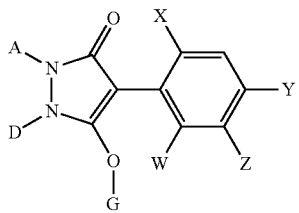
(I-B)

which is meant to be indicated by the broken line in the formula (I).

The compounds of the formulae (I-A) and (I-B) can be present both as mixtures and in the form of their pure isomers. Mixtures of the compounds of the formulae (I-A) and (I-B) can, if appropriate, be separated in a known manner by physical methods, for example by chromatographic methods.

For reasons of clarity, in the following text only one of the possible isomers is shown in each case. This does not exclude that the compounds may, if appropriate, be present in the form of the isomer mixtures or in the respective other isomeric form.

Including the various meanings (a), (b), (c), (d), (e), (f) and (g) of group G, the following principal structures (I-a) to (I-g) result,

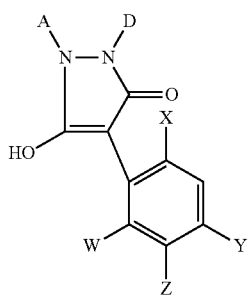
(I-a)

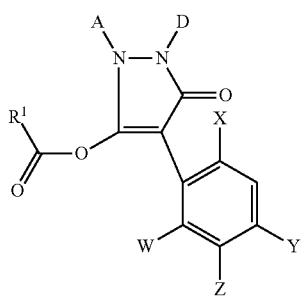
(I-b)

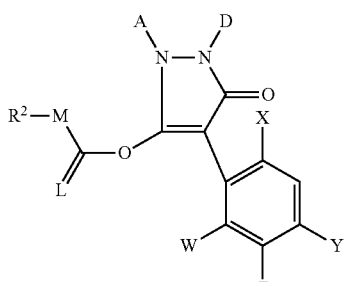
(I-c)

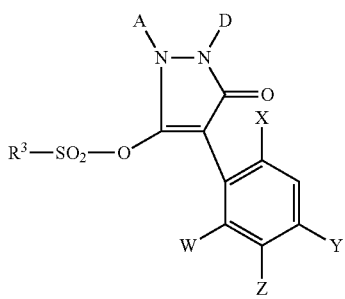
(I-d)

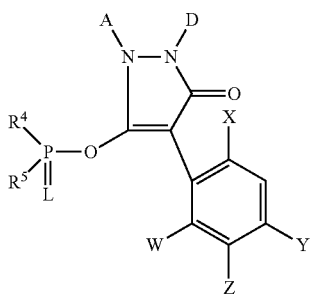
(I-e)

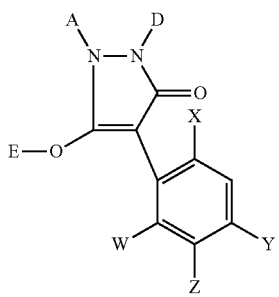
(I-f)

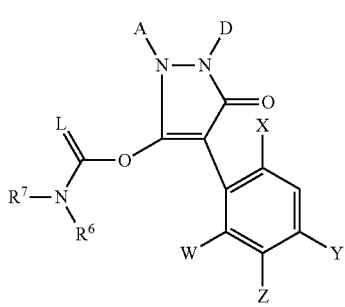
(I-g)

in which
A, D, E, L, M, W, X, Y, Z, $R^1$, $R^2$, $R^3$, $R^4$, $R^5$, $R^6$, $R^7$ are as defined above.

(A) It has been found that substituted 3-hydroxy-4-phenyl-5-oxopyrazolines or their diones of the formula (I-a)

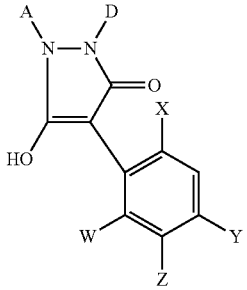 (I-a)

in which
A, D, W, X, Y and Z are as defined above are obtained
when
(α) halochlorocarbonyl ketones of the formula (II)

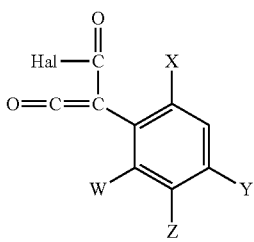 (II)

in which
W, X, Y and Z are as defined above
and
Hal represents halogen (in particular chlorine or bromine)
or
(β) malonic acid derivatives of the formula (III)

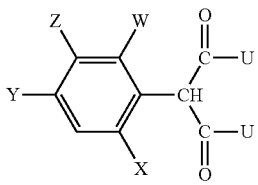 (III)

in which
W, X, Y and Z are as defined above and
U represents $NH_2$ or $C_1$-$C_8$-alkoxy
are reacted with hydrazines of the formula (IV)

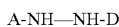 (IV)

A-NH—NH-D in which
A and D are as defined above,
if appropriate in the presence of a diluent and if appropriate in the presence of a base, or γ) compounds of the formula (V)

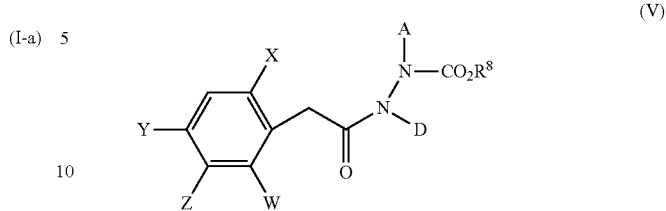 (V)

in which
A, D, W, X, Y and Z are as defined above and
$R^8$ represents $C_1$-$C_8$-alkyl
are reacted, if appropriate in the presence of a diluent and if appropriate in the presence of a base.
(B) Furthermore, compounds of the formulae (I-a) to (I-g) shown above in which A, D, G, W, X, Y and Z are as defined above are obtained when compounds of the formulae (I'-a) to (I'-g)

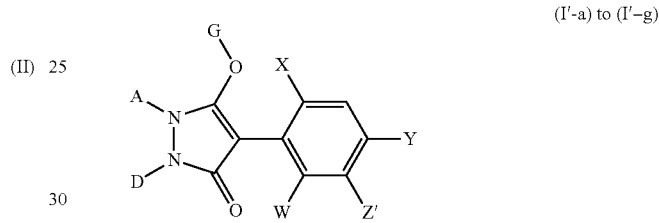 (I'-a) to (I'-g)

in which
A, D, G, W, X and Y are as defined above and
Z' represents chlorine, bromine, iodine, preferably bromine,
are reacted with boronic acids of the formula (VI)

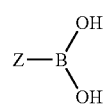 (VI)

in which
Z is as defined above
in the presence of a solvent, a base and a catalyst, suitable catalysts being, in particular, palladium complexes.
Moreover, it has been found
(C) that the compounds of the formula (I-b) shown above in which A, D, $R^1$, W, X, Y and Z are as defined above are obtained when compounds of the formula (I-a) shown above in which A, D, W, X, Y and Z are as defined above are in each case reacted
(α) with acid halides of the formula (VII)

 (VII)

in which
$R^1$ is as defined above and
Hal represents halogen (in particular chlorine or bromine)

or (β) with carboxylic anhydrides of the formula (VIII)

$$R^1—CO—O—CO—R^1 \qquad (VIII)$$

in which
R$^1$ is as defined above,
if appropriate in the presence of a diluent and if appropriate in the presence of an acid binder;

(D) that the compounds of the formula (I-c) shown above in which A, D, R$^2$, M, W, X, Y and Z are as defined above and L represents oxygen are obtained when compounds of the formula (I-a) shown above in which A, D, W, X, Y and Z are as defined above are in each case reacted
with chloroformic esters or chloroformic thioesters of the formula (IX)

$$R^2\text{-M-CO—Cl} \qquad (IX)$$

in which
R$^2$ and M are as defined above,
if appropriate in the presence of a diluent and if appropriate in the presence of an acid binder;

(E) that compounds of the formula (I-c) shown above in which A, D, R$^2$, M, W, X, Y and Z are as defined above and L represents sulphur are obtained when compounds of the formula (I-a) shown above in which A, D, W, X, Y and Z are as defined above are in each case reacted
with chloromonothioformic esters or chlorodithioformic esters of the formula (X)

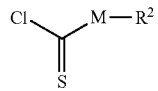
(X)

in which
M and R$^2$ are as defined above,
if appropriate in the presence of a diluent and if appropriate in the presence of an acid binder;
and (F) that compounds of the formula (I-d) shown above in which A, D, R$^3$, W, X, Y and Z are as defined above are obtained when compounds of the formula (I-a) shown above in which A, D, W, X, Y and Z are as defined above are in each case reacted
with sulphonyl chlorides of the formula (XI)

$$R^3—SO_2—Cl \qquad (XI)$$

in which
R$^3$ is as defined above,
if appropriate in the presence of a diluent and if appropriate in the presence of an acid binder, (G) that compounds of the formula (I-e) shown above in which A, D, L, R$^4$, R$^5$, W, X, Y and Z are as defined above when compounds of the formula (I-a) shown above in which A, D, W, X, Y and Z are as defined above are in each case reacted
with phosphorus compounds of the formula (XII)

(XII)

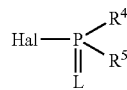

in which
L, R$^4$ and R$^5$ are as defined above and
Hal represents halogen (in particular chlorine or bromine),
if appropriate in the presence of a diluent and if appropriate in the presence of an acid binder, (H) that compounds of the formula (I-f) shown above in which A, D, E, W, X, Y and Z are as defined above are obtained when compounds of the formula (I-a) in which A, D, W, X, Y and Z are as defined above are in each case reacted
with metal compounds or amines of the formulae (XIII) or (XIV), respectively,

$$Me(OR^9)_t \qquad (XIII)$$

(XIV)

in which
Me represents a mono- or divalent metal (preferably an alkali metal or alkaline earth metal, such as lithium, sodium, potassium, magnesium or calcium),
t represents the number 1 or 2 and
R$^9$, R$^{10}$, R$^{11}$, R$^{12}$ independently of one another represent hydrogen or alkyl (preferably C$_1$-C$_8$-alkyl),
if appropriate in the presence of a diluent, (I) that compounds of the formula (I-g) shown above in which A, D, L, R$^6$, R$^7$, W, X, Y and Z are as defined above are obtained when compounds of the formula (I-a) shown above in which A, D, W, X, Y and Z are as defined above are in each case reacted
(α) with isocyanates or isothiocyanates of the formula (XV)

$$R^6—N=C=L \qquad (XV)$$

in which
R$^6$ and L are as defined above,
if appropriate in the presence of a diluent and if appropriate in the presence of a catalyst, or (β) with carbamoyl chlorides or thiocarbamoyl chlorides of the formula (XVI)

(XVI)

in which
L, R$^6$ and R$^7$ are as defined above,
if appropriate in the presence of a diluent and if appropriate in the presence of an acid binder.

Furthermore, it has been found that the novel compounds of the formula (I) are highly effective pesticides, preferably insecticides and/or acaricides and/or herbicides.

Surprisingly, it has now also been found that certain 4-biphenyl-substituted pyrazolidine-3,5-dione derivatives, when used together with the crop plant compatibility-improving compounds (safeners/antidotes) described below, prevent damage of the crop plants very efficiently and can be used particularly advantageously as broad-spectrum combination preparations for the selective control of unwanted plants in crops of useful plants, such as, for example, in cereals, but also in maize, soybean and rice.

The invention also provides selective herbicidal compositions, comprising an effective amount of an active compound combination comprising, as components (a') at least one 4-biphenyl-substituted pyrazolidine-3,5-dione derivative of the formula (I) in which A, D, G, W, X, Y and Z are as defined above
and
(b') at least one crop plant compatibility-improving compound from the following group of compounds:
4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl-cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl 1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl-cf. also related compounds in EP-A-174562 and EP-A-346620), phenylmethyl 2-chloro-4-trifluoromethylthiazole-5-carboxylate (flurazole), 4-chloro-N-(1,3-dioxolan-2-yl-methoxy)-α-trifluoroacetophenone oxime (fluxofenim), 3-dichloro-acetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl-cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl-cf. also related compounds in WO-A-91/07874), 2-dichloromethyl-2-methyl-1, 3-dioxolane (MG-191), 2-propenyl-1-oxa-4-azaspiro[4.5] decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-yl-methyl)-N-(2-propenyl)acetamide (PPG-1292), 3-dichloro-acetyl-2,2-dimethyl-oxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazol-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquino-line-8-oxyacetate, methyl 5-chloroquinoxaline-8-oxyacetate, ethyl 5-chloroquinoline-8-oxyacetate, allyl 5-chloro-quinoxaline-8-oxyacetate, 2-oxoprop-1-yl 5-chloroquinoline-8-oxyacetate, diethyl 5-chloro-quinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxy-benzophenone, 1-bromo-4-chloromethylsulphonylbenzene, 1-[4-(N-2-methoxybenzoyl-sulphamoyl)phenyl]-3-methylurea (also known as N-(2-methoxybenzoyl)-4-[(methylaminocarbonyl)amino] benzenesulphonamide), 1-[4-(N-2-methoxybenzoylsulphamoyl)-phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclo-propylaminocarbonyl) benzenesulphonamide, and/or one of the following compounds, defined by general formulae, of the general formula (IIa)

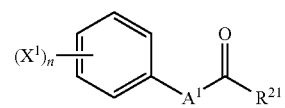

(IIa)

or of the general formula (IIb)

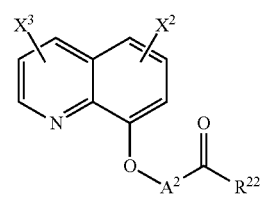

(IIb)

or of the formula (IIc)

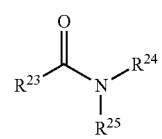

(IIc)

where n represents a number between 0 and 5, $A^1$ represents one of the divalent heterocyclic groupings shown below

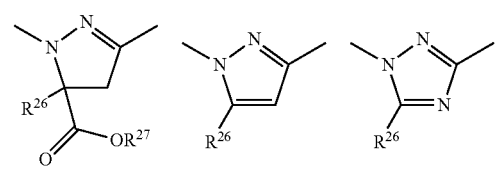

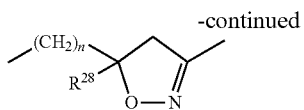

n represents a number between 0 and 5, $A^2$ represents optionally $C_1$-$C_4$-alkyl- and/or $C_1$-$C_4$-alkoxy-carbonyl-substituted alkanediyl having 1 or 2 carbon atoms, $R^{21}$ represents hydroxyl, mercapto, amino, $C_1$-$C_6$-alkoxy, $C_1$-$C_6$-alkylthio; $C_1$-$C_6$-alkylamino or di-($C_1$-$C_4$-alkyl)-amino, $R^{22}$ represents hydroxyl, mercapto, amino, $C_1$-$C_6$-alkoxy, $C_1$-$C_8$-alkenyloxy, $C_1$-$C_6$-alkylthio, $C_1$-$C_6$-alkylamino or di-($C_1$-$C_4$-alkyl)-amino, $R^{23}$ represents in each case optionally fluorine-, chlorine- and/or bromine-substituted $C_1$-$C_4$-alkyl, $R^{24}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{25}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or together with $R^{24}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{26}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^{27}$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{28}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, represents nitro, cyano, halogen, $C_1$-$C_4$-alkyl, $C_1$-$C_4$ haloalkyl, $C_1$-$C_4$-alkoxy or $C_1$-$C_4$-haloalkoxy, $X^2$ represents hydrogen, cyano, nitro, halogen, $C_1$-$C_1$-alkyl, $C_1$-$C_4$ haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

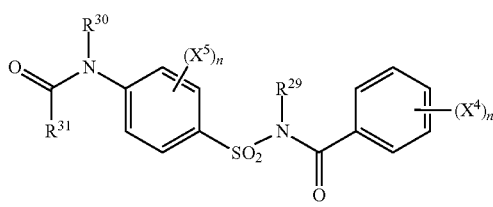

or the general formula (IIe)

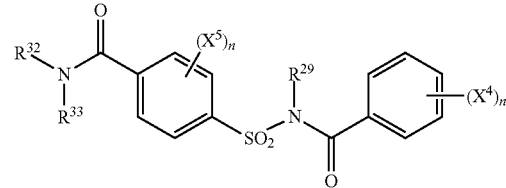

where n represents a number between 0 and 5, $R^{29}$ represents hydrogen or $C_1$-$C_4$-alkyl, $R^{30}$ represents hydrogen or $C_1$-$C_4$-alkyl, $R^{31}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)-amino, or in each case optionally cyano-, halogen- or $C_1$-$C_4$alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{32}$ represents hydrogen, optionally cyano-, hydroxyl-, halogen- or $C_1$-$C_4$-alkoxy-substituted $C_1$-$C_6$-alkyl, in each case optionally cyano-, or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-alkoxy- or $C_1$-$C_4$-haloalkoxy-substituted phenyl, or together with $R^{32}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl; hydroxyl, amino, halogen, $C_1$-$C_4$ alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of radicals listed in the formulae mentioned above and below are illustrated below:

X preferably represents halogen, $C_1$-$C_6$-alkyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-halo-alkoxy, $C_3$-$C_6$-haloalkenyloxy, nitro or cyano, W and Y independently of one another preferably represent hydrogen, halogen, $C_1$-$C_6$-alkyl, $C_1$-$C_6$-haloalkyl, $C_1$-$C_6$-alkoxy, $C_1$-$C_6$-haloalkoxy, nitro or cyano, Z preferably represents one of the radicals

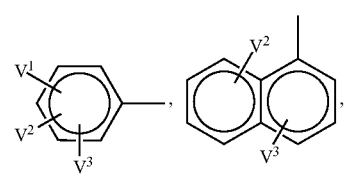

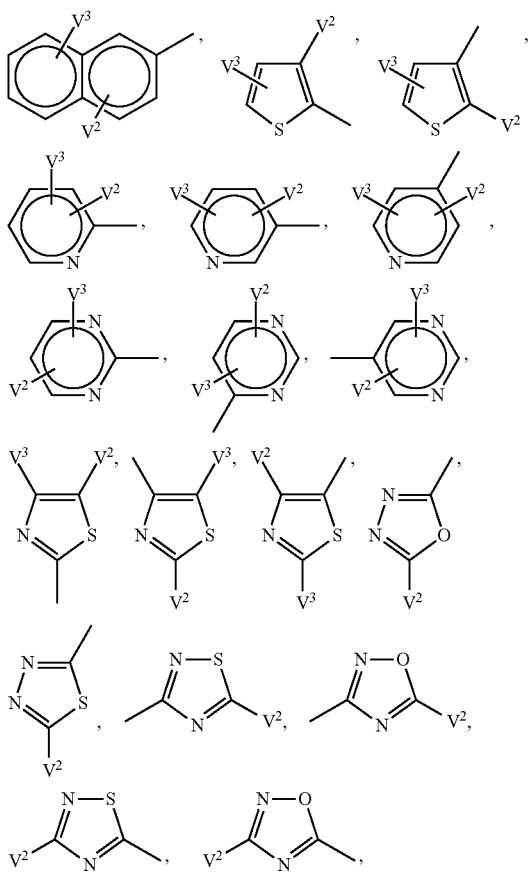

$V^1$ preferably represents halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or poly-substituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents in each case optionally halogen-substituted $C_1$-$C_8$-alkyl, $C_3$-$C_8$-alkenyl or optionally $C_1$-$C_4$-alkyl-, halogen- or $C_1$-$C_4$-alkoxy-substituted $C_3$-$C_6$-cycloalkyl, D preferably represents hydrogen, represents in each case optionally halogen-substituted $C_1$-$C_8$-alkyl or $C_3$-$C_8$-alkenyl, A and D together preferably represent in each case optionally substituted $C_4$-$C_6$-alkanediyl or $C_4$-$C_6$-alkenediyl in which optionally one methylene group may be replaced by oxygen or sulphur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl, benzyloxy or a further $C_1$-$C_6$-alkanediyl grouping, or which optionally contains one of the following groups

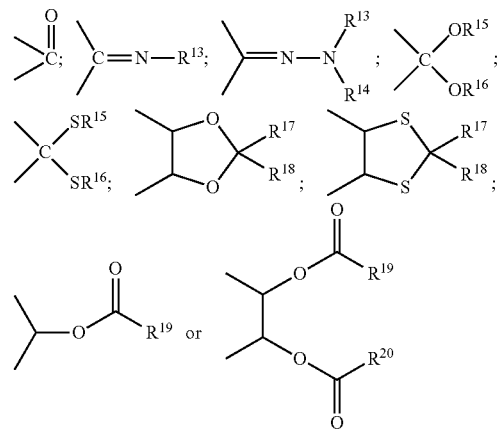

or preferably represents $C_3$-alkanediyl which is optionally mono- to trisubstituted by halogen, $C_1$-$C_6$-alkyl, $C_1$-$C_4$-haloalkyl or $C_1$-$C_6$-alkoxy, G preferably represents hydrogen (a) or represents one of the groups

 (b)

 (c)

 (d)

 (e)

E or (f)

(g)

in particular (a), (b) or (c),
in which
E represents a metal ion or an ammonium ion,
L represents oxygen or sulphur and
M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen, $C_1$-$C_6$-alkyl or $C_1$-$C_6$-alkoxy-substituted $C_3$-$C_8$-cycloalkyl in which optionally one or more (preferably no more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted, phenyl, represents optionally halogen-, nitro-, cyano-, $C_1$-$C_6$-alkyl-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, furanyl or thienyl), represents optionally halogen- or $C_1$-$C_6$-alkyl-substituted phenoxy-$C_1$-$C_6$-alkyl or represents in each case optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_9$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkylamino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, represent optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one methylene group is replaced by oxygen or sulphur, $R^{13}$ preferably represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14}$ preferably represents hydrogen or $C_1$-$C_8$-alkyl or $R^{13}$ and $R^{14}$ together preferably represent $C_4$-$C_6$-alkanediyl, $R^{15}$ and $R^{16}$ are identical or different and preferably represent $C_1$-$C_6$-alkyl or $R^{15}$ and $R^{16}$ together preferably represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17}$ and $R^{18}$ independently of one another preferably represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17}$ and $R^{18}$ together with the carbon atom to which they are attached preferably represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19}$ and $R^{20}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine.

W particularly preferably represents hydrogen, fluorine, chlorine, bromine, methyl, ethyl, methoxy or ethoxy, X particularly preferably represents fluorine, chlorine, bromine, $C_1$-$C_4$-alkyl, $C_1$-$C_4$-alkoxy, $C_3$-$C_4$-alkenyloxy, $C_1$-$C_4$-haloalkyl, $C_1$-$C_4$-haloalkoxy, $C_3$-$C_4$-haloalkenyloxy, nitro or cyano, Y particularly preferably represents hydrogen, fluorine, chlorine, bromine, $C_1$-$C_4$-alkyl, $C_1$-$C_2$-haloalkyl, $C_1$-$C_4$-alkoxy or $C_1$-$C_2$-haloalkoxy, Z particularly preferably represents one of the radicals

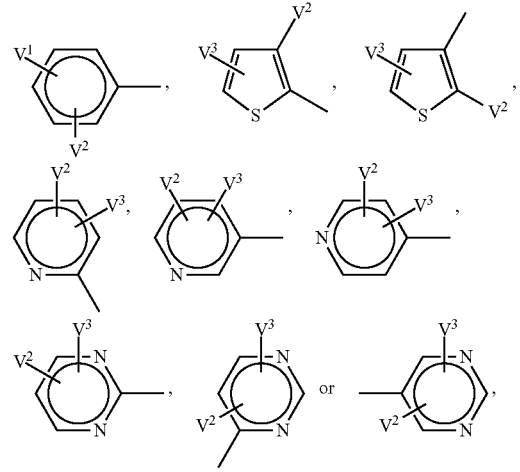

$V^1$ particularly preferably represents fluorine, chlorine, bromine, $C_1$-$C_6$-alkyl, $C_1$-$C_4$-alkoxy, $C_1$-$C_4$-alkylthio, $C_1$-$C_4$-alkylsulphonyl, $C_1$-$C_2$-haloalkyl, $C_1$-$C_2$-haloalkoxy, nitro, cyano or represents phenyl, phenoxy, phenoxy-$C_1$-$C_2$-alkyl, phenyl-$C_1$-$C_2$-alkoxy, phenylthio-$C_1$-$C_2$-alkyl or phenyl-$C_1$-$C_2$-alkylthio, each of which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents $C_1$-$C_6$-alkyl, $C_3$-$C_6$-alkenyl or $C_3$-$C_6$-cycloalkyl, D particularly preferably represents hydrogen, $C_1$-$C_6$-alkyl or $C_3$-$C_6$-alkenyl, A and D together particularly preferably represent optionally substituted $C_4$-$C_5$-alkanediyl in which optionally one methylene group may be replaced by a carbonyl group, oxygen or sulphur, possible substitutents being hydroxyl, $C_1$-$C_6$-alkyl, $C_1$-$C_4$-alkoxy or a further $C_1$-$C_4$-alkanediyl grouping, or which optionally contains one of the following groups

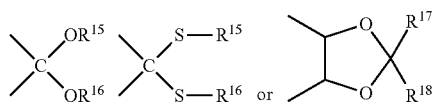

or represent $C_3$-alkanediyl which is optionally mono- or disubstituted by fluorine, chlorine, trifluoromethyl, methyl, ethyl or methoxy, G particularly preferably represents hydrogen (a) or represents one of the groups

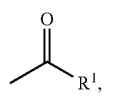 (b)

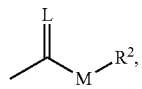 (c)

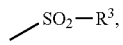 (d)

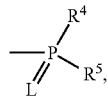 (e)

E or (f)

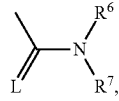 (g)

in particular (a), (b) or (c),
in which
E represents a metal ion or an ammonium ion,
L represents oxygen or sulphur and
M represents oxygen or sulphur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen,
represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
represents $C_3$-$C_6$-cycloalkyl which is optionally monosubstituted by $C_1$-$C_2$-alkyl or $C_1$-$C_2$-alkoxy or
represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoro-methoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine, or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-halo-alkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, represents $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, each of which is optionally mono- to trisubstituted by fluorine, represents phenyl which is optionally mono- or disubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent a $C_4$-$C_5$-alkylene radical which is optionally mono- or disubstituted by methyl or ethyl and in which optionally one methylene group is replaced by oxygen or sulphur, $R^{15}$ and $R^{16}$ are identical and particularly preferably represent $C_1$-$C_4$-alkyl, $R^{15}$ and $R^{16}$ together particularly preferably represent a $C_2$-$C_3$-alkanediyl radical which is optionally mono- or disubstituted by methyl, ethyl, propyl or isopropyl, $R^{17}$ and $R^{18}$ independently of one another particularly preferably represent hydrogen, represent methyl, ethyl, propyl, isopropyl, butyl, isobutyl or tert-butyl, each of which is optionally mono- to trisubstituted by fluorine and/or chlorine or $R^{17}$ and $R^{18}$ together with the carbon to which they are attached particularly preferably represent a carbonyl group or represent optionally methyl-, ethyl-, methoxy- or ethoxy-substituted $C_5$-$C_6$-cycloalkyl in which optionally one methylene group is replaced by oxygen.

In the radical definitions mentioned as being particularly preferred, halogen represents fluorine, chlorine, bromine and iodine, in particular fluorine, chlorine and bromine.

W very particularly preferably represents hydrogen, methyl, ethyl or chlorine,

X very particularly preferably represents chlorine methyl, ethyl, propyl, methoxy, ethoxy, propoxy or trifluoromethyl, Y very particularly preferably represents hydrogen, chlorine or methyl, Z very particularly preferably represents one of the radicals

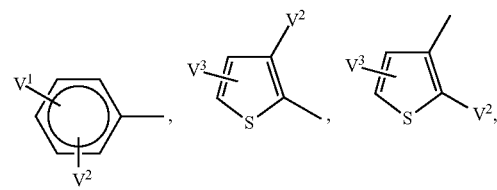

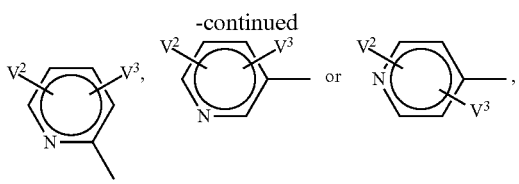

in particular

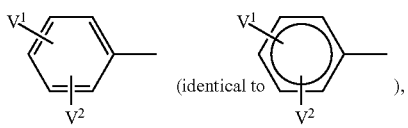

(identical to ...), $V^1$ very particularly preferably represents fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, $SO_2C_2H_5$, $SCH_3$, phenoxy, nitro or cyano, $V^2$ and $V^3$ independently of one another very particularly preferably represent hydrogen, fluorine, chlorine, methyl, methoxy or trifluoromethyl, A very particularly preferably represents methyl, ethyl, propyl or butyl, D very particularly preferably represents hydrogen, methyl or ethyl, A and D together very particularly preferably represent optionally substituted $C_4$-$C_5$-alkanediyl in which optionally one methylene group is replaced by oxygen or sulphur and which is optionally substituted by hydroxyl, methyl, ethyl, methoxy, ethoxy or by a further $C_1$-$C_4$-alkanediyl grouping or represent $C_3$-alkanediyl which is optionally mono- or disubstituted by fluorine, methyl, trifluoromethyl or methoxy, G very particularly preferably represents hydrogen (a) or represents one of the groups (b) 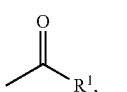

(c) 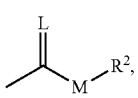

(d) 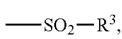

(e) 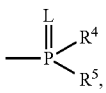

(f)
(g)

E or

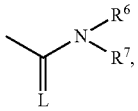

in particular (a), (b) or (c),
in which
E represents a metal ion equivalent or an ammonium ion,
L represents oxygen or sulphur and
M represents oxygen or sulphur, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally mono- to trisubstituted by fluorine, or represents cyclopropyl or cyclohexyl, each of which is optionally monosubstituted by fluorine, chorine, methyl or methoxy,
represents phenyl which is optionally monosubstituted by fluorine, chlorine, bromine, cyano, nitro, methyl, methoxy, trifluoromethyl or trifluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, each of which is optionally monosubstituted by fluorine,
or represents phenyl or benzyl, each of which is optionally monosubstituted by fluorine, chlorine, cyano, nitro, methyl, ethyl, n-propyl, i-propyl, methoxy, ethoxy, trifluoromethyl or trifluoromethoxy, $R^3$ very particularly preferably represents methyl, ethyl, n-propyl, isopropyl, each of which is optionally mono- to trisubstituted by fluorine, or represents phenyl or benzyl, each of which is optionally monosubstituted by fluorine, chlorine, bromine, methyl, tert-butyl, methoxy, trifluoromethyl, trifluoromethoxy, cyano or nitro, $R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio, each of which is optionally mono- to trisubstituted by fluorine, or represents phenyl, phenoxy or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl, $R^5$ very particularly preferably represents methoxy, ethoxy, propoxy, butoxy, methylthio, ethylthio, propylthio or butylthio, $R^6$ very particularly preferably represents hydrogen, represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, each of which is optionally mono- to trisubstituted by fluorine, represents phenyl which is optionally monosubstituted by fluorine, chlorine, bromine, trifluoromethyl, methyl or methoxy, represents benzyl which is optionally monosubstituted by fluorine, chlorine, bromine, methyl, trifluoromethyl or methoxy, $R^7$ very particularly preferably represents methyl, ethyl, propyl, isopropyl, butyl, isobutyl or allyl, $R^6$ and $R^7$ very particularly preferably represent a $C_4$-$C_5$-alkylene radical in which optionally one methylene group is replaced by oxygen or sulphur.

W especially preferably represents hydrogen or methyl,
X especially preferably represents chlorine or methyl,
Y especially preferably represents hydrogen or methyl,
Z especially preferably represents one of the radicals

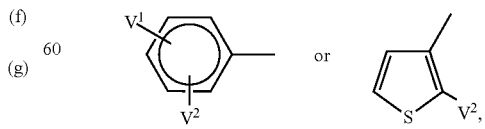

$V^1$ especially preferably represents fluorine, chlorine, methyl, isopropyl, methoxy, trifluoromethyl, trifluoromethoxy, $SO_2C_2H_5$, $SCH_3$, phenoxy or nitro, $V^2$ especially preferably represents hydrogen, fluorine, chlorine or trifluoromethyl, A especially preferably represents methyl or ethyl, D especially preferably represents methyl or ethyl, A and D together especially preferably represent optionally substituted $C_4$-$C_5$-alkanediyl in which optionally one methylene group is replaced by oxygen and which is optionally substituted by a further $C_1$-$C_2$-alkanediyl grouping, or represents $C_3$-alkanediyl which is optionally mono- or disubstituted by fluorine, methyl or trifluoromethyl, G especially preferably represents hydrogen (a) or represents one of the groups

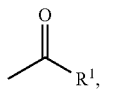
(b)

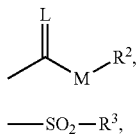
(c)

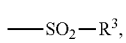
(d)

in which

L represents oxygen and

M represents oxygen, $R^1$ especially preferably represents $C_1$-$C_6$-alkyl or cyclopropyl, $R^2$ especially preferably represents $C_1$-$C_8$-alkyl or $C_1$-$C_4$-alkoxy-$C_2$-$C_3$-alkyl, $R^3$ especially preferably represents methyl, ethyl or isopropyl.

The abovementioned general or preferred radical definitions or illustrations can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Special preference according to the'invention is given to the compounds of the formula (I) which contain a combination of the meanings listed above as being especially preferred.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitution the substituents can be identical or different.

In addition to the compounds mentioned in the Preparation Examples, the following compounds of the formula (I-1-a) may be specifically mentioned:

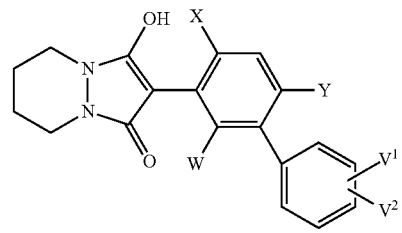

TABLE 1

| W | X | Y | $V^1$ | $V^2$ |
|---|---|---|---|---|
| H | CH$_3$ | H | 4-Cl | H |
| H | CH$_3$ | CH$_3$ | 4-Cl | H |
| CH$_3$ | CH$_3$ | CH$_3$ | 4-Cl | H |
| H | CH$_3$ | H | 3-Cl | H |
| H | CH$_3$ | CH$_3$ | 3-Cl | H |
| CH$_3$ | CH$_3$ | CH$_3$ | 3-Cl | H |
| H | CH$_3$ | H | 2-Cl | 4-Cl |
| H | CH$_3$ | CH$_3$ | 2-Cl | 4-Cl |
| CH$_3$ | CH$_3$ | CH$_3$ | 2-Cl | 4-Cl |
| H | CH$_3$ | H | 4-CF$_3$ | H |
| H | CH$_3$ | CH$_3$ | 4-CF$_3$ | H |
| CH$_3$ | CH$_3$ | CH$_3$ | 4-CF$_3$ | H |
| H | CH$_3$ | H | 4-F | H |
| H | CH$_3$ | CH$_3$ | 4-F | H |
| CH$_3$ | CH$_3$ | CH$_3$ | 4-F | H |
| H | CH$_3$ | H | 4-CH$_3$ | H |
| H | CH$_3$ | CH$_3$ | 4-CH$_3$ | H |
| CH$_3$ | CH$_3$ | CH$_3$ | 4-CH$_3$ | H |
| H | Cl | H | 4-Cl | H |
| H | Cl | H | 3-Cl | H |
| H | Cl | H | 4-CF$_3$ | H |
| H | Cl | H | 4-F | H |
| H | Cl | H | 2-Cl | 4-Cl |

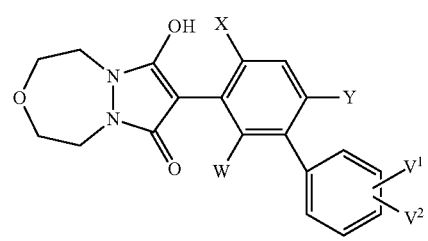

TABLE 2

| W | X | Y | $V^1$ | $V^2$ |
|---|---|---|---|---|
| H | CH$_3$ | H | 4-Cl | H |
| H | CH$_3$ | CH$_3$ | 4-Cl | H |
| CH$_3$ | CH$_3$ | CH$_3$ | 4-Cl | H |
| H | CH$_3$ | H | 3-Cl | H |
| H | CH$_3$ | CH$_3$ | 3-Cl | H |
| CH$_3$ | CH$_3$ | CH$_3$ | 3-Cl | H |
| H | CH$_3$ | H | 2-Cl | 4-Cl |
| H | CH$_3$ | CH$_3$ | 2-Cl | 4-Cl |
| CH$_3$ | CH$_3$ | CH$_3$ | 2-Cl | 4-Cl |
| H | CH$_3$ | H | 4-CF$_3$ | H |
| H | CH$_3$ | CH$_3$ | 4-CF$_3$ | H |
| CH$_3$ | CH$_3$ | CH$_3$ | 4-CF$_3$ | H |
| H | CH$_3$ | H | 4-F | H |
| H | CH$_3$ | CH$_3$ | 4-F | H |
| CH$_3$ | CH$_3$ | CH$_3$ | 4-F | H |
| H | CH$_3$ | H | 4-CH$_3$ | H |
| H | CH$_3$ | CH$_3$ | 4-CH$_3$ | H |
| CH$_3$ | CH$_3$ | CH$_3$ | 4-CH$_3$ | H |

TABLE 2-continued

| W | X | Y | V¹ | V² |
|---|---|---|---|---|
| H | Cl | H | 4-Cl | H |
| H | Cl | H | 4-Cl | H |
| H | Cl | H | 4-CF$_3$ | H |
| H | Cl | H | 4-F | H |
| H | Cl | H | 2-Cl | 4-Cl |

Preferred meanings of the groups listed above in connection with the crop plant compatibility-improving compounds ("herbicide safeners") of the formulae (IIa), (IIb), (IIc), (IId) and (IIe) are defined below.

n preferably represents the numbers 0, 1, 2, 3 or 4.

$A^1$ preferably represents one of the divalent heterocyclic groupings shown below

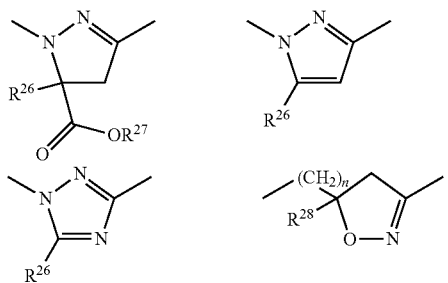

$A^2$ preferably represents in each case optionally methyl-, ethyl-, methoxycarbonyl- or ethoxycarbonyl-substituted methylene or ethylene.

$R^{21}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{22}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{23}$ preferably represents in each case optionally fluorine, chlorine, and/or bromine-substituted methyl, ethyl, n- or i-propyl.

$R^{24}$ preferably represents hydrogen, in each case optionally fluorine and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl, n-, i-, s- or t-butyl-substituted phenyl.

$R^{25}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl, n-, i-, s- or t-butyl-substituted phenyl, or together with $R^{24}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{26}$ preferably represents hydrogen, cyano, fluorine, chlorine, bromine, or represents in each case optionally, fluorine-, chlorine- and/or bromine-substituted methyl, ethyl, n- or i-propyl, cyclo-propyl, cyclobutyl, cyclopentyl, cyclohexyl or phenyl.

$R^{27}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{28}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or difluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$R^{29}$ preferably represents hydrogen, methyl, ethyl, n- or i-propyl.

$R^{30}$ preferably represents hydrogen, methyl, ethyl, n- or i-propyl.

$R^{31}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

$R^{32}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

$R^{33}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{32}$ represents in each case optionally methyl- or ethyl-substituted butane-1,4-diyl(trimethylene), pentane-1,5-diyl, 1-oxabutane-1,4-diyl or 3-oxapentane-1,5-diyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

Examples of the compounds of the formula (IIa) which are very particularly preferred as herbicide safeners according to the invention are listed in Table 3 below.

TABLE 3

Examples of the compounds of the formula (IIa)

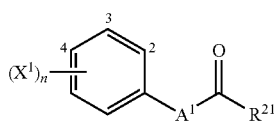

(IIa)

| Example No. | (positions) $(X^1)_n$ | $A^1$ | $R^{21}$ |
|---|---|---|---|
| IIa-1 | (2) Cl, (4) Cl | 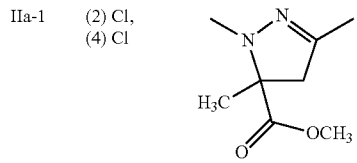 | $OCH_3$ |
| IIa-2 | (2) Cl, (4) Cl | 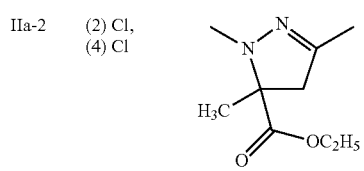 | $OCH_3$ |
| IIa-3 | (2) Cl, (4) Cl | 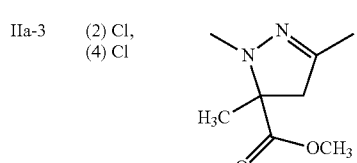 | $OC_2H_5$ |
| IIa-4 | (2) Cl, (4) Cl | 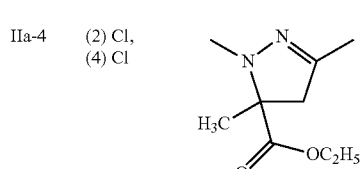 | $OC_2H_5$ |

TABLE 3-continued

Examples of the compounds of the formula (IIa)

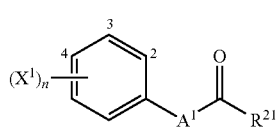

(IIa)

| Example No. | (positions) $(X^1)_n$ | $A^1$ | $R^{21}$ |
|---|---|---|---|
| IIa-5 | (2) Cl | 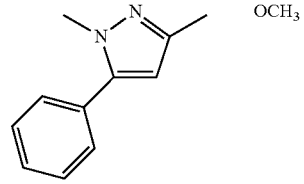 | $OCH_3$ |
| IIa-6 | (2) Cl, (4) Cl | 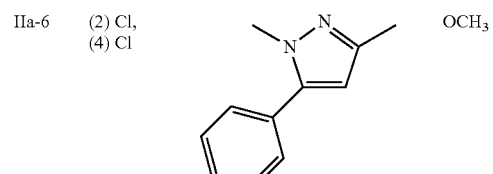 | $OCH_3$ |
| IIa-7 | (2) F | | $OCH_3$ |
| IIa-8 | (2) F | 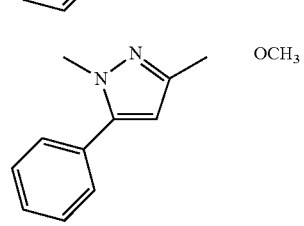 | $OCH_3$ |
| IIa-9 | (2) Cl, (4) Cl | 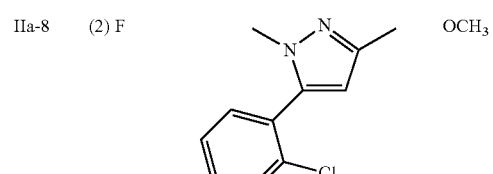 | $OC_2H_5$ |
| IIa-10 | (2) Cl, (4) $CF_3$ | 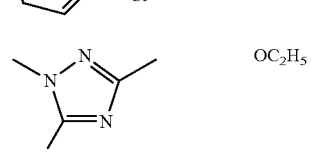 | $OCH_3$ |
| IIa-11 | (2) Cl | 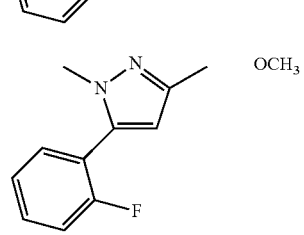 | $OCH_3$ |

TABLE 3-continued

Examples of the compounds of the formula (IIa)

(IIa)

| Example No. | (positions) $(X^1)_n$ | $A^1$ | $R^{21}$ |
|---|---|---|---|
| IIa-12 | — | 5-methyl-5-phenyl-4,5-dihydroisoxazol-3-yl | $OC_2H_5$ |
| IIa-13 | (2) Cl, (4) Cl | 1,3-dimethyl-5-methylpyrazol-5-yl (with $H_3C$) | $OC_2H_5$ |
| IIa-14 | (2) Cl, (4) Cl | 1,3-dimethyl-5-isopropylpyrazole ($C_3H_7$-i) | $OC_2H_5$ |
| IIa-15 | (2) Cl, (4) Cl | 1,3-dimethyl-5-tert-butylpyrazole ($C_4H_9$-t) | $OC_2H_5$ |
| IIa-16 | (2) Cl, (4) Cl | 3-methyl-4,5-dihydroisoxazol-5-ylmethyl | $OC_2H_5$ |
| IIa-17 | (2) Cl, (4) Cl | 3,5-dimethyl-4,5-dihydroisoxazol-3-yl | $OC_2H_5$ |
| IIa-18 | — | 3-methyl-5-phenyl-4,5-dihydroisoxazol-3-yl | OH |

Examples of the compounds of formula (IIb) which are very particularly preferred as herbicide safeners according to the invention are listed in Table 4 below.

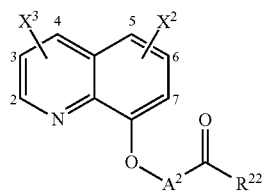

(IIb)

TABLE 4

Examples of the compounds of the formula (IIb)

| Example No. | (position) $X^2$ | (position) $X^3$ | $A^2$ | $R^{22}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | allyloxy-methoxyethyl group |
| IIb-13 | (5) Cl | — | $CH_2$, $CH=CH_2$ branched | $OCH_2CH=CH_2$ |
| IIb-14 | (5) Cl | — | $C_2H_5$ branched ester | $OC_2H_5$ |
| IIb-15 | (5) Cl | — | $CH_3$ branched ester | $OCH_3$ |

Examples of the compounds of formula (IIe) which are very particularly preferred as herbicide safeners according to the invention are listed in Table 5 below.

(IIc)

$$R^{23}-C(O)-N(R^{24})(R^{25})$$

TABLE 5

Examples of the compounds of the formula (IIc)

| Example No. | $R^{23}$ | $N(R^{24}, R^{25})$ |
|---|---|---|
| IIc-1 | $CHCl_2$ | $N(CH_2CH=CH_2)_2$ |
| IIc-2 | $CHCl_2$ | 3-methyl-2,2-dimethyl-oxazolidine |
| IIc-3 | $CHCl_2$ | 3,2,2-trimethyl-5-methyl-oxazolidine |
| IIc-4 | $CHCl_2$ | 1-aza-4-oxa-spiro[4.5]decane |
| IIc-5 | $CHCl_2$ | 3,2,2-trimethyl-5-phenyl-oxazolidine |
| IIc-6 | $CHCl_2$ | 3-methyl-4-methyl-3,4-dihydro-2H-benzo[1,4]oxazine |
| IIc-7 | $CHCl_2$ | 3,2,2-trimethyl-5-(furan-2-yl)-oxazolidine |

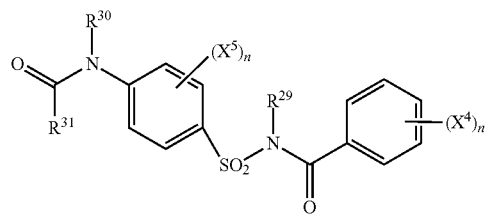

(IId)

TABLE 6

Examples of the compounds of the formula (IId)

| Example No. | $R^{29}$ | $R^{30}$ | $R^{31}$ | (positions) $(X^4)_n$ | (positions) $(X^5)_n$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ | (5) $CH_3$ |
| IId-7 | H | H | $C_2H_5$ | (2) $OCH_3$ | (5) $CH_3$ |
| IId-8 | H | H | $C_3H_7$-n | (2) $OCH_3$ | (5) $CH_3$ |
| IId-9 | H | H | $C_3H_7$-i | (2) $OCH_3$ | (5) $CH_3$ |
| IId-10 | H | H | cyclopropyl | (2) $OCH_3$ | (5) $CH_3$ |
| IId-11 | H | H | $OCH_3$ | (2) $OCH_3$ | (5) $CH_3$ |
| IId-12 | H | H | $OC_2H_5$ | (2) $OCH_3$ | (5) $CH_3$ |
| IId-13 | H | H | $OC_3H_7$-i | (2) $OCH_3$ | (5) $CH_3$ |
| IId-14 | H | H | $SCH_3$ | (2) $OCH_3$ | (5) $CH_3$ |
| IId-15 | H | H | $SC_2H_5$ | (2) $OCH_3$ | (5) $CH_3$ |
| IId-16 | H | H | $SC_3H_7$-i | (2) $OCH_3$ | (5) $CH_3$ |
| IId-17 | H | H | $NHCH_3$ | (2) $OCH_3$ | (5) $CH_3$ |
| IId-18 | H | H | $NHC_2H_5$ | (2) $OCH_3$ | (5) $CH_3$ |
| IId-19 | H | H | $NHC_3H_7$-i | (2) $OCH_3$ | (5) $CH_3$ |
| IId-20 | H | H | NH-cyclopropyl | (2) $OCH_3$ | (5) $CH_3$ |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $OCH_3$ | — |
| IId-25 | H | H | $CH_2$—O—$CH_3$ | (2) $OCH_3$ | — |

Examples of the compounds of formula (IId) which are very particularly preferred as herbicide safeners according to the invention are listed in Table 6 below.

Examples of the compounds of formula (IIe) which are very particularly preferred as herbicide safeners according to the invention are listed in Table 7 below.

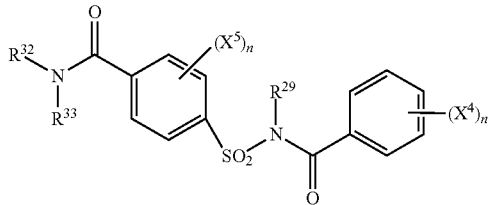

(IIe)

TABLE 7

Examples of the compounds of the formula (IIe)

| Example No. | R²⁹ | R³² | R³³ | (positions) (X⁴)ₙ | (positions) (X⁵)ₙ |
|---|---|---|---|---|---|
| IIe-1 | H | H | CH₃ | (2) OCH₃ | — |
| IIe-2 | H | H | C₂H₅ | (2) OCH₃ | — |
| IIe-3 | H | H | C₃H₇-n | (2) OCH₃ | — |
| IIe-4 | H | H | C₃H₇-i | (2) OCH₃ | — |
| IIe-5 | H | H | △ | (2) OCH₃ | — |
| IIe-6 | H | CH₃ | CH₃ | (2) OCH₃ | — |
| IIe-7 | H | H | CH₃ | (2) OCH₃ (5) CH₃ | — |
| IIe-8 | H | H | C₂H₅ | (2) OCH₃ (5) CH₃ | — |
| IIe-9 | H | H | C₃H₇-n | (2) OCH₃ (5) CH₃ | — |
| IIe-10 | H | H | C₃H₇-i | (2) OCH₃ (5) CH₃ | — |
| IIe-11 | H | H | △ | (2) OCH₃ (5) CH₃ | — |
| IIe-12 | H | CH₃ | CH₃ | (2) OCH₃ (5) CH₃ | — |

Most preferred as crop plant compatibility-improving compounds [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and/or can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in Table 8 below.

TABLE 8

Examples of the combinations according to the invention

| Active compounds of the formula (I) | Safeners |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | IIe-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |

TABLE 8-continued

Examples of the combinations according to the invention

| Active compounds of the formula (I) | Safeners |
| --- | --- |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

Surprisingly, it has now been found that the active compound combinations defined above of 4-biphenyl-substituted pyrazolidine-3,5-dione derivatives of the general formula (I) and safeners (antidotes) from the group (b') listed above, while having very good compatibility with useful plants, have a particularly high herbicidal activity and can be used in various crops, in particular in cereals (especially wheat), but also in soybeans, potatoes, maize and rice, for the selective control of weeds.

Here, it has to be considered to be surprising that, from the large number of known safeners or antidotes capable of antagonising the damaging effect of a herbicide on the crop plants, in particular the compounds of group (b') listed above are suitable to compensate the damaging effect of 4-biphenyl-substituted pyrazolidine-3,5-dione derivatives on the crop plants almost completely, without negatively effecting the herbicidal activity against the weeds to any considerable extent.

Emphasis may be given here to the particularly advantageous effect of the particularly preferred and most preferred combination partners from group (b'), in particular with respect to sparing cereal plants, such as, for example, wheat, barley and rye, but also maize and rice, as crop plants.

Using, for example, according to process (A-α) (chlorocarbonyl) 3-[(6-methyl-3-(4-methyl)-phenyl))phenyl]ketene and hexahydropyridazine as starting materials, the course of the process according to the invention can be represented by the reaction scheme below:

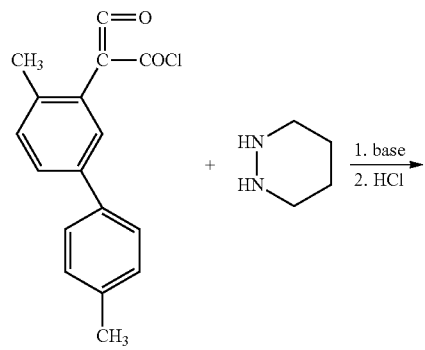

Using, for example, according to process (A-β) diethyl 3-[6-methyl-3-(3-chlorophenyl)]-phenylmalonate and hexahydropyridazine as starting materials, the course of the process according to the invention can be represented by the following reaction scheme:

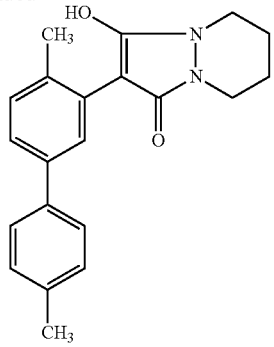

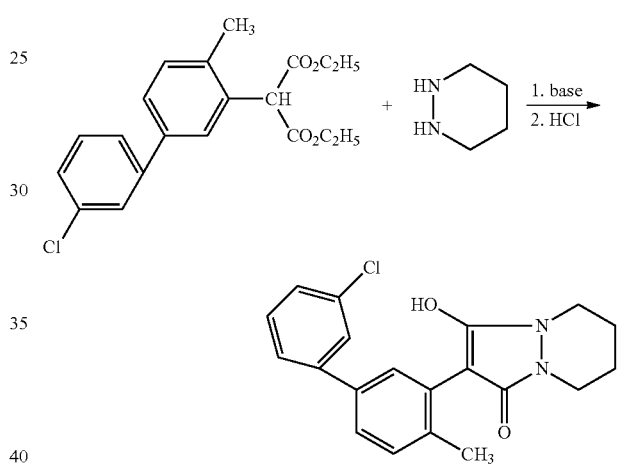

Using, for example, according to process (Aγ) 1-ethoxycarbonyl-2-[6-methyl-3-(4-chlorophenyl)-phenylacetyl] hexahydropyridazine as starting material, the course of the reaction can be represented by the following scheme:

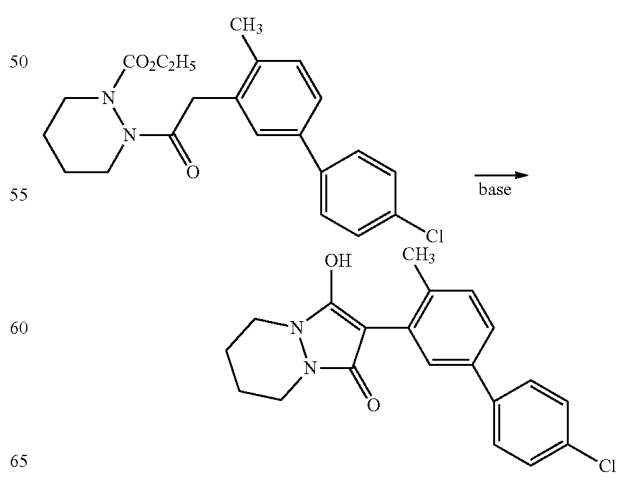

Using, according to process (B), 8-[3-bromo-6-methylphenyl]-1,6-diazabicyclo[4.3.0$^{1.6}$]nonane-7,9-dione and 4-chlorophenylboronic acid as starting materials, the course of the reaction can be represented by the following scheme:

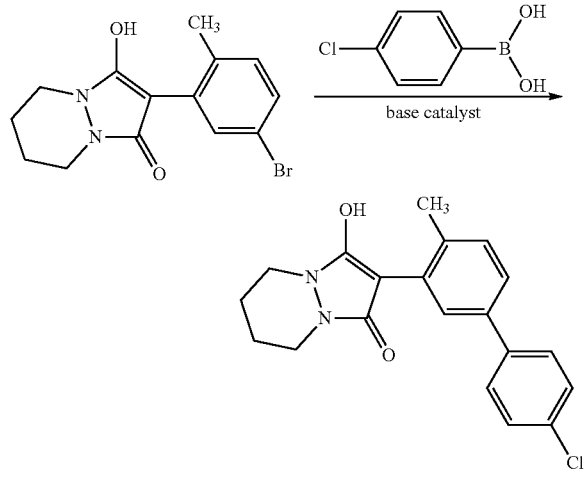

Using, according to process (Cα), 8-[(2-chloro-5-(3-chlorophenyl))phenyl]-1,6-diazabicyclo-[4.3.0$^{1.6}$]nonane-7,9-dione and pivaloyl chloride as starting materials, the course of the process according to the invention can be represented by the following reaction scheme:

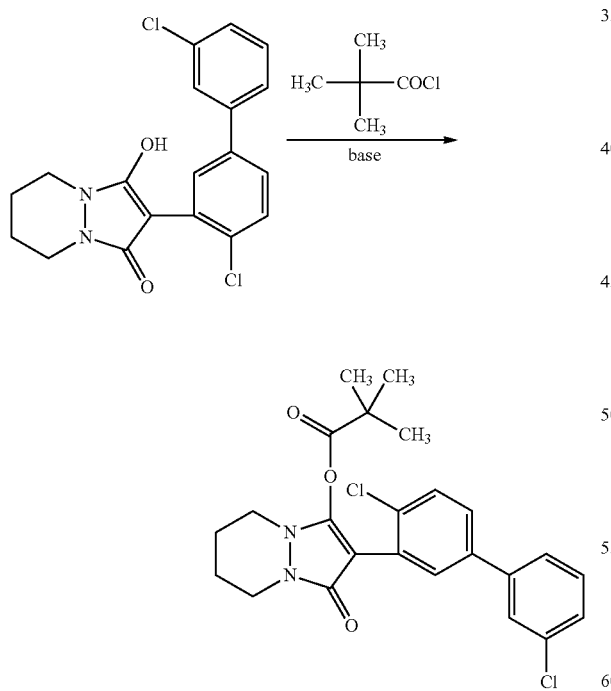

Using, according to process (C) (variant β) 8-[(6-methyl-3-(4-methoxyphenyl))phenyl]-1,6-diaza-bicyclo[4.3.0$^{1.6}$]nonane-7,9-dione and acetic anhydride as starting materials, the course of the process according to the invention can be represented by the following reaction scheme:

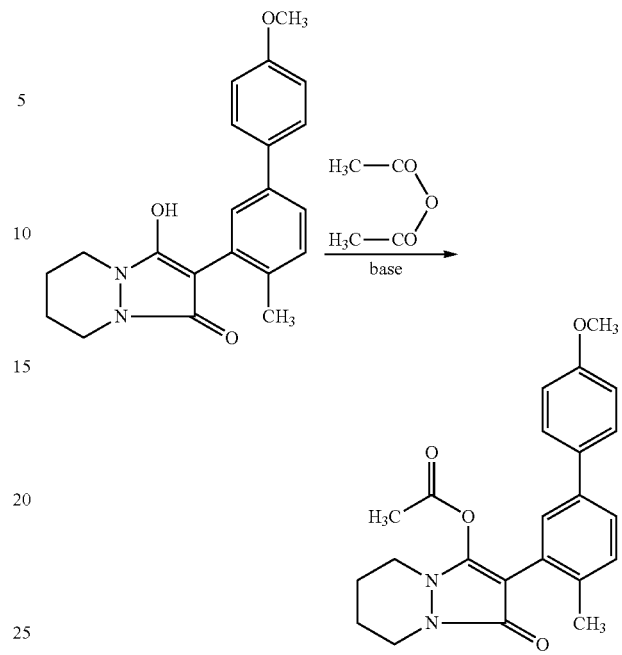

Using, according to process (D) 8-[(2,6-dimethyl-3-(4-chlorophenyl))phenyl]-1,6-diazabicyclo-[4.3.0$^{1.6}$]nonane-7,9-dione and ethoxyethyl chloroformate as starting materials, the course of the process according to the invention can be represented by the following reaction scheme:

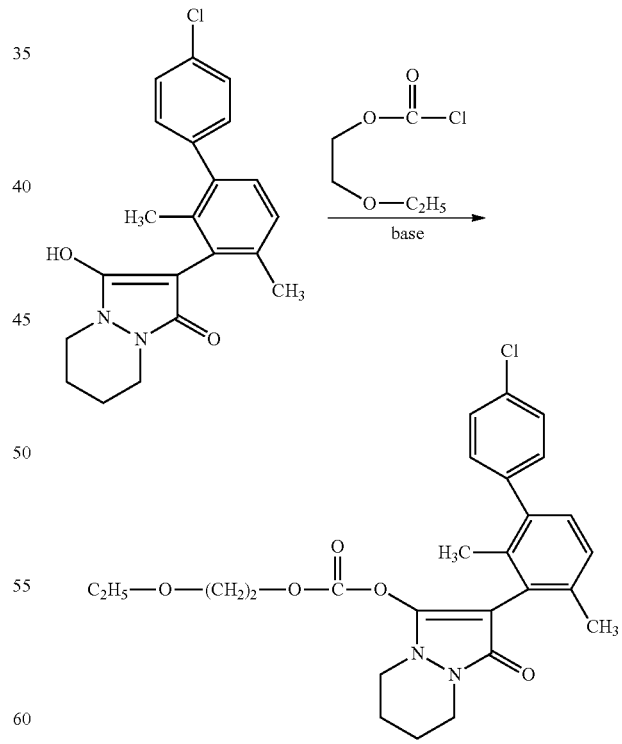

Using, according to process (E), 8-[(2-chloro-5-(4-fluorophenyl))phenyl]-1,6-diazabicyclo-[4.3.0$^{1.6}$]nonane-7,9-dione and methyl chloromonothioformate as starting materials, the course of the reaction according to the invention can be represented as follows:

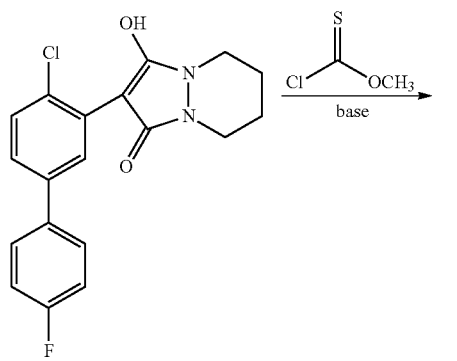

Using, according to process (F) 8-[(2,4,6-trimethyl-3-(4-methylphenyl))phenyl]-1,6-diazabicyclo-[4.3.0^{1.6}]nonane-7,9-dione and methanesulphonyl chloride as starting materials, the course of the reaction can be represented by the following reaction scheme:

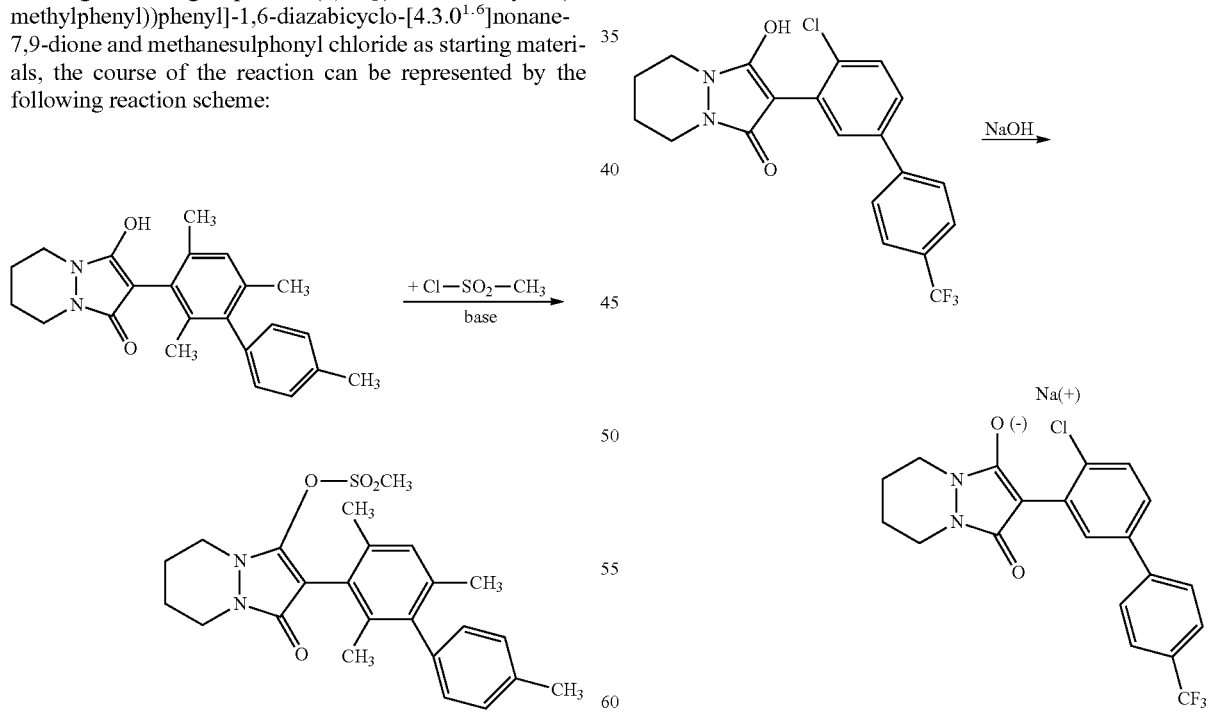

Using, according to process (G) 8-[(6-methyl-3-(4-chlorophenyl)phenyl]-1,6-diazabicyclo-[4.3.0^{1.6}]nonane-7,9-dione and 2,2,2-trifluoroethyl methanethiophosphonyl chloride as starting materials, the course of the reaction can be represented by the following reaction scheme:

Using, according to process (H) 8-[(2-chloro-5-(4-trifluoromethylphenyl))phenyl]-1,6-diaza-bicyclo[4.3.0^{1.6}] nonane-7,9-dione and NaOH as components, the course of the process according to the invention can be represented by the following reaction scheme:

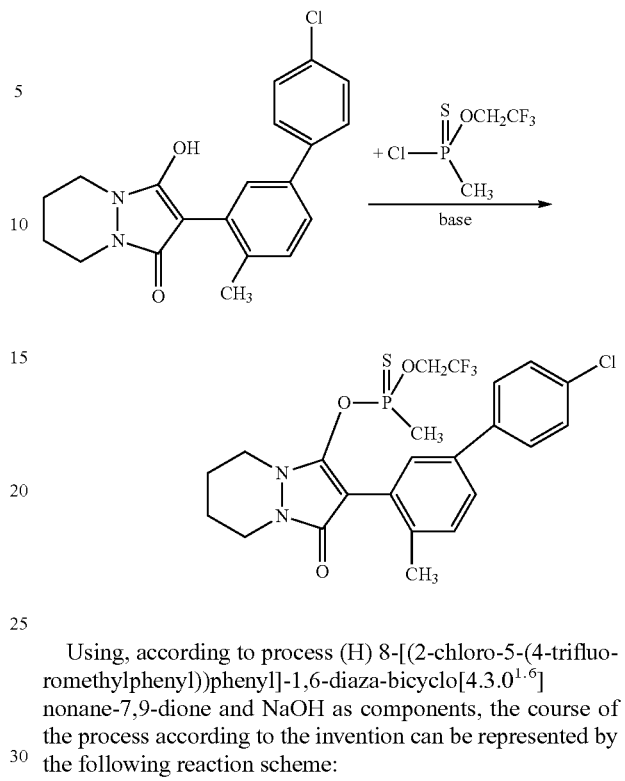

Using, according to process (I) (variant α) 8-[(6-methyl-3-(3-trifluoromethylphenyl))phenyl]-1,6-diazabicyclo [4.3.0^{1.6}]nonane-7,9-dione and ethyl isocyanate as starting materials, the course of the reaction can be represented by the following reaction scheme:

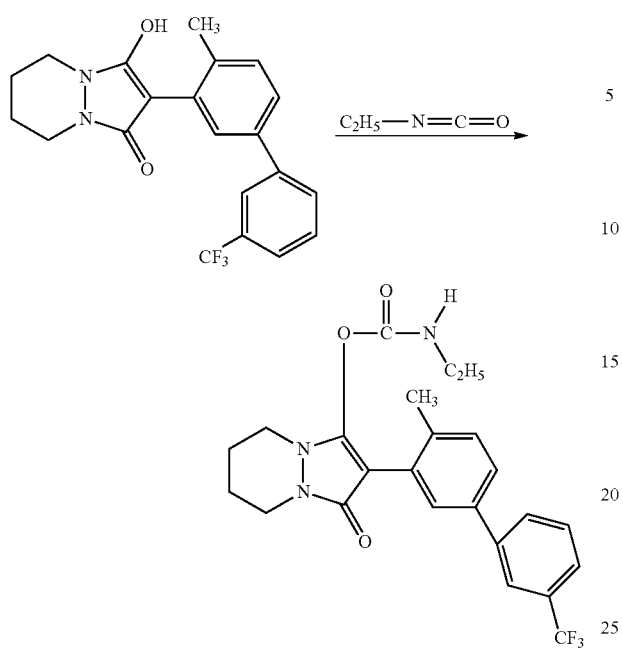

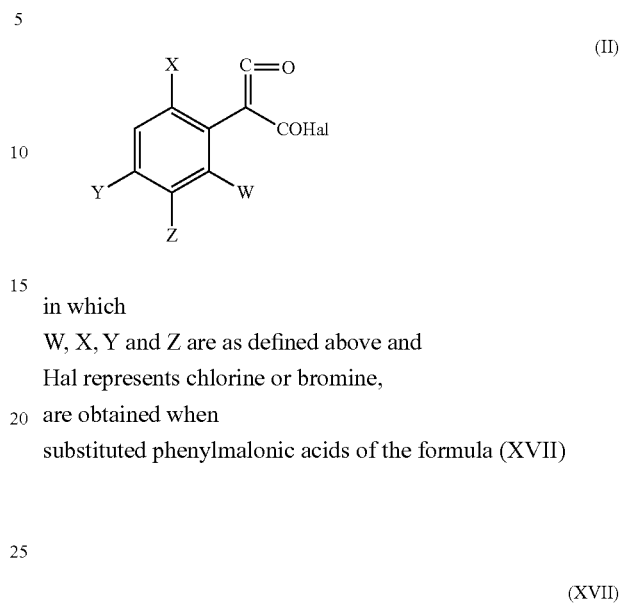

example, Org. Prep. Proced. Int., (4), 155-158, 1975 and DE 1 945 703). Thus, for example, the compounds of the formula (II)

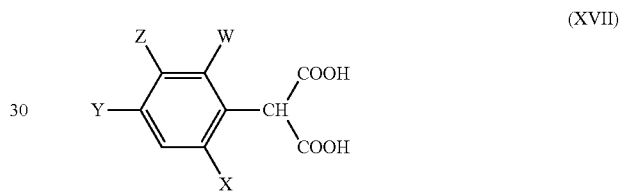

in which

W, X, Y and Z are as defined above and

Hal represents chlorine or bromine, are obtained when substituted phenylmalonic acids of the formula (XVII)

Using, according to process (I) (variant β) 8-[(2-chloro-5-(4-fluorophenyl))phenyl]-1,6-diazabicyclo[4.3.0$^{1.6}$]nonane-7,9-dione and dimethylcarbamoyl chloride as starting materials, the course of the reaction can be represented by the following scheme:

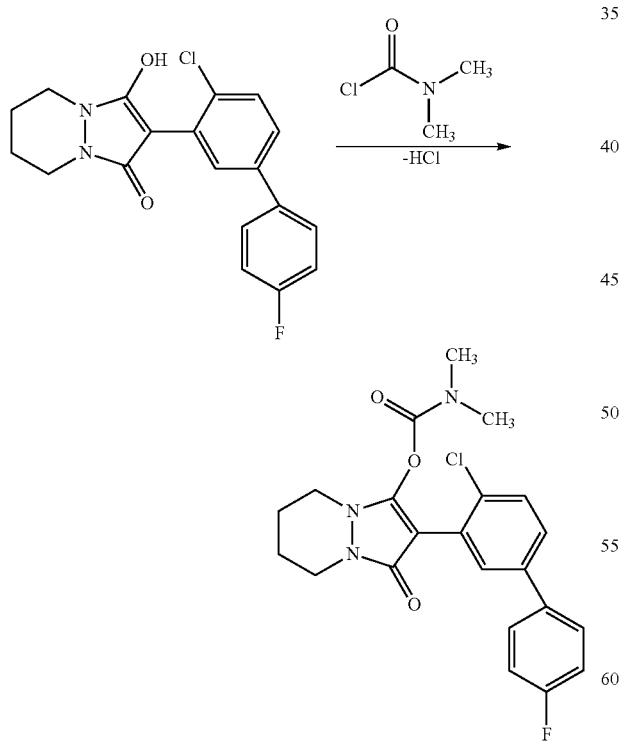

in which

W, X, Y and Z are as defined above, are reacted with acid halides, such as, for example, thionyl chloride, phosphorus(V) chloride, phosphorus(III) chloride, oxalyl chloride, phosgene or thionyl bromide, if appropriate in the presence of a catalyst, such as, for example, dimethylformamide, methylsterylformamide or triphenylphosphine, and if appropriate in the presence of bases, such as, for example, pyridine or triethylamine.

The substituted phenylmalonic acids of the formula (XVII) are novel. They can be prepared in a simple manner by known processes (cf., for example, Organikum, VEB Deutscher Verlag der Wissenschaften, Berlin 1977, p. 517 ff., EP-A-528 156, WO 97/36868, WO 97/01535 and WO 98/05638).

Thus, phenylmalonic acids of the formula (XVII)

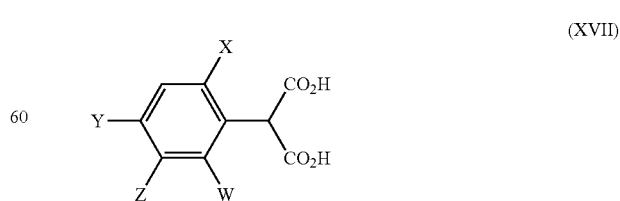

in which

W, X, Y and Z are as defined above,

The halocarbonyl ketenes of the formula (II) required as starting materials for the above process (A) (α) are novel. They can be prepared by methods known in principle (cf., for are obtained when phenylmalonic esters of the formula (III)

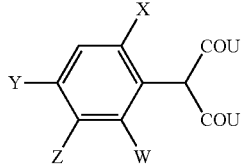
(III)

in which

W, X, Y and Z are as defined above, and

U represents $C_1$-$C_8$-alkoxy are initially hydrolysed in the presence of a base and a solvent and subsequently carefully acidified (EP-528 156, WO 97/36868, WO 97/01535).

The malonic esters of the formula (III)

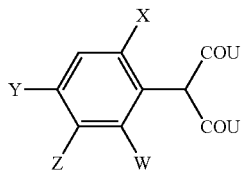
(III)

in which

W, X, Y and Z are as defined above and

U represents $C_1$-$C_8$-alkoxy are novel.

They can be prepared by generally known methods of organic chemistry (cf., for example, Tetrahedron Lett. 27, 2763 (1986) and Organikum, VEB Deutscher Verlag der Wissenschaften, Berlin 1977, p. 587 ff.) and can also be used as starting materials for the process A (β) according to the invention.

Some of the hydrazines, required as starting materials for the processes A (α) and A (β) according to the invention, of the formula (IV)

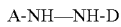 A-NH—NH-D (IV), in which

A and D are as defined above are known, and/or they can be prepared by methods known from the literature (cf., for example, Liebigs Ann. Chem. 585, 6 (1954); Reaktionen der organischen Synthese [Reactions of organic synthesis], C. Ferri, pages 212, 513; Georg Thieme Verlag Stuttgart, 1978; Liebigs Ann. Chem. 443, 242 (1925); Chem. Ber. 98, 2551 (1965), EP-A 508 126, WO 92/16510, WO 99/47525, WO 01/17972).

The compounds, required for the process A (γ) according to the invention, of the formula (V)

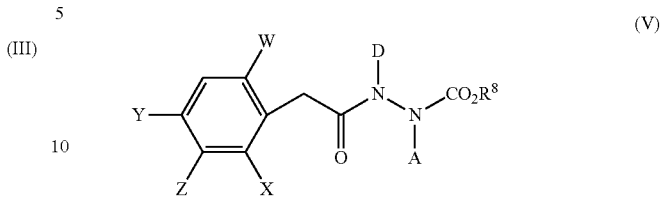
(V)

in which

A, D, W, X, Y, Z and $R^8$ are as defined above are novel.

The acyl carbazates of the formula (V) are obtained, for example, when carbazates of the formula (XVIII)

(XVIII)

in which

A, $R^8$ and D are as defined above are acylated with substituted phenylacetic acid derivatives of the formula (XIX)

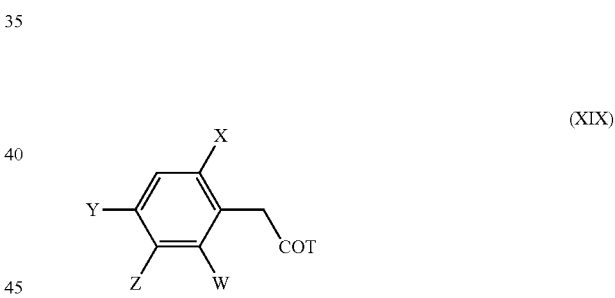
(XIX)

in which

W, X, Y and Z are as defined above,

T represents a leaving group introduced by reagents for activating carboxylic acids, such as carbonyldiimidazole, carbonyldiimides (such as, for example, dicyclohexylcarbodiimide), phosphorylating reagents (such as, for example, $POCl_3$, BOP-Cl), halogenating agents, for example thionyl chloride, oxalyl chloride, phosgene, sulphonyl chlorides (for example toluenesulphonyl chloride) or chloroformic esters, (Chem. Reviews 52, 237-416 (1953); Bhattacharya, Indian J. Chem. 6, 341-5, 1968).

Some of the carbazates of the formula (XVIII) are known compounds, or they can be prepared by processes of organic chemistry which are known in principle.

Some of the compounds of the formula (XIX) are novel, or they can be prepared by processes known in principle, for example WO 99/43649, WO 99/48 869, WO 99/55 673.

The biphenylacetic acids, required for preparing compounds of the formula (XIX), of the formula (XX)

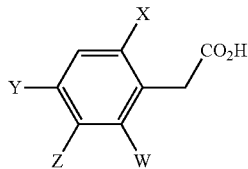
(XX)

in which
W, X and Y are as defined above
are obtained, for example, when biphenylacetic esters of the formula (XXI)

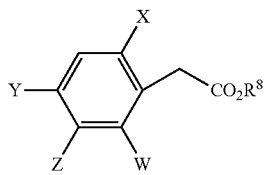
(XXI)

in which
W, X, Y and $R^8$ are as defined above
are hydrolysed in the presence of acids or bases, in the presence of a solvent, under generally known standard conditions.

Some of the compounds of the formulae (XX) and (XXI) are novel and can be prepared analogously to the processes described in WO 99/48869.

The compounds of the formula (XXI)

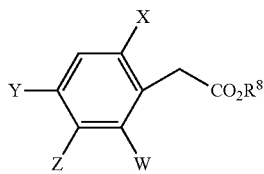
(XXI)

in which
W, X, Y, Z and $R^8$ are as defined above
are obtained, for example, by the process (Q) described in the examples
when phenylacetic esters of the formula (XXI-a)

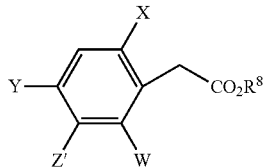
(XXI-a)

in which
$R^8$, W, X and Y are as defined above and
Z' represents halogen (in particular bromine)
are reacted in the presence of a phenylboronic acid of the formula (VI) in which Z is as defined above, in the presence of a base and, if appropriate, in the presence of a catalyst (preferably a palladium salt or palladium complex, such as, for example, tetrakis triphenylphosphine)-palladium(0).

Some of the phenylacetic esters of the formula (XXI-a) are known from the applications WO 97/01 535, WO 97/36 868, WO 98/05 638, or they can be prepared by the processes described therein.

Some of the compounds of the formulae (I'-a) to (I'-g), required as starting materials for the above process (D), in which A, D, W, X and Y are as defined above and Z' represents chlorine or bromine, preferably bromine, are known (WO, 97/01 535, WO 97/36 868, WO 98/05 638, WO 96/35 664, WO 97/02 243 and WO 98/05 638), or they can be prepared according to the processes described therein.

Some of the boronic acids of the formula (VI)

(VI)

in which
Z is as defined above
are commercially available, or they can be prepared in a simple manner by generally known processes.

The acid halides of the formula (VII), carboxylic anhydrides of the formula (VIII), chloroformic esters or chloroformic thioesters of the formula (IX), chloromonothioformic esters or chlorodithioformic esters of the formula (X), sulphonyl chlorides of the formula (XI), phosphorus compounds of the formula (XII) and metal hydroxides, metal alkoxides or amines of the formulae (XIII) and (XIV), respectively, and isocyanates of the formula (XV) and carbamoyl chlorides of the formula (XVI) furthermore required as starting materials for carrying out the processes (C), (D), (E), (F), (G), (H) and (I) according to the invention are generally known compounds of organic or inorganic chemistry.

The process (A-α) according to the invention is characterized in that hydrazines of the formula (IV) or salts of these compounds are reacted with ketene acid halides of the formula (II) in the presence of a diluent and, if appropriate, in the presence of an acid acceptor.

Diluents suitable for use in the process (A-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenylether, moreover polar solvents, such as dimethyl sulphoxide, sulpholane, dimethylformamide or n-methylpyrrolidone.

Suitable for use as acid acceptors for carrying out the process variant (A-α) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (A-α) according to the invention, the reaction temperatures can be varied within a relatively wide range. Expediently, the process is carried out at temperatures between 0° C. and 250° C., preferably between 50° C. and 220° C.

The process (A-α) according to the invention is expediently carried out under atmospheric pressure.

When carrying out the process (A-α) according to the invention, the reaction components of the formulae (III) and (N) in which A, D, W, X, Y and Z are as defined above and Hal represents halogen and, if appropriate, the acid acceptors are generally employed in approximately equimolar amounts. However, it is also possible to use a relatively large excess (up to 5 mol) of one component or the other.

The process (A-β) is characterized in that hydrazines of the formula (IV) or salts of this compound in which A and D are as defined above are, in the presence of a base, subjected to a condensation with malonic esters or malonamides of the formula (III) in which U, W, X, Y and Z are as defined above.

Diluents suitable for use in the process (A-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetrahydrofuran, dioxane, diphenyl ether, glycol dimethyl ether and diglycol dimethyl ether, moreover polar solvents, such as dimethyl sulphoxide, sulpholane, dimethylformamide, dimethyl-acetamide and n-methylpyrrolidone, and also alcohols, such as methanol, ethanol, propanol, iso-propanol, butanol, isobutanol and tert-butanol.

Suitable bases (deprotonating agents) for carrying out the process (A-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltri($C_8$-$C_{10}$-alkyl)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

It is also possible to employ tertiary amines, such as triethylamine, pyridine, diazabicyclooctane (DABCO), diazabicycloundecane (DBU), diazabicyclononene (DBN), Hünig base and N,N-dimethylaniline.

When carrying out the process (A-β) according to the invention, the reaction temperatures can be varied within a relatively wide range. In general, the reaction is carried out at temperatures between 0° C. and 280° C., preferably between 50° C. and 180° C.

The process (A-β) according to the invention is generally carried out under atmospheric pressure.

When carrying out the process (A-β) according to the invention, the reaction components of the formulae (III) and (IV) are generally employed in approximately equimolar amounts. However, it is also possible to use a relatively large excess (up to 3 mol) of one component or the other.

The process (A-γ) is characterized in that compounds of the formula (V) in which A, D, W, X, Y, Z and $R^8$ are as defined above and are subjected to an intramolecular condensation in the presence of a base.

Diluents suitable for use in the process (A-γ) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 methyltri($C_8$-$C_{10}$-alkyl)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and moreover also alkali metal alkoxides, such as sodium methoxide, sodium ethoxide and potassium tert-butoxide.

When carrying out the process (A-γ) according to the invention, the reaction temperatures can be varied within a relatively wide range. In general, the reaction is carried out at temperatures between 0° C. and 250° C., preferably between 50° C. and 150° C.

The process (A-γ) according to the invention is generally carried out under atmospheric pressure.

When carrying out the process (A-γ) according to the invention, the reaction components of the formula (V) and the deprotonating bases are generally employed in approximately doubly equimolar amounts. However, it is also possible to use a relatively large excess (up to 3 mol) of one component or the other.

Suitable catalysts for carrying out the process (B) according to the invention are palladium(0) complexes. Preference is given, for example, to tetrakis(triphenylphosphine)palladium. If appropriate, it may also be possible to use palladium (II) compounds, for example $PdCl_2$.

Suitable acid acceptors for carrying out the process (B) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate, caesium carbonate or ammonium carbonate, sodium bicarbonate or potassium bicarbonate, alkali metal fluorides, such as, for example, caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclo-nonene (DBN) or diazabicycloundecene (DBU).

Suitable diluents for carrying out the process (B) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or i-propanol, n-, iso-, sec- or tert-butanol, ethanediol, propane-1,2-diol, ethoxyethanol, methoxyethanol, diethylene glycol monomethyl ether, diethylene glycol monomethyl ether; water.

The reaction temperature in the process (B) according to the invention can varied within a relatively wide range. In general, the reaction is carried out at temperatures between 0° C. and +140° C., preferably between 50° C. and +100° C.

When carrying out the process (B) according to the invention, the boronic acid of the formula (VI) in which Z is as defined above and the compounds of the formulae (I'-a) to (I'-g) in which A, D, W, X, Y and Z' are as defined above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I'-a) to (I'-g). The base is generally employed in excess.

The process (E-α) is characterized in that compounds of the formula (Ia) are in each case reacted with carbonyl halides of the formula (VII), if appropriate in the presence of a diluent and if appropriate in the presence of an acid binder.

Diluents suitable for use in the process (C-α) according to the invention are all solvents which are inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction according to the process (C-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (C-α) according to the invention can be varied within a relatively wide range. In general, the reaction is carried out at temperatures between –20° C. and +150° C., preferably between 0° C. and 100° C.

When carrying out the process (C-α) according to the invention, the starting materials of the formula (I-a) and the carbonyl halide of the formula (VII) are generally each used in approximately equivalent amounts. However, it is also possible to use a relatively large excess (up to 5 mol) of the carbonyl halide. Work-up is carried out by customary methods.

The process (C-β) is characterized in that compounds of the formula (Ia) are reacted with carboxylic anhydrides of the formula (VIII), if appropriate in the presence of a diluent and if appropriate in the presence of an acid binder.

Diluents suitable for use in the process (C-β) according to the invention are preferably those diluents which are also preferred when using acid halides. Furthermore, excess carboxylic anhydride may simultaneously act as diluent.

The acid binders which are added, if appropriate, in the process (C-β) are preferably those acid binders which are also preferred when using acid halides.

The reaction temperatures in the process (C-β) according to the invention can be varied within a relatively wide range. In general, the reaction is carried out at temperatures between –20° C. and +150° C., preferably between 0° C. and 100° C.

When carrying out the process (C-β) according to the invention, the starting materials of the formula (Ia) and the carboxylic anhydride of the formula (VIII) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formula (Ia) are in each case reacted with chloroformic esters or chloroformic thioesters of the formula (IX), if appropriate in the presence of a diluent and if appropriate in the presence of an acid binder.

Acid binders suitable for the reaction according to the process (D) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (D) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate and also strongly polar solvents, such as dimethyl sulphoxide and sulpholane.

When carrying out the process (D) according to the invention, the reaction temperatures can be varied within a relatively wide range. If the reaction is carried out in the presence of a diluent and an acid binder, the reaction temperatures are generally between –20° C. and +100° C., preferably between 0° C. and 50° C.

The process (D) according to the invention is generally carried out under atmospheric pressure.

When carrying out the process (D) according to the invention, the starting materials of the formula (I-a) and the appropriate chloroformic ester or chloroformic thioester of the formula (IX) are generally each employed in approximately equivalent amounts. However, it is also possible to use a relatively large excess (up to 2 mol) of one or the other components. Work-up is carried out by customary methods. In general, precipitated salts are removed and the reaction mixture that remains is concentrated by removing the diluent under reduced pressure.

The process (E) according to the invention is characterized in that compounds of the formula (I-a) are in each case reacted with compounds of the formula (X), in the presence of a diluent and, if appropriate, in the presence of an acid binder.

In Preparation Process (E), about 1 mol of chloromonothioformic ester or chlorodithioformic ester of the formula (X) is reacted per mole of starting material of the formula (I-a), at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-a) is prepared by adding strong deprotonating agents, such as, for example, sodium hydride or potassium tert-butoxide, the further addition of acid binders may be dispensed with.

If acid binders are used, these may be customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (F) according to the invention is characterized in that compounds of the formula (I-a) are in each case reacted with sulphonyl chlorides of the formula (XI), if appropriate in the presence of a diluent and if appropriate in the presence of an acid binder.

In Preparation Process (F), about 1 mol of sulphonyl chloride of the formula (XI) is reacted per mole of starting material of the formula (I-a), at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-a) is prepared by adding strong deprotonating agents (such as, for example, sodium hydride or potassium tert-butoxide), the further addition of acid binders may be dispensed with.

If acid binders are used, these may be customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (G) is characterized in that compounds of the formula (I-a) are in each case reacted with phosphorus compounds of the formula (XII), if appropriate in the presence of a diluent and if appropriate in the presence of an acid binder.

In Preparation Process (G), to obtain compounds of the formula (I-e), from 1 to 2, preferably from 1 to 1.3, mol of the phosphorus compound of the formula (XII) are reacted per mole of the compounds (Ia), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Examples which may be mentioned are sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods of organic chemistry. The purification of the end products obtained is preferably by crystallization, chromatographic purification or by "incipient distillation", i.e. removal of the volatile components under reduced pressure.

The process (H) is characterized in that compounds of the formula (I-a) are reacted with metal hydroxides or metal alkoxides of the formula (XIII) or amines of the formula (XIV), if appropriate in the presence of a diluent.

Diluents suitable for use in the process (H) according to the invention are, preferably, ethers, such as tetrahydrofuran, dioxane, diethyl ether; or else alcohols, such as methanol, ethanol, isopropanol, and also water.

The process (H) according to the invention is generally carried out under atmospheric pressure.

The reaction temperatures are generally between −20° C. and 100° C., preferably between 0° C. and 50° C.

The process (I) according to the invention is characterized in that compounds of the formula (I-a) are in each case reacted with (I-α) compounds of the formula (XV), if appropriate in the presence of a diluent and if appropriate in the presence of a catalyst, or (I-β) with compounds of the formula (XVI), if appropriate in the presence of a diluent and if appropriate in the presence of an acid binder.

In Preparation Process (I-α), about 1 mol of isocyanate of the formula (XV) is reacted per mole of starting material of the formula (I-a), at from 0 to 100° C., preferably from 20 to 50° C.

Suitable diluents which are added, if appropriate, are all inert organic solvents, such as ethers, amides, nitriles, sulphones, sulphoxides.

If appropriate, catalysts may be added to accelerate the reaction. Suitable for use as catalysts are, very advantageously, organotin compounds, such as, for example, dibutyltin dilaurate. The reaction is preferably carried out under atmospheric pressure.

In Preparation Process (I-β), about 1 mol of carbamoyl chloride of the formula (XVI) is reacted per mole of starting material of the formula (I-a), at from −20 to 150° C., preferably from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compounds (I-a) is prepared by adding strong deprotonating agents (such as, for example, sodium hydride or potassium tert-butoxide), the further addition of acid binders may be dispensed with.

If acid binders are used, these may be customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The active compounds are well tolerated by plants, have favourable homotherm toxicity and are environmentally friendly; they are suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* Spp.

If appropriate, the compounds according to the invention may also be used in certain concentrations or application rates to act as herbicides and microbicides, for example as fungicides, antimycotics and bactericides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on injecting and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used, as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as mixing partners are, for example, the following:
Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro-[4.5]decane-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap; benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hyprorene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metamsodium, methacrifos, methamidophos, *Metharhizium anisopliae, Metharhizium flavoviride*, methidathion, methiocarb, methomyl, methoprene, methoxychlor, methoxyfenozide, metafluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion, (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium sleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbo-nitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

When used as insecticides in their commercially available formulations and in the use forms prepared with these formulations, the active compounds according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared with these formulations, the active compounds according to the invention can furthermore be present in the form of a mixture with inhibitors which reduce the degradation of the active compound after application in the habitat of the plant, on the surface of parts of plants or in plant tissues.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound is distinguished by excellent residual action on wood and clay as well as good stability to alkali on limed substrates.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes and slugs and snails, owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds, according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp.; *Triatoma* spp., *Rhodnius* spp. and *Panstrongylus* spp.

From the order of the Blattarida, for example, *Blatta orientalis*, *Periplaneta americana*, *Blattela germanica* and *Supella* spp.

From the sub-class of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the Veterinary sector, the active compounds according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds according to the invention have a potent insecticidal action against insects which destroy industrial materials.

The following insects may be mentioned by way of example and as being preferred, but without any limitation:

Beetles, such as
*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as
*Sirex juvencus, Urocerus gigas, Urocerus gigas taignus, Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent;

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced or an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural, and/or synthetic resin.

The synthetic resin used, as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid and triflumuron, chlothiamidin, spinosad, tefluthrin, and fungicides, such as epoxyconazole, hexaconazole, azaconazole, propiconazole, tebuconazole, cyproconazole, metconazole, imazalil, dichlofluanid, tolylfluanid, 3-iodo-2-propynylbutyl carbamate, N-octyl-isothiazolin-3-one and 4,5-dichloro-N-octylisothiazolin-3-one.

The compounds according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algaecides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb; Fe chelates;
or conventional antifouling active compounds such as
4,5-dichloro-2-octyl-4-isothiazolin-3-one, diiodomethylparatryl sulphone, 2-(N,N-dimethyl-thiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used, for example, in the following plants:
Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsala, Senecio, Sesbania, Sida, Sinapis, Solanum, Sonchus, Sphenoclea, Stellaria, Taraxacum, Thlaspi, Trifolium, Urtica, Veronica, Viola, Xanthium.*
Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*
Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*
Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (—P), diclofop (-methyl), diclosulam, diethatyl(-ethyl), difenzoquat, diflufenican, diflu-fenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxa-prop (—P-ethyl), fentrazamide, flamprop (-isopropyl, -isopropyl-L, -methyl), flazasulfuron, flora-sulam, fluazifop (—P-butyl), fluazolate, flucarbazone (-sodium), flufenacet, flumetsulam, flumi-clorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop. (-ethoxyethyl, —P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pent-oxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), quinchlorac, quinmerac, quinoclamine, quizalofop (—P-ethyl, —P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Also suitable for the mixtures are known safeners, for example:
AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (—P), mefenpyr (-diethyl), MG-191, oxabetrinil, PPG-1292, R-29148.

A mixture with other known active compounds, such as fungicides, insectides, acaricides, nematicides, bird repellents, plant nutrients and soil conditioners, is also possible.

The active compounds can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The substances according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:
*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora;*
*Pythium* species, such as, for example, *Pythium ultimum;*
*Phytophthora* species, such as, for example, *Phytophthora infestans;*
*Pseudoperonospora* species, such as, for example, *Pseudoperonospora humuli* or *Pseudoperonospora cubensis;*
*Plasmopara* species, such as, for example, *Plasmopara viticola;*
*Bremia* species, such as, for example, *Bremia lactucae;*
*Peronospora* species, such as, for example, *Peronospora pisi* or *P. brassicae;*
*Erysiphe* species, such as, for example, *Erysiphe graminis;*
*Sphaerotheca* species, such as, for example, *Sphaerotheca fuliginea;*
*Podosphaera* species, such as, for example, *Podosphaera leucotricha;*
*Venturia* species, such as, for example, *Venturia inaequalis;*
*Pyrenophora* species, such as, for example, *Pyrenophora teres* or *P. graminea*
(conidia form: *Drechslera*, syn: *Helminthosporium*);
*Cochliobolus* species, such as, for example, *Cochliobolus sativus*
(conidia form: *Drechslera*, syn: *Helminthosporium*);
*Uromyces* species, such as, for example, *Uromyces appendiculatus;*

*Puccinia* species, such as, for example, *Puccinia recondita;*
*Sclerotinia* species, such as, for example, *Sclerotinia sclerotiorum;*
*Tilletia* species, such as, for example, *Tilletia caries;*
*Ustilago* species, such as, for example, *Ustilago nuda* or *Ustilago avenae;*
*Pellicularia* species, such as, for example, *Pellicularia sasakii;*
*Pyricularia* species, such as, for example, *Pyricularia oryzae;*
*Fusarium* species, such as, for example, *Fusarium culmorum;*
*Botrytis* species, such as, for example, *Botrytis cinerea;*
*Septoria* species, such as, for example, *Septoria nodorum;*
*Leptosphaeria* species, such as, for example, *Leptosphaeria nodorum;*
*Cercospora* species, such as, for example, *Cercospora canescens;*
*Alternaria* species, such as, for example, *Alternaria brassicae;* and
*Pseudocercosporella* species, such as, for example, *Pseudocercosporella herpotrichoides.*

The active compounds according to the invention also have very good fortifying action in plants. Accordingly, they can be used for mobilizing the defenses of the plant against attack by unwanted microorganisms.

In the present context, plant-fortifying (resistance-inducing) substances are to be understood as meaning those substances which are capable of stimulating the defense system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can if appropriate also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:
2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cyrnoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris (albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl) amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1, 2,4-triazol-1-yl)cycloheptanol; methyl 1-(2,3-dihydro-2, 2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro-[4.5]decane-3-amine; sodium tetrathiocarbonate;

and copper salts and preparations, such as Bordeaux mixture; copper hydroxide; copper naphthenate; copper oxychloride; copper sulphate; cufraneb; cuprous oxide; mancopper; oxine-copper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butyl-pyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans-isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*,

WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbo-nitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes,*

*Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The preparation and the use of the active compounds according to the invention are illustrated by the examples below.

PREPARATION EXAMPLES

Example (I-1-a-1)

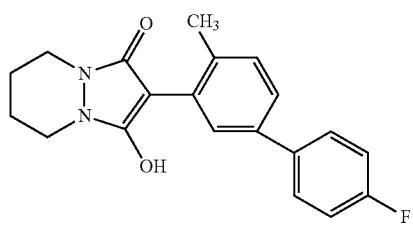

3.1 g (8.0 mmol) of the compound of Example V-1 are dissolved in 40 ml of anhydrous dimethylformamide (DMF) and, at 10° C., 1.08 g (9.6 mmol) of potassium tert-butoxide are added under argon. The mixture is stirred at room temperature for 12 h, the solvent is removed under reduced pressure and the residue is taken up in 150 ml of 10% aqueous sodium hydroxide solution. The mixture is extracted 3× with methylene chloride and the aqueous phase is, with ice bath cooling, acidified with 2N hydrochloric acid. The acidic solution is extracted 3× with methylene chloride and the combined organic phases are washed 1× with water and then dried over sodium sulphate. The solvent is removed under reduced pressure and the residue is then crystallized with ether, filtered off under suction and air-dried.

Yield: 2.3 g (85% of theory); colourless solid; temperature: 172° C.

The following compounds of the formula (I-1-a) were prepared analogously to Example (I-1-a-1) and in accordance with the general instructions for preparing compounds of the formula (I):

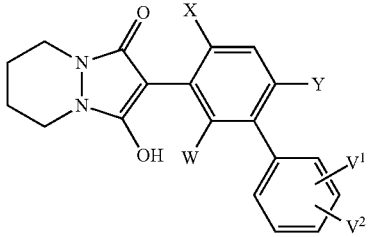

(I-1-a)

| Ex. No. | W | X | Y | V¹/V² | m.p. (° C.) |
|---|---|---|---|---|---|
| I-1-a-2 | H | CH$_3$ | H | 2-Cl | 253 |
| I-1-a-3 | H | CH$_3$ | H | 3-Cl | 177 |
| I-1-a-4 | H | CH$_3$ | H | 4-Cl | 206 |
| I-1-a-5 | H | CH$_3$ | H | 2-F | 195 |
| I-1-a-6 | H | CH$_3$ | H | 3-F | 161 |
| I-1-a-1 | H | CH$_3$ | H | 4-F | 172 |
| I-1-a-7 | H | CH$_3$ | H | 2-CH$_3$ | 153 |
| I-1-a-8 | H | CH$_3$ | H | 3-CH$_3$ | 173 |
| I-1-a-9 | H | CH$_3$ | H | 4-CH$_3$ | 168 |
| I-1-a-10 | H | CH$_3$ | H | 2,3-Cl$_2$ | 207 |
| I-1-a-11 | H | CH$_3$ | H | 2,4-Cl$_2$ | 161 |
| I-1-a-12 | H | CH$_3$ | H | 2,5-Cl$_2$ | 150 |
| I-1-a-13 | H | CH$_3$ | H | 3,4-Cl$_2$ | 207 |
| I-1-a-14 | H | CH$_3$ | H | 3,5-Cl$_2$ | 196 |
| I-1-a-15 | H | CH$_3$ | H | 2,4-F$_2$ | 173 |
| I-1-a-16 | H | CH$_3$ | H | 2,5-F$_2$ | 197 |
| I-1-a-17 | H | CH$_3$ | H | 3-Cl, 4-F | 192 |
| I-1-a-18 | H | CH$_3$ | H | 2-CF$_3$ | 142 |
| I-1-a-19 | H | CH$_3$ | H | 3-CF$_3$ | 185 |
| I-1-a-20 | H | CH$_3$ | H | 4-CF$_3$ | 224 |
| I-1-a-21 | H | CH$_3$ | H | 2-OCH$_3$ | 185 |
| I-1-a-22 | H | CH$_3$ | H | 3-OCH$_3$ | 135 |
| I-1-a-23 | H | CH$_3$ | H | 4-OCH$_3$ | 156 |
| I-1-a-24 | H | CH$_3$ | H | 3-SO$_2$C$_2$H$_5$ | 202 |
| I-1-a-25 | H | CH$_3$ | H | 4-SO$_2$C$_2$H$_5$ | 197 |
| I-1-a-26 | H | CH$_3$ | H | 3-NO$_2$ | 202 |
| I-1-a-27 | H | CH$_3$ | H | 4-OCF$_3$ | 151 |
| I-1-a-28 | H | CH$_3$ | H | 4-OPh | 204 |
| I-1-a-29 | H | CH$_3$ | H | 4-SCH$_3$ | 156 |
| I-1-a-30 | H | CH$_3$ | H | 4-i-C$_3$H$_7$ | 142 |
| I-1-a-31 | H | CH$_3$ | H | 3,5-(CF$_3$)$_2$ | 254 |
| I-1-a-32 | CH$_3$ | CH$_3$ | CH$_3$ | 4-F | oil |
| I-1-a-33 | H | CH$_3$ | CH$_3$ | 4-Cl | 101 |
| I-1-a-34 | CH$_3$ | CH$_3$ | H | 4-F | 246 |
| I-1-a-35 | CH$_3$ | CH$_3$ | H | 4-Cl | 240 |
| I-1-a-36 | CH$_3$ | CH$_3$ | CH$_3$ | 4-Cl | >250 |
| I-1-a-37 | H | Cl | H | 4-CF$_3$ | 257 |
| I-1-a-38 | H | Cl | H | 4-Cl | 229 |
| I-1-a-39 | H | Cl | H | 4-F | 187 |
| I-1-a-40 | H | Cl | H | 3,4-Cl$_2$ | 201 |
| I-1-a-41 | H | Cl | H | 2,4-Cl$_2$ | 184 |
| I-1-a-42 | H | Cl | H | 2,4-F$_2$ | 200 |
| I-1-a-43 | H | Cl | H | 3,5-Cl$_2$ | 256 |
| I-1-a-44 | H | Cl | H | 4-F, 3-Cl | 228 |
| I-1-a-45 | H | Cl | H | 2,5-Cl$_2$ | 177 |

The following compounds of the formula (I-2-a) were prepared analogously to Example (I-1-a-1) and in accordance with the general instructions for preparing compounds of the formula (I):

(I-2-a)

| Ex. No. | W | X | Y | V¹/V² | m.p. (° C.) |
|---|---|---|---|---|---|
| I-2-a-1 | H | CH$_3$ | H | 2-Cl | 204 |
| I-2-a-2 | H | CH$_3$ | H | 3-Cl | 167 |
| I-2-a-3 | H | CH$_3$ | H | 4-Cl | 207 |
| I-2-a-4 | H | CH$_3$ | H | 2-F | 179 |
| I-2-a-5 | H | CH$_3$ | H | 3-F | 175 |
| I-2-a-6 | H | CH$_3$ | H | 4-F | 188 |

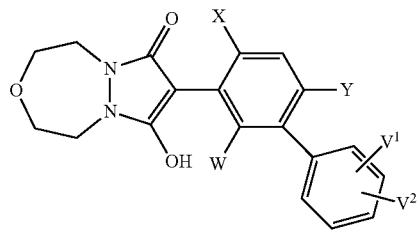

(I-2-a)

| Ex. No. | W | X | Y | V¹/V² | m.p. (° C.) |
|---|---|---|---|---|---|
| I-2-a-7 | H | $CH_3$ | H | 2-$CH_3$ | 172 |
| I-2-a-8 | H | $CH_3$ | H | 3-$CH_3$ | 175 |
| I-2-a-9 | H | $CH_3$ | H | 4-$CH_3$ | 176 |
| I-2-a-10 | H | $CH_3$ | H | 2,3-$Cl_2$ | 192 |
| I-2-a-11 | H | $CH_3$ | H | 2,4-$Cl_2$ | 176 |
| I-2-a-12 | H | $CH_3$ | H | 2,5-$Cl_2$ | 149 |
| I-2-a-13 | H | $CH_3$ | H | 3,4-$Cl_2$ | 191 |
| I-2-a-14 | H | $CH_3$ | H | 3,5-$Cl_2$ | 187 |
| I-2-a-15 | H | $CH_3$ | H | 2,4-$F_2$ | 191 |
| I-2-a-16 | H | $CH_3$ | H | 2,5-$F_2$ | 182 |
| I-2-a-17 | H | $CH_3$ | H | 3-Cl, 4-F | 201 |
| I-2-a-18 | H | $CH_3$ | H | 2-$CF_3$ | 142 |
| I-2-a-19 | H | $CH_3$ | H | 3-$CF_3$ | 180 |
| I-2-a-20 | H | $CH_3$ | H | 4-$CF_3$ | 221 |
| I-2-a-21 | H | $CH_3$ | H | 2-$OCH_3$ | 158 |
| I-2-a-22 | H | $CH_3$ | H | 3-$OCH_3$ | 158 |
| I-2-a-23 | H | $CH_3$ | H | 4-$OCH_3$ | 186 |
| I-2-a-24 | H | $CH_3$ | H | 3-$SO_2C_2H_5$ | 189 |
| I-2-a-25 | H | $CH_3$ | H | 4-$SO_2C_2H_5$ | 226 |
| I-2-a-26 | H | $CH_3$ | H | 3-$NO_2$ | 205 |
| I-2-a-27 | H | $CH_3$ | H | 4-$OCF_3$ | 198 |
| I-2-a-28 | H | $CH_3$ | H | 4-OPh | 226 |
| I-2-a-29 | H | $CH_3$ | H | 4-$SCH_3$ | 176 |
| I-2-a-30 | H | $CH_3$ | H | 4-i-$C_3H_7$ | 170 |
| I-2-a-31 | H | $CH_3$ | H | 3,5-$(CF_3)_2$ | 223 |
| I-2-a-32 | $CH_3$ | $CH_3$ | $CH_3$ | 4-F | oil |
| I-2-a-33 | H | $CH_3$ | $CH_3$ | 4-Cl | 185 |
| I-2-a-34 | $CH_3$ | $CH_3$ | H | 4-F | 213 |
| I-2-a-35 | $CH_3$ | $CH_3$ | H | 4-Cl | 255 |
| I-2-a-36 | $CH_3$ | $CH_3$ | $CH_3$ | 4-Cl | 244 |
| I-2-a-37 | H | Cl | H | 4-$CF_3$ | 251 |
| I-2-a-38 | H | Cl | H | 4-Cl | 227 |
| I-2-a-39 | H | Cl | H | 4-F | 186 |
| I-2-a-40 | H | Cl | H | 2,4-$Cl_2$ | 192 |
| I-2-a-41 | H | Cl | H | 3,4-$Cl_2$ | 234 |
| I-2-a-42 | H | Cl | H | 2,4-$F_2$ | 227 |
| I-2-a-43 | H | Cl | H | 3,5-$Cl_2$ | 253 |
| I-2-a-44 | H | Cl | H | 4-F, 3-Cl | 234 |
| I-2-a-45 | H | Cl | H | 2,5-$Cl_2$ | 198 |

The following compounds of the formula (I-3-a) were prepared analogously to Example (I-1-a-1) and in accordance with the general instructions for preparing compounds of the formula (I):

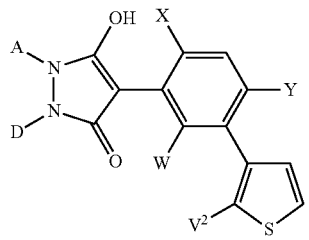

(I-3-a)

| Ex. No. | W | X | Y | V² | A | D | m.p. ° C. |
|---|---|---|---|---|---|---|---|
| I-3-a-1 | H | $CH_3$ | H | H | | —$(CH_2)_4$— | 162 |
| I-3-a-2 | H | $CH_3$ | H | H | | —$(CH_2)_2$—O—$(CH_2)_2$— | 173 |

The following compounds of the formula (I-4-a) were prepared analogously to Example (I-1-a-1) and in accordance with the general instructions for preparing compounds of the formula (I):

(I-4-a)

| Ex. No. | W | X | Y | V¹/V² | m.p. ° C. |
|---|---|---|---|---|---|
| I-4-a-1 | H | $CH_3$ | H | 4-F | 151 |

The following compounds of the formula (I-5-a) were prepared analogously to Example (I-1-a-1) and in accordance with the general instructions for preparing compounds of the formula (I):

(I-5-a)

| Ex. No. | W | X | Y | V¹/V² | m.p. ° C. |
|---|---|---|---|---|---|
| I-5-a-1 | H | $CH_3$ | H | 4-F | 184 |
| I-5-a-2 | H | $CH_3$ | H | 4-Cl | 33 |
| I-5-a-3 | H | Cl | H | 4-F | 219 |
| I-4-a-4 | H | Cl | H | 4-Cl | 220 |

The following compounds of the formula (I-6-a) were prepared analogously to Example (I-1-a-1) and in accordance with the general instructions for preparing compounds of the formula (I):

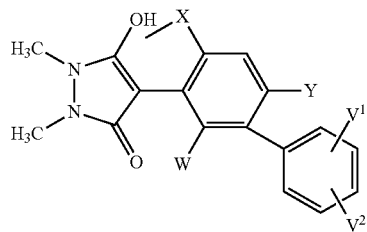

(I-6-a)

| Ex. No. | W | X | Y | V¹/V² | m.p. ° C. |
|---|---|---|---|---|---|
| I-6-a-1 | H | CH₃ | H | 4-F | 164 |
| I-6-a-2 | H | CH₃ | H | 4-Cl | 130 |
| I-6-a-3 | H | Cl | H | 4-Cl | 156 |
| I-6-a-4 | H | Cl | H | 4-F | 161 |

The following compounds of the formula (I-7-a) were prepared analogously to Example (I-1-a-1) and in accordance with the general instructions for preparing compounds of the formula (I):

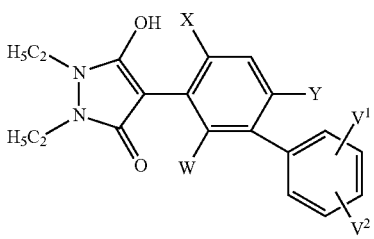

(I-7-a)

| Ex. No. | W | X | Y | V¹/V² | m.p. ° C. |
|---|---|---|---|---|---|
| I-7-a-1 | H | CH₃ | H | 4-F | 150 |
| I-7-a-2 | H | CH₃ | H | 4-Cl | 160 |
| I-7-a-3 | H | Cl | H | 4-F | 166 |
| I-7-a-4 | H | Cl | H | 4-Cl | 139 |

The following compounds of the formula (I-8-a) were prepared analogously to Example (I-1-a-1) and in accordance with the general instructions for preparing compounds of the formula (I):

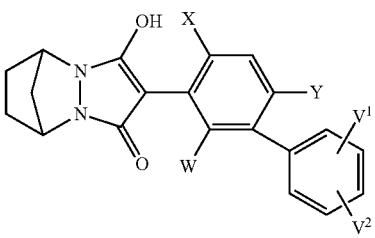

(I-8-a)

| Ex. No. | W | X | Y | V¹/V² | m.p. ° C. |
|---|---|---|---|---|---|
| I-8-a-1 | H | CH₃ | H | 4-Cl | 210 |
| I-8-a-2 | H | Cl | H | 4-Cl | 130 |

Example I-1-b-1

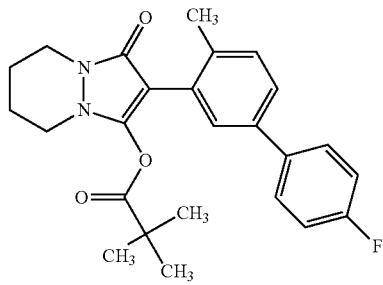

At room temperature, triethylamide (0.17 g; 1.63 mmol) and a solution of trimethylacetyl chloride (0.2 g; 1.63 mmol) in methylene chloride (10 ml) are added successively to a solution of 0.5 g (1.48 mmol) of the compound of Example I-1-a-1 in 20 ml of methylene chloride. After 12 h of stirring at room temperature, the mixture is diluted with 100 ml of methylene chloride and washed in each case 1× with 10% strength citric acid and 10% strength aqueous sodium hydroxide solution. The organic phase is dried over sodium sulphate, the solvent is removed under reduced pressure and the residue is crystallized with petroleum ether, filtered off with suction and air-dried.

Yield: 0.35 g (56% of theory); colourless solid; m.p. 188° C.

The following compounds of the formula (I-1-b) are obtained analogously to Example (I-1-b-1) and in accordance with the general instructions for preparing compounds of the formula (I-b)

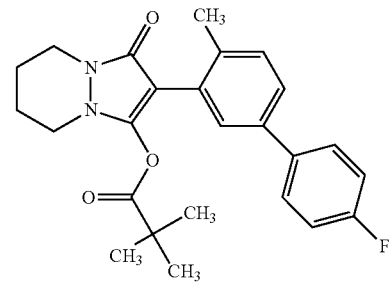

(I-1-b)

| Ex. No. | W | X | Y | V¹/V² | R¹ | m.p. (° C.) |
|---|---|---|---|---|---|---|
| I-1-b-2 | H | CH₃ | H. | 2-Cl | t-C₄H₉ | oil |
| I-1-b-3 | H | CH₃ | H | 3-Cl | t-C₄H₉ | oil |
| I-1-b-4 | H | CH₃ | H | 4-Cl | t-C₄H₉ | oil |
| I-1-b-5 | H | CH₃ | H | 2-F | t-C₄H₉ | oil |
| I-1-b-6 | H | CH₃ | H | 3-F | t-C₄H₉ | oil |
| I-1-b-1 | H | CH₃ | H | 4-F | t-C₄H₉ | 188 |
| I-1-b-7 | H | CH₃ | H | 2-CH₃ | t-C₄H₉ | oil |
| I-1-b-8 | H | CH₃ | H | 3-CH₃ | t-C₄H₉ | oil |
| I-1-b-9 | H | CH₃ | H | 4-CH₃ | t-C₄H₉ | oil |
| I-1-b-10 | H | CH₃ | H | 2,3-Cl₂ | t-C₄H₉ | oil |
| I-1-b-11 | H | CH₃ | H | 2,4-Cl₂ | t-C₄H₉ | oil |
| I-1-b-12 | H | CH₃ | H | 2,5-Cl₂ | t-C₄H₉ | oil |
| I-1-b-13 | H | CH₃ | H | 3,4-Cl₂ | t-C₄H₉ | oil |
| I-1-b-14 | H | CH₃ | H | 3,5-Cl₂ | t-C₄H₉ | oil |
| I-1-b-15 | H | CH₃ | H | 2,4-F₂ | t-C₄H₉ | 187 |
| I-1-b-16 | H | CH₃ | H | 2,5-F₂ | t-C₄H₉ | oil |
| I-1-b-17 | H | CH₃ | H | 3-Cl, 4-F | t-C₄H₉ | oil |
| I-1-b-18 | H | CH₃ | H | 2-CF₃ | t-C₄H₉ | oil |
| I-1-b-19 | H | CH₃ | H | 3-CF₃ | t-C₄H₉ | oil |
| I-1-b-20 | H | CH₃ | H | 4-CF₃ | t-C₄H₉ | 175 |
| I-1-b-21 | H | CH₃ | H | 2-OCH₃ | t-C₄H₉ | oil |

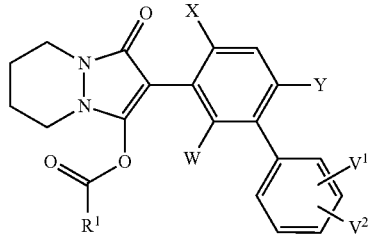

(I-1-b)

| Ex. No. | W | X | Y | V¹/V² | R¹ | m.p. (° C.) |
|---|---|---|---|---|---|---|
| I-1-b-22 | H | CH₃ | H | 3-OCH₃ | t-C₄H₉ | oil |
| I-1-b-23 | H | CH₃ | H | 4-OCH₃ | t-C₄H₉ | oil |
| I-1-b-24 | H | CH₃ | H | 3-SO₂C₂H₅ | t-C₄H₉ | oil |
| I-1-b-25 | H | CH₃ | H | 4-SO₂C₂H₅ | t-C₄H₉ | oil |
| I-1-b-26 | H | CH₃ | H | 3-NO₂ | t-C₄H₉ | oil |
| I-1-b-27 | H | CH₃ | H | 4-OCF₃ | t-C₄H₉ | oil |
| I-1-b-28 | H | CH₃ | H | 4-OPh | t-C₄H₉ | oil |
| I-1-b-29 | H | CH₃ | H | 4-SCH₃ | t-C₄H₉ | oil |
| I-1-b-30 | H | CH₃ | H | 4-i-C₃H₇ | t-C₄H₉ | oil |
| I-1-b-31 | H | CH₃ | H | 3,5-(CF₃)₂ | t-C₄H₉ | oil |
| I-1-b-32 | H | CH₃ | H | 4-Cl | i-C₃H₇ | oil |
| I-1-b-33 | H | CH₃ | H | 4-F | c-C₃H₅ | oil |
| I-1-b-34 | CH₃ | CH₃ | CH₃ | 4-F | t-C₄H₉ | oil |
| I-1-b-35 | H | CH₃ | CH₃ | 4-Cl | t-C₄H₉ | oil |
| I-1-b-36 | CH₃ | CH₃ | H | 4-Cl | t-C₄H₉ | 69 |
| I-1-b-37 | CH₃ | CH₃ | H | 4-F | t-C₄H₉ | oil |
| I-1-b-38 | CH₃ | CH₃ | H | 4-Cl | i-C₃H₇ | oil |
| I-1-b-39 | CH₃ | CH₃ | H | 4-F | i-C₃H₇ | oil |
| I-1-b-40 | CH₃ | CH₃ | CH₃ | 4-Cl | t-C₄H₉ | 35 |
| I-1-b-41 | CH₃ | CH₃ | CH₃ | 4-Cl | i-C₃H₇ | 138 |
| I-1-b-42 | H | CH₃ | H | 3-OCH₃ | c-C₃H₇ | oil |
| I-1-b-43 | H | CH₃ | H | 3-OCH₃ | i-C₃H₇ | oil |
| I-1-b-44 | H | Cl | H | 4-CF₃ | t-C₄H₉ | oil |
| I-1-b-45 | H | Cl | H | 4-Cl | t-C₄H₉ | oil |
| I-1-b-46 | H | Cl | H | 4-F | t-C₄H₉ | 46 |
| I-1-6-47 | H | Cl | H | 4-Cl | CH₃ | oil |
| I-1-b-48 | H | Cl | H | 4-Cl | C₂H₅ | oil |
| I-1-b-49 | H | Cl | H | 4-Cl | i-C₃H₇ | oil |
| I-1-b-50 | H | Cl | H | 4-Cl | c-C₃H₇ | oil |
| I-1-b-51 | H | Cl | H | 2,4-Cl₂ | t-C₄H₉ | oil |
| I-1-b-52 | H | Cl | H | 3,4-Cl₂ | t-C₄H₉ | oil |
| I-1-b-53 | H | Cl | H | 3,5-Cl₂ | t-C₄H₉ | oil |
| I-1-b-54 | H | Cl | H | 2,4-F₂ | t-C₄H₉ | oil |
| I-1-b-55 | H | Cl | H | 3-Cl, 4-F | t-C₄H₉ | oil |
| I-1-b-56 | H | Cl | H | 2-Cl, 5-Cl | t-C₄H₉ | oil |

The following compounds of the formula (I-2-b) are obtained analogously to Example (I-1-b-1) and in accordance with the general instructions for preparing compounds of the formula (I-b)

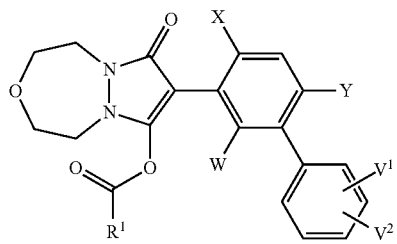

(I-2-b)

| Ex. No. | W | X | Y | V¹/V² | R¹ | m.p. (° C.) |
|---|---|---|---|---|---|---|
| I-2-b-1 | H | CH₃ | H | 2-Cl | t-C₄H₉ | oil |
| I-2-b-2 | H | CH₃ | H | 3-Cl | t-C₄H₉ | oil |
| I-2-b-3 | H | CH₃ | H | 4-Cl | t-C₄H₉ | oil |

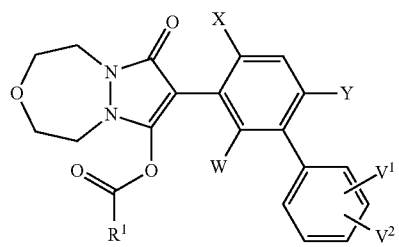

(I-2-b)

| Ex. No. | W | X | Y | V¹/V² | R¹ | m.p. (° C.) |
|---|---|---|---|---|---|---|
| I-2-b-4 | H | CH₃ | H | 2-F | t-C₄H₉ | oil |
| I-2-b-5 | H | CH₃ | H | 3-F | t-C₄H₉ | oil |
| I-2-b-6 | H | CH₃ | H | 4-F | t-C₄H₉ | oil |
| I-2-b-7 | H | CH₃ | H | 2-CH₃ | t-C₄H₉ | oil |
| I-2-b-8 | H | CH₃ | H | 3-CH₃ | t-C₄H₉ | oil |
| I-2-b-9 | H | CH₃ | H | 4-CH₃ | t-C₄H₉ | oil |
| I-2-b-10 | H | CH₃ | H | 2,3-Cl₂ | t-C₄H₉ | 155 |
| I-2-b-11 | H | CH₃ | H | 2,4-Cl₂ | t-C₄H₉ | 117 |
| I-2-b-12 | H | CH₃ | H | 2,5-Cl₂ | t-C₄H₉ | oil |
| I-2-b-13 | H | CH₃ | H | 3,4-Cl₂ | t-C₄H₉ | oil |
| I-2-b-14 | H | CH₃ | H | 3,5-Cl₂ | t-C₄H₉ | oil |
| I-2-b-15 | H | CH₃ | H | 2,4-F₂ | t-C₄H₉ | 174 |
| I-2-b-16 | H | CH₃ | H | 2,5-F₂ | t-C₄H₉ | 184 |
| I-2-b-17 | H | CH₃ | H | 3-Cl, 4-F | t-C₄H₉ | oil |
| I-2-b-18 | H | CH₃ | H | 2-CF₃ | t-C₄H₉ | oil |
| I-2-b-19 | H | CH₃ | H | 3-CF₃ | t-C₄H₉ | oil |
| I-2-b-20 | H | CH₃ | H | 4-CF₃ | t-C₄H₉ | 187 |
| I-2-b-21 | H | CH₃ | H | 2-OCH₃ | t-C₄H₉ | oil |
| I-2-b-22 | H | CH₃ | H | 3-OCH₃ | t-C₄H₉ | oil |
| I-2-b-23 | H | CH₃ | H | 4-OCH₃ | t-C₄H₉ | oil |
| I-2-b-24 | H | CH₃ | H | 3-SO₂C₂H₅ | t-C₄H₉ | oil |
| I-2-b-25 | H | CH₃ | H | 4-SO₂C₂H₅ | t-C₄H₉ | oil |
| I-2-b-26 | H | CH₃ | H | 3-NO₂ | t-C₄H₉ | oil |
| I-2-b-27 | H | CH₃ | H | 4-OCF₃ | t-C₄H₉ | oil |
| I-2-b-28 | H | CH₃ | H | 4-OPh | t-C₄H₉ | 104 |
| I-2-b-29 | H | CH₃ | H | 4-SCH₃ | t-C₄H₉ | 176 |
| I-2-b-30 | H | CH₃ | H | 4-i-C₃H₇ | t-C₄H₉ | 138 |
| I-2-b-31 | H | CH₃ | H | 4-Cl | i-C₃H₇ | 129 |
| I-2-b-32 | CH₃ | CH₃ | CH₃ | 4-F | t-C₄H₉ | oil |
| I-2-b-33 | H | CH₃ | CH₃ | 4-Cl | t-C₄H₉ | 105 |
| I-2-b-34 | CH₃ | CH₃ | H | 4-Cl | t-C₄H₉ | 52 |
| I-2-b-35 | CH₃ | CH₃ | H | 4-F | t-C₄H₉ | oil |
| I-2-b-36 | CH₃ | CH₃ | H | 4-F | i-C₃H₇ | oil |
| I-2-b-37 | CH₃ | CH₃ | CH₃ | 4-Cl | t-C₄H₉ | oil |
| I-2-b-38 | H | CH₃ | H | 2,4-Cl₂ | i-C₃H₇ | oil |
| I-2-b-39 | H | CH₃ | H | 2,4-Cl₂ | c-C₃H₅ | oil |
| I-2-b-40 | H | Cl | H | 4-CF₃ | t-C₄H₉ | oil |
| I-2-b-41 | H | Cl | H | 4-Cl | t-C₄H₉ | oil |
| I-2-b-42 | H | Cl | H | 4-F | t-C₄H₉ | oil |
| I-2-b-43 | H | Cl | H | 4-Cl | CH₃ | 171 |
| I-2-b-44 | H | Cl | H | 4-Cl | C₂H₅ | 183 |
| I-2-b-45 | H | Cl | H | 4-Cl | i-C₃H₇ | 189 |
| I-2-b-46 | H | Cl | H | 4-Cl | c-C₃H₅ | 172 |
| I-2-b-47 | H | Cl | H | 2,4-Cl₂ | t-C₄H₉ | oil |
| I-2-b-48 | H | Cl | H | 3,4-Cl₂ | t-C₄H₉ | 103 |
| I-2-b-49 | H | Cl | H | 3,5-Cl₂ | t-C₄H₉ | 168 |
| I-2-b-50 | H | Cl | H | 3-Cl, 4-F | t-C₄H₉ | 90 |
| I-2-b-51 | H | Cl | H | 2,5-Cl₂ | t-C₄H₉ | oil |
| I-2-b-52 | H | Cl | H | 2,4-F₂ | t-C₄H₉ | oil |

The following compounds of the formula (I-3-b) are obtained analogously to Example (I-1-b-1) and in accordance with the general instructions for preparing compounds of the formula (I-b)

(I-3-b)

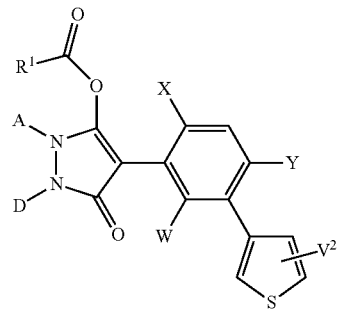

| Ex. No. | W | X | Y | V² | A | D | R¹ | m.p. (°C.) |
|---|---|---|---|---|---|---|---|---|
| I-3-b-1 | H | CH₃ | H | H | —(CH₂)₄— | | t-C₄H₉ | 155 |
| I-3-b-2 | H | CH₃ | H | H | —(CH₂)₂—O—(CH₂)₂— | | t-C₄H₉ | oil |

The following compounds of the formula (I-4-b) are obtained analogously to Example (I-1-b-1) and in accordance with the general instructions for preparing compounds of the formula (I-b)

(I-4-b)

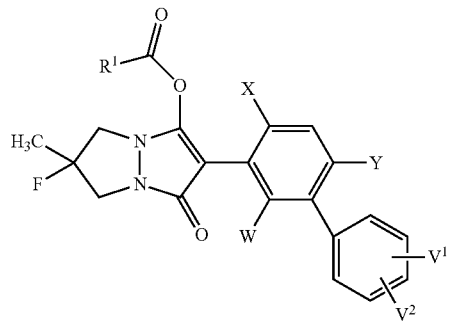

| Ex. No. | W | X | Y | V²/V² | R¹ | m.p. (°C.) |
|---|---|---|---|---|---|---|
| I-4-b-1 | H | CH₃ | H | 4-F | t-C₄H₉ | 158-160 |
| I-4-b-2 | H | CH₃ | Cl | 4-Cl | t-C₄H₉ | oil |
| I-4-b-3 | H | Cl | H | 4-F | t-C₄H₉ | oil |
| I-4-b-4 | H | Cl | H | 4-Cl | t-C₄H₉ | oil |

The following compounds of the formula (I-5-b) are obtained analogously to Example (I-1-b-1) and in accordance with the general instructions for preparing compounds of the formula (I-b)

(I-5-b)

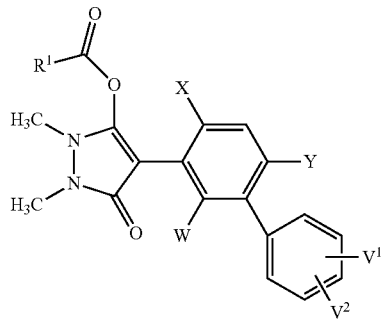

| Ex. No. | W | X | Y | V²/V² | R¹ | m.p. (°C.) |
|---|---|---|---|---|---|---|
| I-5-b-1 | H | CH₃ | H | 4-F | t-C₄H₉ | 123-124 |
| I-5-b-2 | H | CH₃ | H | 4-Cl | t-C₄H₉ | oil |
| I-5-b-3 | H | Cl | H | 4-F | t-C₄H₉ | 43-44 |
| I-5-b-4 | H | Cl | H | 4-Cl | t-C₄H₉ | 44-45 |

The following compounds of the formula (I-6-b) are obtained analogously to Example (I-1-b-1) and in accordance with the general instructions for preparing compounds of the formula (I-b)

(I-6-b)

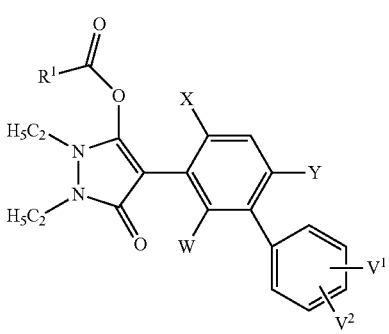

| Ex. No. | W | X | Y | V²/V² | R¹ | m.p. (°C.) |
|---|---|---|---|---|---|---|
| I-6-b-1 | H | CH₃ | H | 4-F | t-C₄H₉ | 85 |
| I-6-b-2 | H | CH₃ | H | 4-Cl | t-C₄H₉ | 43 |
| I-6-b-3 | H | Cl | H | 4-F | t-C₄H₉ | oil |
| I-6-b-4 | H | Cl | H | 4-Cl | t-C₄H₉ | oil |

The following compounds of the formula (I-7-b) are obtained analogously to Example (I-1-b-1) and in accordance with the general instructions for preparing compounds of the formula (I-b)

(1-7-b)

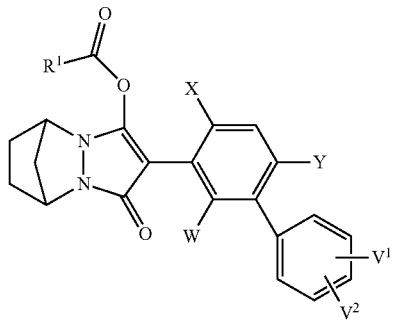

| Ex. No. | W | X | Y | V²/V² | R¹ | m.p. (° C.) |
|---|---|---|---|---|---|---|
| I-7-b-1 | H | CH₃ | H | 4-Cl | t-C₄H₉ | 206 |
| I-7-b-2 | H | Cl | H | 4-Cl | t-C₄H₉ | oil |

Example I-1-c-1

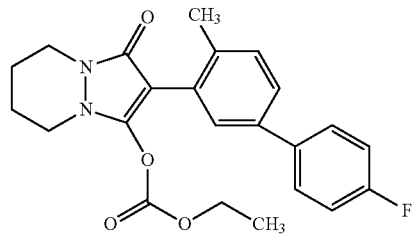

At room temperature, triethylamine (0.13 g; 1.3 μmol) and a solution of ethyl chloroformate (0.14 g; 1.3 μmol) in 10 ml of methylene chloride are added successively to a solution of 0.4 g (1.2 mmol) of the compound of Example (I-a-1) in 20 ml of methylene chloride. After 12 h of stirring at room temperature, the mixture is diluted with 100 ml of methylene chloride and washed in each case 1× with 10% strength citric acid and 10% strength aqueous sodium hydroxide solution. The organic phase is dried over sodium sulphate and the solvent is removed under reduced pressure.

Yield: 0.45 g (94% of theory); light-brown oil.

The following compounds of the formula (I-1-c) are obtained analogously to Example (I-1-c-1) and in accordance with the general instructions for preparing compounds of the formula (I-c)

(I-1-c)

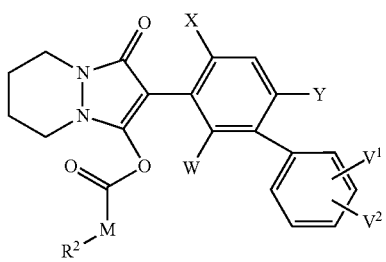

| Ex. No. | W | X | Y | V¹V² | M | R² | m.p. (° C.) |
|---|---|---|---|---|---|---|---|
| I-1-c-2 | H | CH₃ | H | 2-Cl | O | C₂H₅ | oil |
| I-1-c-3 | H | CH₃ | H | 3-Cl | O | C₂H₅ | 172 |
| I-1-c-4 | H | CH₃ | H | 4-Cl | O | C₂H₅ | oil |
| I-1-c-5 | H | CH₃ | H | 2-F | O | C₂H₅ | oil |
| I-1-c-6 | H | CH₃ | H | 3-F | O | C₂H₅ | oil |
| I-1-c-1 | H | CH₃ | H | 4-F | O | C₂H₅ | oil |
| I-1-c-7 | H | CH₃ | H | 2-CH₃ | O | C₂H₅ | 170 |
| I-1-c-8 | H | CH₃ | H | 3-CH₃ | O | C₂H₅ | oil |
| I-1-c-9 | H | CH₃ | H | 4-CH₃ | O | C₂H₅ | oil |
| I-1-c-10 | H | CH₃ | H | 2,3-Cl₂ | O | C₂H₅ | oil |
| I-1-c-11 | H | CH₃ | H | 2,4-Cl₂ | O | C₂H₅ | oil |
| I-1-c-12 | H | CH₃ | H | 2,5-Cl₂ | O | C₂H₅ | oil |
| I-1-c-13 | H | CH₃ | H | 3,4-Cl₂ | O | C₂H₅ | oil |
| I-1-c-14 | H | CH₃ | H | 3,5-Cl₂ | O | C₂H₅ | oil |
| I-1-c-15 | H | CH₃ | H | 2,4-F₂ | O | C₂H₅ | oil |
| I-1-c-16 | H | CH₃ | H | 2,5-F₂ | O | C₂H₅ | oil |
| I-1-c-17 | H | CH₃ | H | 3-Cl, 4-F | O | C₂H₅ | oil |

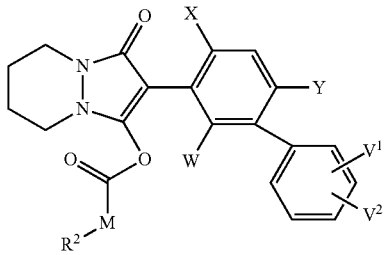

(I-1-c)

| Ex. No. | W | X | Y | $V^1V^2$ | M | $R^2$ | m.p. (°C.) |
|---|---|---|---|---|---|---|---|
| I-1-c-18 | H | $CH_3$ | H | 3-$CF_3$ | O | $C_2H_5$ | oil |
| I-1-c-19 | H | $CH_3$ | H | 4-$CF_3$ | O | $C_2H_5$ | oil |
| I-1-c-20 | H | $CH_3$ | H | 2-$OCH_3$ | O | $C_2H_5$ | oil |
| I-1-c-21 | H | $CH_3$ | H | 3-$OCH_3$ | O | $C_2H_5$ | oil |
| I-1-c-22 | H | $CH_3$ | H | 3-$SO_2C_2H_3$ | O | $C_2H_5$ | oil |
| I-1-c-23 | H | $CH_3$ | H | 4-$SO_2C_2H_5$ | O | $C_2H_5$ | oil |
| I-1-c-24 | H | $CH_3$ | H | 4-OPh | O | $C_2H_5$ | 81 |
| I-1-c-25 | H | $CH_3$ | H | 4-$SCH_3$ | O | $C_2H_5$ | oil |
| I-1-c-26 | H | $CH_3$ | H | 4-i-$C_3H_7$ | O | $C_2H_5$ | oil |
| I-1-c-27 | H | $CH_3$ | $CH_3$ | 4-Cl | O | $C_2H_5$ | oil |
| I-1-c-28 | $CH_3$ | $CH_3$ | H | 4-Cl | O | $C_2H_5$ | oil |
| I-1-c-29 | $CH_3$ | $CH_3$ | $CH_3$ | 4-Cl | O | $C_2H_5$ | 38 |
| I-1-c-30 | $CH_3$ | $CH_3$ | H | 4-F | O | $C_2H_5$ | oil |
| I-1-c-31 | H | $CH_3$ | H | 3-$OCH_3$ | O | $H_5C_2O-(CH_2)_2-$ | oil |
| I-1-c-32 | H | $CH_3$ | H | 4-Cl | O | $C_2H_5$ | 53 |
| I-1-c-33 | H | Cl | H | 4-F | O | $C_2H_5$ | oil |
| I-1-c-34 | H | Cl | H | 4-Cl | O | $CH_3$ | oil |
| I-1-c-35 | H | Cl | H | 4-Cl | O | $H_5C_2-O-(CH_2)_2-$ | oil |
| I-1-c-36 | H | Cl | H | 3,4-$Cl_2$ | O | $C_2H_5$ | oil |
| I-1-c-37 | H | Cl | H | 3,5-$Cl_2$ | O | $C_2H_5$ | oil |
| I-1-c-38 | H | Cl | H | 2,4-$F_2$ | O | $C_2H_5$ | oil |
| I-1-c-39 | H | Cl | H | 2,5-$Cl_2$ | O | $C_2H_5$ | 201 |

The following compounds of the formula (I-2-c) are obtained analogously to Example (I-1-c-1) and in accordance with the general instructions for preparing compounds of the formula (I-c)

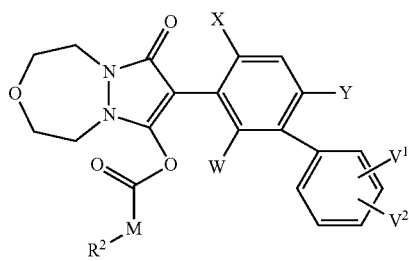

(I-2-c)

| Ex. No. | W | X | Y | $V^1/V^2$ | M | $R^2$ | m.p. (°C.) |
|---|---|---|---|---|---|---|---|
| I-2-c-1 | H | $CH_3$ | H | 2-Cl | O | $C_2H_5$ | oil |
| I-2-c-2 | H | $CH_3$ | H | 3-Cl | O | $C_2H_5$ | oil |
| I-2-c-3 | H | $CH_3$ | H | 4-Cl | O | $C_2H_5$ | oil |
| I-2-c-4 | H | $CH_3$ | H | 2-F | O | $C_2H_5$ | oil |
| I-2-c-5 | H | $CH_3$ | H | 3-F | O | $C_2H_5$ | oil |
| I-2-c-6 | H | $CH_3$ | H | 4-F | O | $C_2H_5$ | oil |
| I-2-c-7 | H | $CH_3$ | H | 2-$CH_3$ | O | $C_2H_5$ | oil |
| I-2-c-8 | H | $CH_3$ | H | 3-$CH_3$ | O | $C_2H_5$ | oil |
| I-2-c-9 | H | $CH_3$ | H | 4-$CH_3$ | O | $C_2H_5$ | oil |
| I-2-c-10 | H | $CH_3$ | H | 2,3-$Cl_2$ | O | $C_2H_5$ | 178 |
| I-2-c-11 | H | $CH_3$ | H | 2,4-$Cl_2$ | O | $C_2H_5$ | oil |
| I-2-c-12 | H | $CH_3$ | H | 2,5-$Cl_2$ | O | $C_2H_5$ | oil |
| I-2-c-13 | H | $CH_3$ | H | 3,4-$Cl_2$ | O | $C_2H_5$ | oil |
| I-2-c-14 | H | $CH_3$ | H | 3,5-$Cl_2$ | O | $C_2H_5$ | oil |

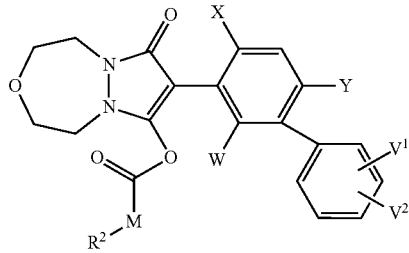

(I-2-c)

| Ex. No. | W | X | Y | V¹/V² | M | R² | m.p. (° C.) |
|---|---|---|---|---|---|---|---|
| I-2-c-15 | H | CH₃ | H | 2,4-F₂ | O | C₂H₅ | 120 |
| I-2-c-16 | H | CH₃ | H | 2,5-F₂ | O | C₂H₅ | oil |
| I-2-c-17 | H | CH₃ | H | 3-Cl, 4-F | O | C₂H₅ | oil |
| I-2-c-18 | H | CH₃ | H | 2-CF₃ | O | C₂H₅ | 172 |
| I-2-c-19 | H | CH₃ | H | 3-CF₃ | O | C₂H₅ | oil |
| I-2-c-20 | H | CH₃ | H | 4-CF₃ | O | C₂H₅ | 111 |
| I-2-c-21 | H | CH₃ | H | 2-OCH₃ | O | C₂H₅ | oil |
| I-2-c-22 | H | CH₃ | H | 3-OCH₃ | O | C₂H₅ | oil |
| I-2-c-23 | H | CH₃ | H | 4-OCH₃ | O | C₂H₅ | oil |
| I-2-c-24 | H | CH₃ | H | 3-SO₂C₂H₅ | O | C₂H₅ | oil |
| I-2-c-25 | H | CH₃ | H | 4-SO₂C₂H₅ | O | C₂H₅ | oil |
| I-2-c-26 | H | CH3 | H | 3-NO₂ | O | C₂H₅ | oil |
| I-2-c-27 | H | CH₃ | H | 4-OCF₃ | O | C₂H₅ | oil |
| I-2-c-28 | H | CH₃ | H | 4-OPh | O | C₂H₅ | oil |
| I-2-c-29 | H | CH₃ | H | 4-SCH₃ | O | C₂H₅ | 131 |
| I-2-c-30 | H | CH₃ | H | 4-i-C₃H₇ | O | C₂H₅ | oil |
| I-2-c-31 | H | CH₃ | H | 3,5-(CF₃)₂ | O | C₂H₅ | oil |
| I-2-c-32 | H | CH₃ | CH₃ | 4-Cl | O | C₂H₅ | 53 |
| I-2-c-33 | CH₃ | CH₃ | H | 4-Cl | O | C₂H₅ | oil |
| I-2-c-34 | CH₃ | CH₃ | H | 4-F | O | C₂H₅ | oil |
| I-2-c-35 | H | CH₃ | H | 2,4-Cl₂ | O | C₂H₅ | oil |
| I-2-c-36 | H | Cl | H | 4-F | O | C₂H₅ | oil |
| I-2-c-37 | H | Cl | H | 4-Cl | O | C₂H₅ | oil |
| I-2-c-38 | H | Cl | H | 4-Cl | O | CH₃ | 198 |
| I-2-c-39 | H | Cl | H | 4-Cl | O | H₅C₂—O—(CH₂)₂— | oil |
| I-2-c-40 | H | Cl | H | 3,5-Cl₂ | O | C₂H₅ | 150 |
| I-2-c-41 | H | Cl | H | 2,4-F₂ | O | C₂H₅ | oil |
| I-2-c-42 | H | Cl | H | 2,5-Cl₂ | O | C₂H₅ | 50 |

The following compounds of the formula (I-3-c) are obtained analogously to Example (I-1-c-1) and in accordance with the general instructions for preparing compounds of the formula (I-c)

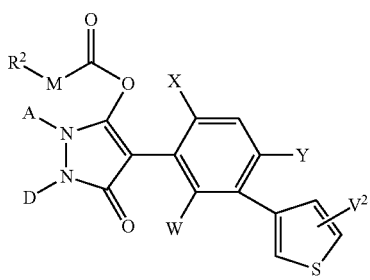

| Ex. No. | W | X | Y | V² | A | D | M | R² | |
|---|---|---|---|---|---|---|---|---|---|
| I-3-c-1 | H | CH₃ | H | H | —(CH₂)₄— | | O | C₂H₅ | oil |
| I-3-c-2 | H | CH₃ | H | H | —(CH₂)₂—O—(CH₂)₂— | | O | C₂H₅ | oil |

The following compounds of the formula (I-4-c) are obtained analogously to Example (I-1-c-1) and in accordance with the general instructions for preparing compounds of the formula (I-c)

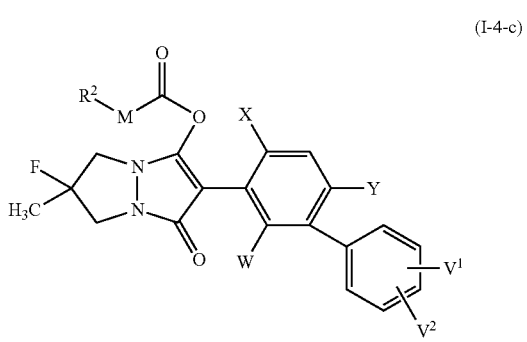

(I-4-c)

| Ex. No. | W | X | Y | V¹/V² | M | R² | m.p. ° C. |
|---|---|---|---|---|---|---|---|
| I-4-c-1 | H | CH₃ | H | 4-F | O | C₂H₅ | oil |
| I-4-c-2 | H | Cl | H | 4-Cl | O | C₂H₅ | oil |

The following compounds of the formula (I-5-c) are obtained analogously to Example (I-1-c-1) and in accordance with the general instructions for preparing compounds of the formula (I-c)

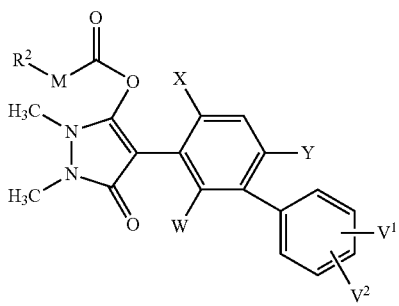

(I-5-c)

| Ex. No. | W | X | Y | V¹/V² | M | R² | m.p. °C. |
|---|---|---|---|---|---|---|---|
| I-5-c-1 | H | CH₃ | H | 4-F | O | C₂H₅ | oil |
| I-5-c-2 | H | CH₃ | H | 4-Cl | O | C₂H₅ | oil |
| I-5-c-3 | H | Cl | H | 4-F | O | C₂H₅ | oil |
| I-5-c-4 | H | Cl | H | 4-Cl | O | C₂H₅ | oil |

The following compounds of the formula (I-6-c) are obtained analogously to Example (I-1-c-1) and in accordance with the general instructions for preparing compounds of the formula (I-c)

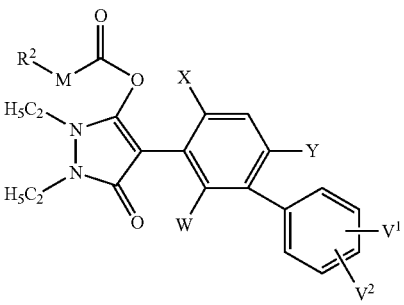

(I-6-c)

| Ex. No. | W | X | Y | V¹/V² | M | R² | m.p. °C. |
|---|---|---|---|---|---|---|---|
| I-6-c-1 | H | Cl | H | 4-Cl | O | C₂H₅ | oil |

The following compounds of the formula (I-7-c) are obtained analogously to Example (I-1-c-1) and in accordance with the general instructions for preparing compounds of the formula (I-c)

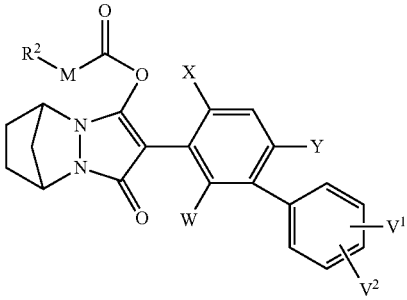

(I-7-c)

| Ex. No. | W | X | Y | V¹/V² | M | R² | m.p. °C. |
|---|---|---|---|---|---|---|---|
| I-7-c-1 | H | CH₃ | H | 4-Cl | O | C₂H₅ | 25 |
| I-7-c-1 | H | Cl | H | 4-Cl | O | C₂H₅ | 26 |

Example I-d-1

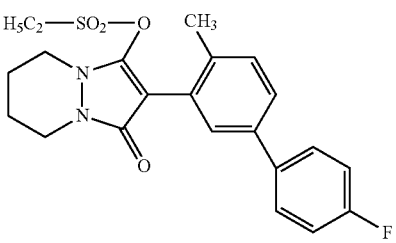

At room temperature, triethylamine (0.13 g; 1.3 mmol) and a solution of ethylsulphonyl chloride (0.17 g; 1.3 mmol) in 10 ml of dichloromethane are added successively to a solution of 0.4 g (1.2 mmol) of Example (I-1-a-1) in 20 ml of dichloromethane. After 10 hours of stirring at room temperature, the mixture is diluted with 100 ml of dichloromethane and washed in each case 1× with 10% strength citric acid and 10% strength aqueous sodium hydroxide solution. The organic phase is dried over sodium sulphate and the solvent is removed under reduced pressure.

Yield: 0.4 g (70% of theory); light-brown oil.

The following compounds of the formula (I-d) are obtained analogously to Example (I-d-1) and in accordance with the general instructions for the preparation

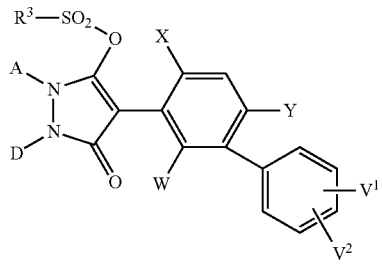

(I-d)

| Ex. No. | W | X | Y | V¹/V² | A | D | R³ | m.p. °C. |
|---|---|---|---|---|---|---|---|---|
| I-d-2 | H | Cl | H | 4-Cl | —(CH₂)₄— | | C₂H₅ | oil |
| I-d-3 | H | Cl | H | 4-Cl | —(CH₂)₄— | | i-C₃H₇ | oil |

-continued

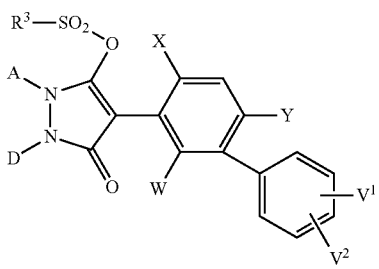

(I-d)

| Ex. No. | W | X | Y | V¹/V² | A | D | R³ | m.p. °C. |
|---|---|---|---|---|---|---|---|---|
| I-d-4 | H | Cl | H | 4-Cl | —(CH$_2$)$_4$— | | CH$_3$ | oil |
| I-d-5 | H | Cl | H | 4-Cl | —(CH$_2$)$_2$—O—(CH$_2$)$_2$ | | C$_2$H$_5$ | 163 |
| I-d-6 | H | Cl | H | 4-Cl | —(CH$_2$)$_2$—O—(CH$_2$)$_2$ | | i-C$_3$H$_7$ | oil |
| I-d-7 | H | Cl | H | 4-Cl | —(CH$_2$)$_2$—O—(CH$_2$)$_2$ | | CH$_3$ | 201 |

Example (V-1-1)

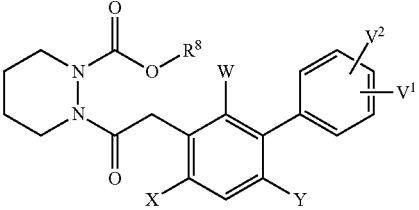

(V-1-1)

1.04 g (5.3 mmol) of A are dissolved in 3.0 ml of methylene chloride, and 1.2 g (11.8 µmol) of triethylamine and a solution of 1.4 g (5.3 mmol) of B in 20 ml of methylene chloride are successively added dropwise. The mixture is stirred at room temperature for 12 h, 100 ml of methylene chloride are added and the mixture is washed in each case 1× with 2N hydrochloric acid and water. The organic phase is dried over sodium sulphate, filtered and concentrated under reduced pressure.

Yield: 2 g (98% of theory); yellow oil which is not purified any further for subsequent reaction.

The following compounds of the formula (V-1) are obtained analogously to Example (V-1-1) and in accordance with the general instructions for preparing compounds of the formula (V)

(V-1)

| Ex. No. | W | X | Y | V¹/V² | R⁸ | m.p. °C. |
|---|---|---|---|---|---|---|
| V-1-2 | H | CH$_3$ | H | 2-Cl | C$_2$H$_5$ | oil |
| V-1-3 | H | CH$_3$ | H | 3-Cl | C$_2$H$_5$ | oil |
| V-1-4 | H | CH$_3$ | H | 4-Cl | C$_2$H$_5$ | oil |
| V-1-5 | H | CH$_3$ | H | 2-F | C$_2$H$_5$ | oil |
| V-1-6 | H | CH$_3$ | H | 3-F | C$_2$H$_5$ | oil |
| V-1-1 | H | CH$_3$ | H | 4-F | C$_2$H$_5$ | oil |
| V-1-7 | H | CH$_3$ | H | 2-CH$_3$ | C$_2$H$_5$ | oil |
| V-1-8 | H | CH$_3$ | H | 3-CH$_3$ | C$_2$H$_5$ | oil |
| V-1-9 | H | CH$_3$ | H | 4-CH$_3$ | C$_2$H$_5$ | oil |
| V-1-10 | H | CH$_3$ | H | 2,3-Cl$_2$ | C$_2$H$_5$ | oil |
| V-1-11 | H | CH$_3$ | H | 2,4-Cl$_2$ | C$_2$H$_5$ | oil |
| V-1-12 | H | CH$_3$ | H | 2,5-Cl$_2$ | C$_2$H$_5$ | oil |
| V-1-13 | H | CH$_3$ | H | 3,4-Cl$_2$ | C$_2$H$_5$ | oil |
| V-1-14 | H | CH$_3$ | H | 3,5-Cl$_2$ | C$_2$H$_5$ | oil |
| V-1-15 | H | CH$_3$ | H | 2,4-F$_2$ | C$_2$H$_5$ | oil |
| V-1-16 | H | CH$_3$ | H | 2,5-F$_2$ | C$_2$H$_5$ | oil |
| V-1-17 | H | CH$_3$ | H | 3-Cl,4-F | C$_2$H$_5$ | oil |
| V-1-18 | H | CH$_3$ | H | 2-CF$_3$ | C$_2$H$_5$ | oil |
| V-1-19 | H | CH$_3$ | H | 3-CF$_3$ | C$_2$H$_5$ | oil |
| V-1-20 | H | CH$_3$ | H | 4-CF$_3$ | C$_2$H$_5$ | oil |
| V-1-21 | H | CH$_3$ | H | 2-OCH$_3$ | C$_2$H$_5$ | oil |
| V-1-22 | H | CH$_3$ | H | 3-OCH$_3$ | C$_2$H$_5$ | oil |
| V-1-23 | H | CH$_3$ | H | 4-OCH$_3$ | C$_2$H$_5$ | oil |
| V-1-24 | H | CH$_3$ | H | 3-SO$_2$C$_2$H$_5$ | C$_2$H$_5$ | oil |
| V-1-25 | H | CH$_3$ | H | 4-SO$_2$C$_2$H$_5$ | C$_2$H$_5$ | oil |
| V-1-26 | H | CH$_3$ | H | 3-NO$_2$ | C$_2$H$_5$ | oil |
| V-1-27 | H | CH$_3$ | H | 4-OCF$_3$ | C$_2$H$_5$ | oil |
| V-1-28 | H | CH$_3$ | H | 4-OPh | C$_2$H$_5$ | oil |
| V-1-29 | H | CH$_3$ | H | 4-SCH$_3$ | C$_2$H$_5$ | oil |
| V-1-30 | H | CH$_3$ | H | 4-i-C$_3$H$_7$ | C$_2$H$_5$ | oil |
| V-1-31 | H | CH$_3$ | H | 3,5-(CF$_3$)$_2$ | C$_2$H$_5$ | oil |
| V-1-32 | CH$_3$ | CH$_3$ | CH$_3$ | 4-F | C$_2$H$_5$ | oil |
| V-1-33 | H | CH$_3$ | CH$_3$ | 4-Cl | C$_2$H$_5$ | oil |
| V-1-34 | CH$_3$ | CH$_3$ | H | 4-F | C$_2$H$_5$ | oil |
| V-1-35 | CH$_3$ | CH$_3$ | H | 4-Cl | C$_2$H$_5$ | oil |
| V-1-36 | CH$_3$ | CH$_3$ | CH$_3$ | 4-Cl | C$_2$H$_5$ | oil |
| V-1-37 | H | Cl | H | 4-F | C$_2$H$_5$ | oil |
| V-1-38 | H | Cl | H | 4-Cl | C$_2$H$_5$ | oil |
| V-1-39 | H | Cl | H | 4-CF$_3$ | C$_2$H$_5$ | oil |
| V-1-40 | H | Cl | H | 2,4-Cl$_2$ | C$_2$H$_5$ | oil |
| V-1-41 | H | Cl | H | 3,4-Cl$_2$ | C$_2$H$_5$ | 65 |
| V-1-42 | H | Cl | H | 3,5-Cl$_2$ | C$_2$H$_5$ | oil |
| V-1-43 | H | Cl | H | 2,4-F$_2$ | C$_2$H$_5$ | oil |
| V-1-44 | H | Cl | H | 3-Cl, 4-F | C$_2$H$_5$ | oil |
| V-1-45 | H | Cl | H | 2,5-Cl$_2$ | C$_2$H$_5$ | oil |

The following compounds of the formula (V-2) are obtained analogously to Example (V-1-1) and in accordance with the general instructions for preparing compounds of the formula (V)

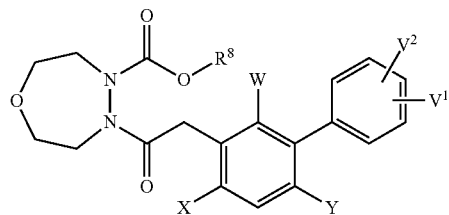

(V-2)

| Ex. No. | W | X | Y | V¹/V² | $R^8$ | m.p. °C. |
|---|---|---|---|---|---|---|
| V-2-1 | H | $CH_3$ | H | 2-Cl | $C_2H_5$ | oil |
| V-2-2 | H | $CH_3$ | H | 3-Cl | $C_2H_5$ | oil |
| V-2-3 | H | $CH_3$ | H | 4-Cl | $C_2H_5$ | oil |
| V-2-4 | H | $CH_3$ | H | 2-F | $C_2H_5$ | oil |
| V-2-5 | H | $CH_3$ | H | 3-F | $C_2H_5$ | oil |
| V-2-6 | H | $CH_3$ | H | 4-F | $C_2H_5$ | oil |
| V-2-7 | H | $CH_3$ | H | 2-$CH_3$ | $C_2H_5$ | oil |
| V-2-8 | H | $CH_3$ | H | 3-$CH_3$ | $C_2H_5$ | oil |
| V-2-9 | H | $CH_3$ | H | 4-$CH_3$ | $C_2H_5$ | oil |
| V-2-10 | H | $CH_3$ | H | 2,3-$Cl_2$ | $C_2H_5$ | oil |
| V-2-11 | H | $CH_3$ | H | 2,4-$Cl_2$ | $C_2H_5$ | oil |
| V-2-12 | H | $CH_3$ | H | 2,5-$Cl_2$ | $C_2H_5$ | oil |
| V-2-13 | H | $CH_3$ | H | 3,4-$Cl_2$ | $C_2H_5$ | oil |
| V-2-14 | H | $CH_3$ | H | 3,5-$Cl_2$ | $C_2H_5$ | oil |
| V-2-15 | H | $CH_3$ | H | 2,4-$F_2$ | $C_2H_5$ | oil |
| V-2-16 | H | $CH_3$ | H | 2,5-$F_2$ | $C_2H_5$ | oil |
| V-2-17 | H | $CH_3$ | H | 3-Cl, 4-F | $C_2H_5$ | oil |
| V-2-18 | H | $CH_3$ | H | 2-$CF_3$ | $C_2H_5$ | oil |
| V-2-19 | H | $CH_3$ | H | 3-$CF_3$ | $C_2H_5$ | oil |
| V-2-20 | H | $CH_3$ | H | 4-$CF_3$ | $C_2H_5$ | oil |
| V-2-21 | H | $CH_3$ | H | 2-$OCH_3$ | $C_2H_5$ | oil |
| V-2-22 | H | $CH_3$ | H | 3-$OCH_3$ | $C_2H_5$ | oil |
| V-2-23 | H | $CH_3$ | H | 4-$OCH_3$ | $C_2H_5$ | oil |
| V-2-24 | H | $CH_3$ | H | 3-$SO_2C_2H_5$ | $C_2H_5$ | oil |
| V-2-25 | H | $CH_3$ | H | 4-$SO_2C_2H_5$ | $C_2H_5$ | oil |
| V-2-26 | H | $CH_3$ | H | 3-$NO_2$ | $C_2H_5$ | oil |
| V-2-27 | H | $CH_3$ | H | 4-$OCF_3$ | $C_2H_5$ | oil |
| V-2-28 | H | $CH_3$ | H | 4-OPh | $C_2H_5$ | oil |
| V-2-29 | H | $CH_3$ | H | 4-$SCH_3$ | $C_2H_5$ | oil |
| V-2-30 | H | $CH_3$ | H | 4-i-$C_3H_7$ | $C_2H_5$ | oil |
| V-2-31 | H | $CH_3$ | H | 3,5-$(CF_3)_2$ | $C_2H_5$ | oil |
| V-2-32 | $CH_3$ | $CH_3$ | $CH_3$ | 4-F | $C_2H_5$ | oil |
| V-2-33 | H | $CH_3$ | $CH_3$ | 4-Cl | $C_2H_5$ | oil |
| V-2-34 | $CH_3$ | $CH_3$ | H | 4-F | $C_2H_5$ | oil |
| V-2-35 | $CH_3$ | $CH_3$ | H | 4-Cl | $C_2H_5$ | oil |
| V-2-36 | $CH_3$ | $CH_3$ | $CH_3$ | 4-Cl | $C_2H_5$ | oil |
| V-2-37 | H | Cl | H | 4-F | $C_2H_5$ | oil |
| V-2-38 | H | Cl | H | 4-Cl | $C_2H_5$ | oil |
| V-2-39 | H | Cl | H | 4-$CF_3$ | $C_2H_5$ | oil |
| V-2-40 | H | Cl | H | 2,4-$Cl_2$ | $C_2H_5$ | oil |
| V-2-41 | H | Cl | H | 3,4-$Cl_2$ | $C_2H_5$ | oil |
| V-2-42 | H | Cl | H | 3,5-$Cl_2$ | $C_2H_5$ | oil |
| V-2-43 | H | Cl | H | 2,4-$F_2$ | $C_2H_5$ | oil |
| V-2-44 | H | Cl | H | 3-Cl, 4-F | $C_2H_5$ | oil |
| V-2-45 | H | Cl | H | 2,5-$Cl_2$ | $C_2H_5$ | oil |

The following compounds of the formula (V-3) are obtained analogously to Example (V-1-1) and in accordance with the general instructions for preparing compounds of the formula (V)

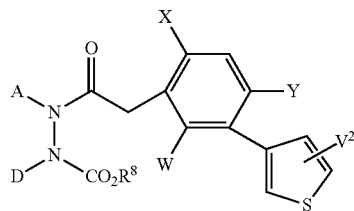

(V-3)

| Ex. No. | W | X | Y | V² | A | D | R |
|---|---|---|---|---|---|---|---|
| V-3-1 | H | $CH_3$ | H | H | —$(CH_2)_4$— | | $C_2H_5$ oil |
| V-3-2 | H | $CH_3$ | H | H | —$(CH_2)_2$—O—$(CH_2)_2$— | | $C_2H_5$ oil |

The following compounds of the formula (V-4) are obtained analogously to Example (V-1-1) and in accordance with the general instructions for preparing compounds of the formula (V)

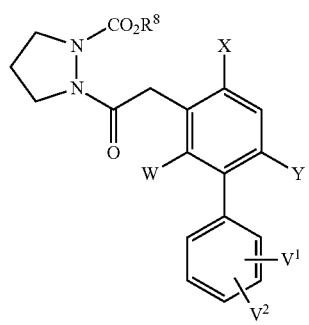

(V-4)

| Ex. No. | W | X | Y | V¹/V² | $R^8$ | m.p. °C. |
|---|---|---|---|---|---|---|
| V-4-1 | H | $CH_3$ | H | 4-F | $C_2H_5$ | oil |

The following compounds of the formula (V-5) are obtained analogously to Example (V-1-1) and in accordance with the general instructions for preparing compounds of the formula (V)

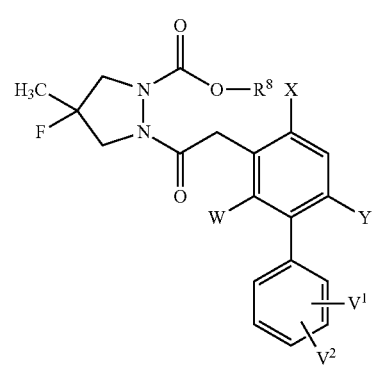

(V-5)

| Ex. No. | W | X | Y | V¹/V² | $R^8$ | m.p. °C. |
|---|---|---|---|---|---|---|
| V-5-1 | H | $CH_3$ | H | 4-F | $C_2H_5$ | oil |
| V-5-2 | H | $CH_3$ | H | 4-Cl | $C_2H_5$ | oil |

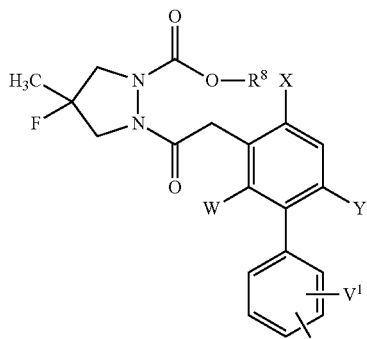

(V-5)

| Ex. No. | W | X | Y | $V^1/V^2$ | $R^8$ | m.p. °C. |
|---|---|---|---|---|---|---|
| V-5-3 | H | Cl | H | 4-F | $C_2H_5$ | oil |
| V-5-4 | H | Cl | H | 4-Cl | $C_2H_5$ | oil |

The following compounds of the formula (V-6) are obtained analogously to Example (V-1-1) and in accordance with the general instructions for preparing compounds of the formula (V)

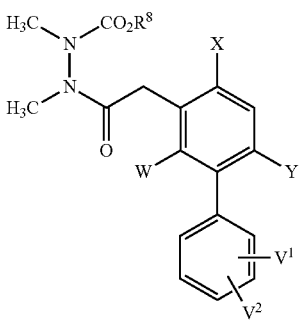

(V-6)

| Ex. No. | W | X | Y | $V^1/V^2$ | $R^8$ | m.p. °C. |
|---|---|---|---|---|---|---|
| V-6-1 | H | $CH_3$ | H | 4-F | $C_2H_5$ | oil |
| V-6-2 | H | $CH_3$ | H | 4-Cl | $C_2H_5$ | oil |
| V-6-3 | H | Cl | H | 4-F | $C_2H_5$ | oil |
| V-6-4 | H | Cl | H | 4-Cl | $C_2H_5$ | oil |

The following compounds of the formula (V-7) are obtained analogously to Example (V-1-1) and in accordance with the general instructions for preparing compounds of the formula (V)

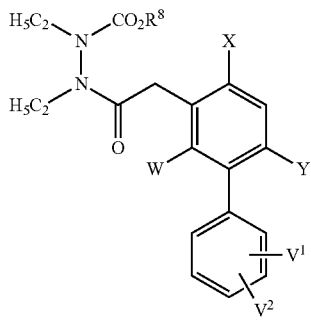

(V-7)

| Ex. No. | W | X | Y | $V^1/V^2$ | $R^8$ | m.p. °C. |
|---|---|---|---|---|---|---|
| V-7-1 | H | $CH_3$ | H | 4-F | $C_2H_5$ | oil |
| V-7-2 | H | $CH_3$ | H | 4-Cl | $C_2H_5$ | oil |
| V-7-3 | H | Cl | H | 4-F | $C_2H_5$ | oil |
| V-7-4 | H | Cl | H | 4-Cl | $C_2H_5$ | oil |

The following compounds of the formula (V-8) are obtained analogously to Example (V-1-1) and in accordance with the general instructions for preparing compounds of the formula (V)

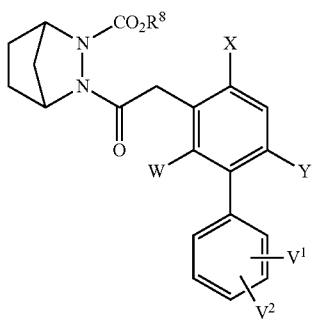

(V-8)

| Ex. No. | W | X | Y | $V^1/V^2$ | $R^8$ | m.p. °C. |
|---|---|---|---|---|---|---|
| V-8-1 | H | $CH_3$ | H | 4-Cl | $C_2H_5$ | 33 |
| V-8-2 | H | Cl | H | 4-Cl | $C_2H_5$ | 28 |

Example (XIX-1)

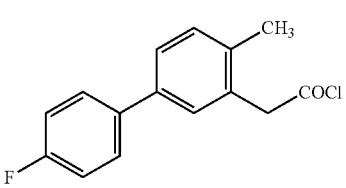

1.6 g (6.6 mmol) of the compound of Example (XX-1) are dissolved in 30 ml of methylene chloride and, at room temperature, a solution of 1.24 g (9.0 mmol) of oxalyl chloride in 10 ml of methylene chloride is added dropwise. The mixture is stirred at room temperature for 12 h and then, to bring the reaction to completion, heated under reflux for 3 h. The solution is concentrated under reduced pressure. The residue can be used for the next reaction step without further purification.

Yield: 1.6 g (92% of theory); yellow oil.

The following compounds of the formula (XIX) where T=Cl were obtained analogously to Example (XIX-1):

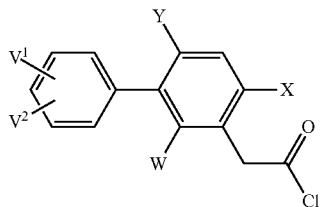

(XIX)

All Derivatives are Isolated as Oils!

| Ex. No. | W | X | Y | $V^1/V^2$ | δ-CH$_2$COCl (ppm) in CDCl$_3$ |
|---|---|---|---|---|---|
| XIX-2 | H | CH$_3$ | H | 2-Cl | 4.21 (s) |
| XIX-3 | H | CH$_3$ | H | 3-Cl | 4.22 (s) |
| XIX-4 | H | CH$_3$ | H | 2-F | 4.22 (s) |
| XIX-5 | H | CH$_3$ | H | 3-F | 4.22 (s) |
| XIX-1 | H | CH$_3$ | H | 4-F | 4.22 (s) |
| XIX-6 | H | CH$_3$ | H | 2-CH$_3$ | 4.18 (s) |
| XIX-7 | H | CH$_3$ | H | 3-CH$_3$ | 4.21 (s) |
| XIX-8 | H | CH$_3$ | H | 4-CH$_3$ | 4.21 (s) |
| XIX-9 | H | CH$_3$ | H | 2,3-Cl$_2$ | 4.20 (s) |
| XIX-10 | H | CH$_3$ | H | 2,4-Cl$_2$ | 4.21 (s) |
| XIX-11 | H | CH$_3$ | H | 2,5-Cl$_2$ | 4.21 (s) |
| XIX-12 | H | CH$_3$ | H | 3,4-Cl$_2$ | 4.23 (s) |
| XIX-13 | H | CH$_3$ | H | 3,5-Cl$_2$ | 4.22 (s) |
| XIX-14 | H | CH$_3$ | H | 2,4-F$_2$ | 4.21 (s) |
| XIX-15 | H | CH$_3$ | H | 2,5-F$_2$ | 4.21 (s) |
| XIX-16 | H | CH$_3$ | H | 3-Cl,4-F | 4.22 (s) |
| XIX-17 | H | CH$_3$ | H | 2-CF$_3$ | 4.18 (s) |
| XIX-18 | H | CH$_3$ | H | 3-CF$_3$ | 4.24 (s) |
| XIX-19 | H | CH$_3$ | H | 4-CF$_3$ | 4.24 (s) |
| XIX-20 | H | CH$_3$ | H | 2-OCH$_3$ | 4.18 (s) |
| XIX-21 | H | CH$_3$ | H | 3-OCH$_3$ | 4.21 (s) |
| XIX-22 | H | CH$_3$ | H | 4-OCH$_3$ | 4.20 (s) |
| XIX-23 | H | CH$_3$ | H | 3-SO$_2$C$_2$H$_5$ | 4.25 (s) |
| XIX-24 | H | CH$_3$ | H | 4-SO$_2$C$_2$H$_5$ | 4.25 (s) |
| XIX-25 | H | CH$_3$ | H | 3-NO$_2$ | 4.26 (s) |
| XIX-26 | H | CH$_3$ | H | 4-OCF$_3$ | 4.16 (s) |
| XIX-27 | H | CH$_3$ | H | 4-OPh | 4.22 (s) |
| XIX-28 | H | CH$_3$ | H | 4-SCH$_3$ | 4.21 (s) |
| XIX-29 | H | CH$_3$ | H | 4-i-C$_3$H$_7$ | 4.21 (s) |
| XIX-30 | H | CH$_3$ | H | 3,5-(CF$_3$)$_2$ | 4.27 (s) |
| XIX-31 | CH$_3$ | CH$_3$ | CH$_3$ | 4-F | 4.26 (s) |
| XIX-32 | H | CH$_3$ | CH$_3$ | 4-Cl | 4.14 (s) |
| XIX-33 | CH$_3$ | CH$_3$ | H | 4-F | 4.31 (s) |
| XIX-34 | CH$_3$ | CH$_3$ | H | 4-Cl | 4.31 (s) |
| XIX-35 | CH$_3$ | CH$_3$ | CH$_3$ | 4-Cl | 4.26 (s) |
| XIX-36 | H | Cl | H | 4-F | 4.35 (s) |
| XIX-37 | H | Cl | H | 4-Cl | 4.34 (s) |
| XIX-38 | H | Cl | H | 4-CF$_3$ | 4.37 (s) |
| XIX-39 | H | Cl | H | 2,4-Cl$_2$ | 4.34 (s) |
| XIX-40 | H | Cl | H | 3,4-Cl$_2$ | 4.36 (s) |
| XIX-41 | H | Cl | H | 3,5-Cl$_2$ | 4.36 (s) |
| XIX-42 | H | Cl | H | 2,4-F$_2$ | 4.35 (s) |
| XIX-43 | H | Cl | H | 3-Cl,4-F | 4.36 (s) |
| XIX-44 | H | Cl | H | 2,5-Cl$_2$ | 4.35 (s) |

Example (XX-1)

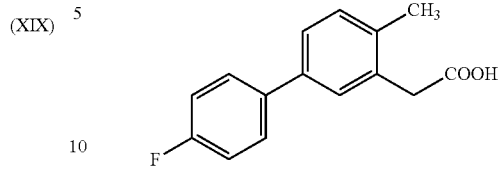

2 g (7.75 mmol) of the compound of Example (XXI-6) are dissolved in 20 ml of methanol and, at room temperature, a solution of 0.46 g (11.6 mmol) of NaOH in 20 ml of water is added. The mixture is stirred at room temperature for 12 h, the methanol is removed under reduced pressure and the residue is taken up in 100 ml of water. The alkaline solution is extracted 3× with methylene chloride and then acidified with 2N hydrochloric acid. The acidic solution is extracted 3× with methylene chloride and the organic phase is dried over sodium sulphate, filtered and concentrated under reduced pressure. The residue is triturated with petroleum ether and filtered off with suction.

Yield: 1.8 g (95% of theory); colourless solid; m.p. 107° C.

The following compounds of the formula (XX) are obtained analogously to Example (XX-1)

(XX)

| Ex. No. | W | X | Y | $V^1/V^2$ | m.p. (° C.) |
|---|---|---|---|---|---|
| XX-2 | H | CH$_3$ | H | 2-Cl | 123 |
| XX-3 | H | CH$_3$ | H | 3-Cl | 136 |
| XX-4 | H | CH$_3$ | H | 2-F | 92 |
| XX-5 | H | CH$_3$ | H | 3-F | 114 |
| XX-1 | H | CH$_3$ | H | 4-F | 107 |
| XX-6 | H | CH$_3$ | H | 2-CH$_3$ | 93 |
| XX-7 | H | CH$_3$ | H | 3-CH$_3$ | 105 |
| XX-8 | H | CH$_3$ | H | 4-CH$_3$ | 123 |
| XX-9 | H | CH$_3$ | H | 2,3-Cl$_2$ | 158 |
| XX-10 | H | CH$_3$ | H | 2,4-Cl$_2$ | 104 |
| XX-11 | H | CH$_3$ | H | 2,5-Cl$_2$ | 147 |
| XX-12 | H | CH$_3$ | H | 3,4-Cl$_2$ | 142 |
| XX-13 | H | CH$_3$ | H | 3,5-Cl$_2$ | 175 |
| XX-14 | H | CH$_3$ | H | 2,4-F$_2$ | 113 |
| XX-15 | H | CH$_3$ | H | 2,5-F$_2$ | 133 |
| XX-16 | H | CH$_3$ | H | 3-Cl,4-F | 191 |
| XX-17 | H | CH$_3$ | H | 2-CF$_3$ | 123 |
| XX-18 | H | CH$_3$ | H | 3-CF$_3$ | 135 |
| XX-19 | H | CH$_3$ | H | 4-CF$_3$ | 151 |
| XX-20 | H | CH$_3$ | H | 2-OCH$_3$ | 88 |
| XX-21 | H | CH$_3$ | H | 3-OCH$_3$ | 108 |
| XX-22 | H | CH$_3$ | H | 4-OCH$_3$ | 118 |
| XX-23 | H | CH$_3$ | H | 3-SO$_2$C$_2$H$_5$ | 142 |
| XX-24 | H | CH$_3$ | H | 4-SO$_2$C$_2$H$_5$ | 154 |
| XX-25 | H | CH$_3$ | H | 3-NO$_2$ | 185 |
| XX-26 | H | CH$_3$ | H | 4-OCF$_3$ | 96 |
| XX-27 | H | CH$_3$ | H | 4-OPh | 119 |
| XX-28 | H | CH$_3$ | H | 4-SCH$_3$ | 161 |
| XX-29 | H | CH$_3$ | H | 4-i-C$_3$H$_7$ | 111 |
| XX-30 | H | CH$_3$ | H | 3,5-(CF$_3$)$_2$ | 135 |
| XX-31 | CH$_3$ | CH$_3$ | CH$_3$ | 4-F | 143 |

-continued

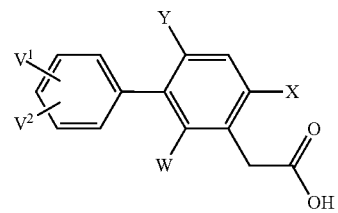

(XX)

| Ex. No. | W | X | Y | V¹/V² | m.p. (° C.) |
|---|---|---|---|---|---|
| XX-32 | H | $CH_3$ | $CH_3$ | 4-Cl | 133 |
| XX-33 | $CH_3$ | $CH_3$ | H | 4-F | 158 |
| XX-34 | $CH_3$ | $CH_3$ | H | 4-Cl | 160 |
| XX-35 | H | Cl | H | 4-F | 140 |
| XX-36 | H | Cl | H | 4-Cl | 124 |
| XX-37 | H | Cl | H | 4-$CF_3$ | 154 |
| XX-38 | H | Cl | H | 2,4-$Cl_2$ | 110 |
| XX-39 | H | Cl | H | 3,4-$Cl_2$ | 182 |
| XX-40 | H | Cl | H | 3,5-$Cl_2$ | 154 |
| XX-41 | H | Cl | H | 2,4-$F_2$ | 145 |
| XX-42 | H | Cl | H | 3-Cl, 4-F | 228 |
| XX-43 | H | Cl | H | 2,5-$Cl_2$ | 171 |
| XX-44 | $CH_3$ | $CH_3$ | $CH_3$ | 4-Cl | 165 |

Example (XXI-1)

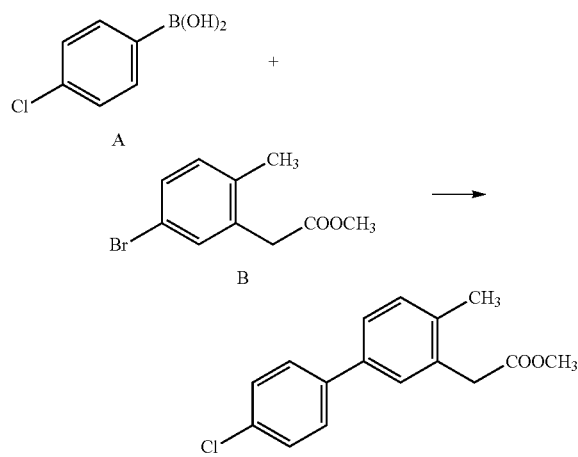

14.8 g (61 mmol) of B are initially charged in 70 ml of dimethoxyethane, and, at room temperature, 56 ml of a 1 molar solution of sodium carbonate, A (12.4 g; 80 mmol) and catalytic amounts of bis(triphenylphosphine)palladium(II) chloride are added successively under argon. The mixture is heated at 80° C. for 12 h and then cooled to room temperature, 150 ml of water are added and the mixture is extracted 3× with ethyl acetate. The organic phase is dried over sodium sulphate and filtered and the solvent is removed under reduced pressure.

Yield: 16.7 g (quantitative); yellow-brown oil which is used for further syntheses without further purification.

The following compounds of the formula (XXI) where $R^8=CH_3$ are obtained analogously to Example (XX-1)

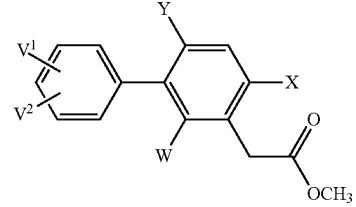

(XXI)

| Ex. No. | W | X | Y | V¹/V² | m.p. (° C.) |
|---|---|---|---|---|---|
| XXI-2 | H | $CH_3$ | H | 2-Cl | oil |
| XXI-3 | H | $CH_3$ | H | 3-Cl | oil |
| XXI-4 | H | $CH_3$ | H | 2-F | oil |
| XXI-5 | H | $CH_3$ | H | 3-F | oil |
| XXI-6 | H | $CH_3$ | H | 4-F | oil |
| XXI-7 | H | $CH_3$ | H | 2-$CH_3$ | oil |
| XXI-8 | H | $CH_3$ | H | 3-$CH_3$ | oil |
| XXI-9 | H | $CH_3$ | H | 4-$CH_3$ | oil |
| XXI-10 | H | $CH_3$ | H | 2,3-$Cl_2$ | oil |
| XXI-11 | H | $CH_3$ | H | 2,4-$Cl_2$ | oil |
| XXI-12 | H | $CH_3$ | H | 2,5-$Cl_2$ | oil |
| XXI-13 | H | $CH_3$ | H | 3,4-$Cl_2$ | oil |
| XXI-14 | H | $CH_3$ | H | 3,5-$Cl_2$ | oil |
| XXI-15 | H | $CH_3$ | H | 2,4-$F_2$ | oil |
| XXI-16 | H | $CH_3$ | H | 2,5-$F_2$ | oil |
| XXI-17 | H | $CH_3$ | H | 3-Cl,4-F | oil |
| XXI-18 | H | $CH_3$ | H | 2-$CF_2$ | oil |
| XXI-19 | H | $CH_3$ | H | 3-$CF_3$ | oil |
| XXI-20 | H | $CH_3$ | H | 4-$CF_3$ | oil |
| XXI-21 | H | $CH_3$ | H | 2-$OCH_3$ | oil |
| XXI-22 | H | $CH_3$ | H | 3-$OCH_3$ | oil |
| XXI-23 | H | $CH_3$ | H | 4-$OCH_3$ | 64 |
| XXI-24 | H | $CH_3$ | H | 3-$SO_2C_2H_5$ | oil |
| XXI-25 | H | $CH_3$ | H | 4-$SO_2C_2H_5$ | 89 |
| XXI-26 | H | $CH_3$ | H | 3-$NO_2$ | oil |
| XXI-27 | H | $CH_3$ | H | 4-$OCF_3$ | oil |
| XXI-28 | H | $CH_3$ | H | 4-OPh | oil |
| XXI-29 | H | $CH_3$ | H | 4-$SCH_3$ | 92 |
| XXI-30 | H | $CH_3$ | H | 4-i-$C_3H_7$ | oil |
| XXI-31 | H | $CH_3$ | H | 3,5-$(CF_3)_2$ | 63 |
| XXI-32 | $CH_3$ | $CH_3$ | $CH_3$ | 4-F | oil |
| XXI-33 | H | Cl | H | 4-F | oil |
| XXI-34 | H | Cl | H | 4-$CF_3$ | oil |
| XXI-35 | H | $CH_3$ | $CH_3$ | 4-Cl | oil |
| XXI-36 | $CH_3$ | $CH_3$ | H | 4-F | oil |
| XXI-37 | $CH_3$ | $CH_3$ | H | 4-Cl | oil |
| XXI-38 | $CH_3$ | $CH_3$ | $CH_3$ | 4-Cl | oil |
| XXI-39 | H | Cl | H | 4-Cl | oil |
| XXI-40 | H | Cl | H | 2,4-$Cl_2$ | oil |
| XXI-41 | H | Cl | H | 3,4-$Cl_2$ | oil |
| XXI-42 | H | Cl | H | 3,5-$Cl_2$ | oil |
| XXI-43 | H | Cl | H | 2,4-$F_2$ | oil |
| XXI-44 | H | Cl | H | 3-Cl-4-F | oil |
| XXI-45 | H | Cl | H | 2,5-$Cl_2$ | oil |

Use Examples

Example A

*Phaedon* Test (Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after they have dried, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compound of the Preparation Examples is highly effective:

TABLE A

| Active compounds | plant-damaging insects *Phaedon* test | |
|---|---|---|
| | Concentration of active compound in g/ha | Kill rate in % after $7^d$ |
| Ex. I-1-a-4 | 500 | 100 |

Example B

*Spodoptera frugiperda* Test (Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after they have dried, populated with caterpillars of the army worm (*Spodoptera frugiperda*).

After the desired period of time, the activity in % is determined. 100% means that all caterpillars have been killed; 0% means that none of the caterpillars have been killed.

In this test, for example, the following compounds of the Preparation Examples are highly effective:

TABLE B

| Active compounds | plant-damaging insects *Spodoptera frugiperda* test | |
|---|---|---|
| | Concentration of active compound in g/ha | Kill rate in % after $7^d$ |
| Ex. I-1-b-4 | 500 | 100 |
| Ex. I-1-c-4 | 500 | 100 |

Example C

*Meloidogyne* Test

| Solvent: | 7 parts by weight of dimethylformamide |

To produce a suitable preparation of active compound, 1 part by weight of active compound is mixed with the stated amounts of solvent, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal effect is determined in % by the formation of galls. 100% means that no galls have been found; 0% means that the number of galls on the treated plants corresponds to that of the untreated control.

In this test, for example, the following compounds of the Preparation Examples are highly effective:

TABLE C

| Active compounds | plant-damaging nematodes Meloidogyne test | |
|---|---|---|
| | Concentration of active compound in ppm | Effect in % after $14^d$ |
| Ex. I-1-a-1 | 20 | 80 |
| Ex. I-1-b-1 | 20 | 90 |
| Ex. I-2-c-6 | 20 | 90 |

Example D

*Myzus* Test (Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensi*), which are infested by all stages of the green peach aphid (*Myzus persicae*) are sprayed with a preparation of active compound of the desired concentration.

After the desired period of time, the activity in % is determined. 100% means that all aphids have been killed; 0% means that none of the aphids have been killed.

In this test, for example, the following compounds of the Preparation Examples are highly effective:

TABLE D

| Active compounds | plant-damaging insects *Myzus* test | |
|---|---|---|
| | Concentration of active compound in g/ha | Kill rate in % after $5^d$ |
| Ex. I-2-c-6 | 100 | 100 |
| Ex. I-1-c-1 | 100 | 100 |
| Ex. I-1-b-33 | 100 | 100 |
| Ex. I-2-a-32 | 500 | 90 |
| Ex. I-1-b-11 | 500 | 100 |
| Ex. I-1-c-15 | 500 | 100 |
| Ex. I-1-b-14 | 500 | 100 |
| Ex. I-2-b-15 | 500 | 100 |
| Ex. I-2-c-16 | 500 | 100 |
| Ex. I-1-b-17 | 500 | 90 |
| Ex. I-2-b-21 | 500 | 100 |
| Ex. I-1-b-26 | 500 | 100 |
| Ex. I-2-b-13 | 500 | 100 |
| Ex. I-1-b-30 | 500 | 100 |

TABLE D-continued

| | plant-damaging insects Myzus test | |
|---|---|---|
| Active compounds | Concentration of active compound in g/ha | Kill rate in % after $5^d$ |
| Ex. I-2-b-31 | 500 | 100 |
| Ex. I-2-b-30 | 500 | 100 |

Example E

*Phaedon* Test (Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after they have dried, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compounds of the Preparation Examples are highly effective:

TABLE E

| | plant-damaging insects Phaedon test | |
|---|---|---|
| Active compounds | Concentration of active compound in g/ha | Kill rate in % after $7^d$ |
| Ex. I-1-b-1 | 500 | 100 |
| Ex. I-1-c-1 | 100 | 100 |
| Ex. I-1-a-13 | 500 | 100 |
| Ex. I-2-a-13 | 500 | 100 |
| Ex. I-1-b-4 | 500 | 100 |
| Ex. I-1-b-13 | 500 | 100 |
| Ex. I-1-c-15 | 500 | 100 |
| Ex. I-2-c-4 | 500 | 100 |
| Ex. I-2-c-7 | 500 | 100 |
| Ex. I-1-c-9 | 500 | 100 |
| Ex. I-1-c-14 | 500 | 100 |
| Ex. I-1-b-16 | 500 | 100 |
| Ex. I-2-c-12 | 500 | 100 |
| Ex. I-2-c-9 | 500 | 100 |
| Ex. I-2-c-11 | 500 | 100 |
| Ex. I-1-b-27 | 500 | 100 |
| Ex. I-2-a-26 | 500 | 100 |
| Ex. I-2-c-14 | 500 | 100 |
| Ex. I-2-c-15 | 500 | 100 |
| Ex. I-2-b-17 | 500 | 100 |
| Ex. I-2-c-17 | 500 | 100 |
| Ex. I-2-b-19 | 500 | 100 |
| Ex. I-2-c-19 | 500 | 100 |
| Ex. I-2-b-32 | 500 | 100 |

Example F

*Spodoptera frugiperda* Test (Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after they have dried, populated with caterpillars of the army worm (*Spodoptera frugiperda*).

After the desired period of time, the activity in % is determined. 100% means that all caterpillars have been killed; 0% means that none of the caterpillars have been killed.

In this test, for example, the following compounds of the Preparation Examples are highly effective:

TABLE F

| | plant-damaging insects Spodoptera frugiperda test | |
|---|---|---|
| Active compounds | Concentration of active compound in g/ha | Kill rate in % after $7^d$ |
| Ex. I-2-a-6 | 500 | 100 |
| Ex. I-1-b-11 | 500 | 100 |
| Ex. I-1-c-13 | 500 | 83 |
| Ex. I-1-b-15 | 500 | 100 |
| Ex. I-2-b-3 | 500 | 83 |
| Ex. I-2-c-3 | 500 | 100 |
| Ex. I-2-b-5 | 500 | 100 |
| Ex. I-2-c-5 | 500 | 100 |
| Ex. I-2-b-15 | 500 | 100 |
| Ex. I-1-b-17 | 500 | 100 |
| Ex. I-1-c-17 | 500 | 83 |
| Ex. I-2-b-20 | 500 | 100 |
| Ex. I-2-c-20 | 500 | 100 |
| Ex. I-1-c-18 | 500 | 100 |
| Ex. I-2-b-2 | 500 | 100 |
| Ex. I-2-c-2 | 500 | 83 |
| Ex. I-2-c-13 | 500 | 100 |
| Ex. I-1-b-32 | 100 | 100 |

Example G

*Tetranychus* Test (OP-Resistant/Spray Treatment)

| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with a preparation of active compound of the desired concentration.

After the desired period of time, the activity in % is determined. 100% means that all spider mites have been killed; 0% means that none of the spider mites have been killed.

In this test, for example, the following compounds of the Preparation Examples are highly effective:

TABLE G plant-damaging mites
Tetranychus test (OP-resistant/spray treatment)

| Active compounds | Concentration of active compound in g/ha | Kill rate in % after $5^d$ |
|---|---|---|
| Ex. I-2-b-6 | 100 | 90 |
| Ex. I-1-a-10 | 500 | 90 |
| Ex. I-3-a-1 | 100 | 90 |
| Ex. I-1-a-11 | 500 | 100 |
| Ex. I-1-b-4 | 500 | 100 |
| Ex. I-1-c-7 | 500 | 100 |
| Ex. I-1-c-11 | 500 | 100 |
| Ex. I-1-c-12 | 500 | 100 |
| Ex. I-1-c-15 | 500 | 100 |
| Ex. I-2-c-23 | 500 | 100 |
| Ex. I-1-b-9 | 500 | 100 |
| Ex. I-1-c-16 | 500 | 100 |
| Ex. I-2-b-10 | 500 | 100 |
| Ex. I-2-c-10 | 500 | 100 |
| Ex. I-1-b-28 | 500 | 100 |
| Ex. I-1-a-17 | 500 | 90 |
| Ex. I-2-a-2 | 500 | 90 |
| Ex. I-1-c-17 | 500 | 100 |
| Ex. I-1-b-10 | 500 | 90 |
| Ex. I-2-c-26 | 100 | 90 |
| Ex. I-3-b-1 | 500 | 90 |
| Ex. I-1-b-34 | 500 | 90 |

Example H

*Sphaerotheca* Test (Cucumber)/Protective

| Solvent: | 49 parts by weight of N,N-dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated application rate. 1 day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% means that no infection is observed.

TABLE H

*Sphaerotheca* test (cucumber)/protective

| Active compounds | Application rate of active compound in g/ha | Efficacy in % |
|---|---|---|
| Ex. I-1-b-1 | 750 | 94 |
| Ex. I-1-b-3 | 750 | 90 |
| Ex. I-1-c-1 | 750 | 80 |

Example I

In vitro test for the $ED_{50}$ determination in microorganisms

A methanolic solution of the active compound to be tested, admixed with emulsifier PS16, is pipetted into the wells of microtiter plates. After the solvent has evaporated, 200 µl of potato/dextrose medium are added to each well.

Beforehand, a suitable concentration of spores or mycelium of the fungus to be tested was added to the medium.

The resulting concentrations of the active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes 50% inhibition of fungal growth compared to the untreated control ($ED_{50}$) is calculated from the data measured at different concentrations.

TABLE I

In vitro test for the $ED_{50}$ determination in microorganisms

| Active compounds | Microorganism | $ED_{50}$ value |
|---|---|---|
| Ex. I-2-b-6 | *Phytophthora cryptogea* | 0.56 |
| Ex. I-2-c-6 | *Phytophthora cryptogea* | 1.04 |
| Ex. I-1-c-1 | *Phytophthora cryptogea* | 0.71 |

Example J

Herbicidal Post-Emergence Action

Seeds of monocotyledonous and dicotyledonous weed and crop plants are placed into sandy loam in woodfibre pots, covered with soil and cultivated in a greenhouse under good growth conditions. 2-3 weeks after sowing, the test plants are treated at the one-leaf stage. The test compounds formulated as wettable powders (WP) are, in various dosages with a water application rate of 600 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=plants have died, 0% effect=like control plants).

| Greenhouse | | g a.i./ha | *Avena fatua* | *Lolium* | *Setaria* |
|---|---|---|---|---|---|
| Ex. I-1-c-1 | post-emergence | 320 | 90 | 90 | 80 |
| Ex. I-1-b-20 | post-emergence | 320 | 80 | 80 | 90 |
| Ex. I-1-a-12 | post-emergence | 320 | 80 | 70 | 70 |
| Ex. I-1-c-19 | post-emergence | 320 | 70 | 80 | 100 |

| Greenhouse | | g a.i./ha | *Lolium* | *Setaria* | *Amaranthus* |
|---|---|---|---|---|---|
| Ex. I-1-a-22 | post-emergence | 320 | 100 | 90 | 70 |

Example K

Critical Concentration Test/Soil Insects—Treatment of Transgenic Plants

| Test insect: | *Diabrotica balteata* - larvae in soil |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example L

*Heliothis virescens* Test—Treatment of Transgenic Plants

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soyabean shoots (*Glycine max*) of the cultivar Roundup Ready (trademark of Monsanto Comp. USA) are treated by being dipped into the preparation of active compound of the desired concentration and are populated with the tobacco bud worm *Heliothis virescens* while the leaves are still moist.

After the desired period of time, the kill of the insects is determined.

The invention claimed is:

1. A method for controlling animal pests comprising allowing a compound of formula (I)

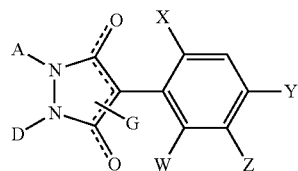

(I)

in which

X represents halogen, alkyl, alkoxy, alkenyloxy, alkylthio, alkylsulphinyl, alkylsulphonyl, haloalkyl, haloalkoxy, haloalkenyloxy, nitro, cyano, Z represents in each case optionally substituted aryl or hetaryl, W and Y independently of one another represent hydrogen, halogen, alkyl, alkoxy, alkenyloxy, haloalkyl, haloalkoxy, haloalkenyloxy, nitro or cyano, A represents in each case optionally halogen-substituted alkyl, alkenyl, alkoxyalkyl, saturated, optionally substituted cycloalkyl, D represents hydrogen or represents in each case optionally halogen-substituted alkyl, alkenyl or alkoxyalkyl, A and D together with the atoms to which they are attached represent a saturated or unsaturated 6- or 7-membered ring which optionally contains at least one further heteroatom and which is unsubstituted or substituted in the A, D moiety or represent an optionally substituted 5-membered ring, G represents hydrogen (a) or represents one of the groups

(b)

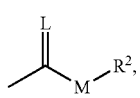
(c)

(d)

(e)

E, or
(f)

(g)

in which

E represents a metal ion or an ammonium,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, represents in each case optionally substituted phenyl, phenylalkyl, hetaryl, phenoxyalkyl or hetaryloxyalkyl, $R^2$ represents in each case optionally halogen-substituted alkyl, alkenyl or represents in each case optionally substituted cycloalkyl, phenyl or benzyl, $R^3$, $R^4$, and $R^5$ independently of one another represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl or together with the N atom to which they are attached represent a ring which is optionally interrupted by oxygen or sulphur, to act on said animal pests and/or a habitat thereof.

2. The method according to claim 1 wherein

X represents halogen, $C_1$-$C_6$-alkyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-halo-alkoxy, $C_3$-$C_6$-haloalkenyloxy, nitro or cyano, W and Y independently of one another represent hydrogen, halogen, $C_1$-$C_6$-alkyl, $C_1$-$C_6$-haloalkyl, $C_1$-$C_6$-alkoxy, $C_1$-$C_6$-haloalkoxy, nitro or cyano, Z represents one of the radicals

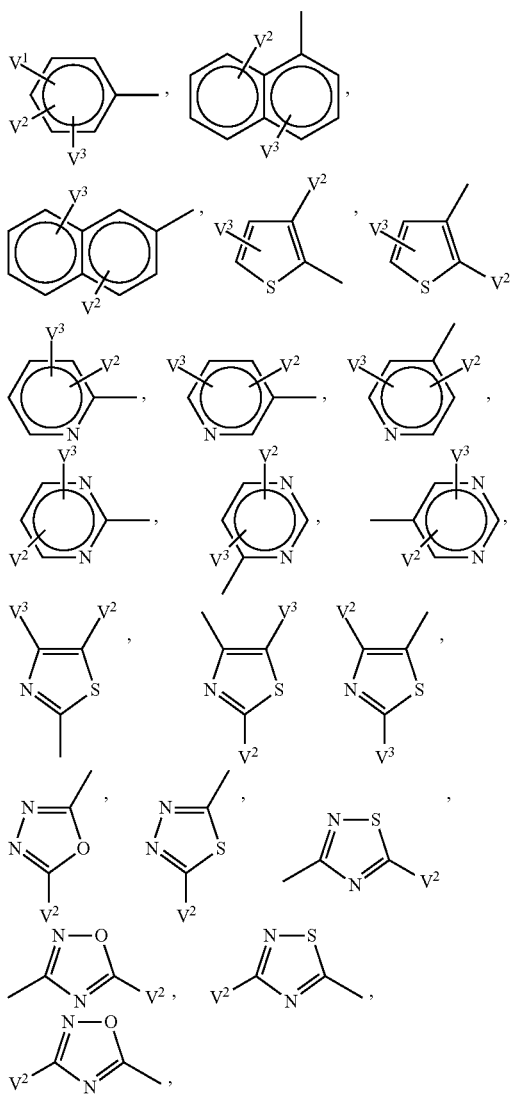

$V^1$ represents halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy, A represents in each case optionally halogen-substituted $C_1$-$C_8$-alkyl, $C_3$-$C_8$-alkenyl or optionally $C_1$-$C_4$-alkyl-, halogen- or $C_1$-$C_4$-alkoxy-substituted $C_3$-$C_6$-cycloalkyl, D represents hydrogen, represents in each case halogen-substituted $C_1$-$C_8$-alkyl or $C_3$-$C_8$-alkenyl, A and D together represent in each case optionally substituted $C_4$-$C_6$-alkanediyl or $C_4$-$C_6$-alkenediyl in which optionally one methylene group may be replaced by oxygen or sulphur, wherein possible substituents are in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl, benzyloxy or a further $C_1$-$C_6$-alkanediyl grouping, or which optionally contains one of the following groups

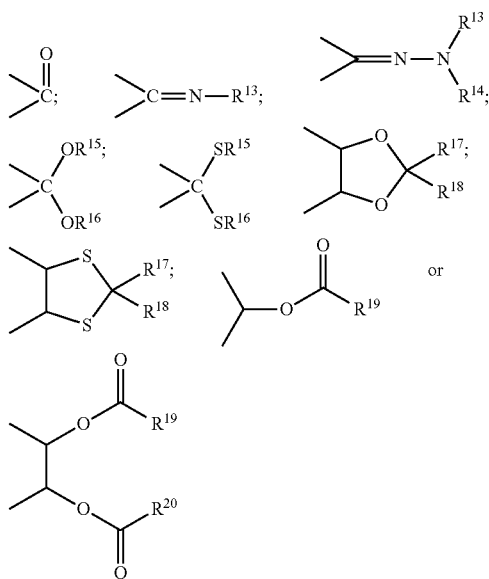

or represents $C_3$-alkanediyl which is optionally mono- to trisubstituted by halogen, $C_1$-$C_6$-alkyl, $C_1$-$C_4$-haloalkyl or $C_1$-$C_6$-alkoxy, G represents hydrogen (a) or represents one of the groups

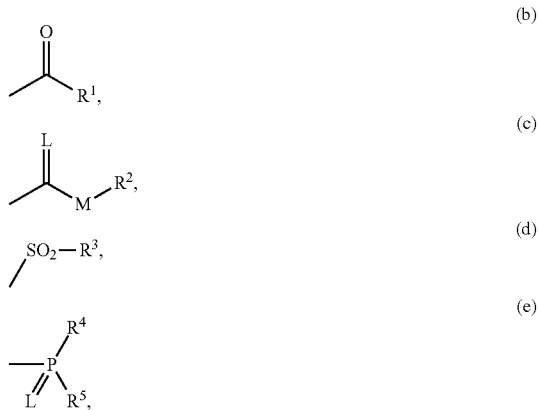

-continued

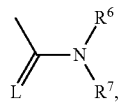

(f)

(g)

in which

E represents a metal ion or an ammonium ion,

L represents oxygen or sulphur and

M represents oxygen or sulphur, $R^1$ represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen, $C_1$-$C_6$-alkyl or $C_1$-$C_6$-alkoxy-substituted $C_3$-$C_8$-cycloalkyl in which optionally one or more not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl, represents optionally halogen- or $C_1$-$C_6$-alkyl-substituted phenoxy-$C_1$-$C_6$-alkyl or represents in each case optionally halogen-, amino- or $C_1$-$C_6$-alkyl-substituted 5- or 6-membered hetaryloxy-$C_1$-$C_6$-alkyl, $R^2$ represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)-amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl substituted phenyl, phenoxy or phenylthio, $R^6$ and $R^7$ independently of one another represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, represent optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one methylene group is replaced by oxygen or sulphur, $R^{13}$ represents hydrogen, represents in each case optionally halogen-substituted $C_1$-$C_8$-alkyl or $C_1$-$C_8$-alkoxy, represents optionally halogen-, $C_1$-$C_4$-alkyl- or $C_1$-$C_4$-alkoxy-substituted $C_3$-$C_8$-cycloalkyl in which optionally one methylene group is replaced by oxygen or sulphur, or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, phenyl-$C_1$-$C_4$-alkyl or phenyl-$C_1$-$C_4$-alkoxy, $R^{14}$ represents hydrogen or $C_1$-$C_8$-alkyl or $R^{13}$ and $R^{14}$ together represent $C_4$-$C_6$-alkanediyl, $R^{15}$ and $R^{16}$ are identical or different and represent $C_1$-$C_6$-alkyl or $R^{15}$ and $R^{16}$ together represent a $C_2$-$C_4$-alkanediyl radical which is optionally substituted by $C_1$-$C_6$-alkyl, $C_1$-$C_6$-haloalkyl or by optionally halogen-, $C_1$-$C_6$-alkyl-, $C_1$-$C_4$-haloalkyl-, $C_1$-$C_6$-alkoxy-, $C_1$-$C_4$-haloalkoxy-, nitro- or cyano-substituted phenyl, $R^{17}$ and $R^{18}$ independently of one another represent hydrogen, represent optionally halogen-substituted $C_1$-$C_8$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl or $R^{17}$ and $R^{18}$ together with the carbon atom to which they are attached represent a carbonyl group or represent optionally halogen-, $C_1$-$C_4$-alkyl- or $C_1$-$C_4$-alkoxy-substituted $C_5$-$C_7$-cycloalkyl in which optionally one methylene group is replaced by oxygen or sulphur, $R^{19}$ and $R^{20}$ independently of one another represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)-amino or di-($C_3$-$C_{10}$-alkenyl)amino.

3. The method according to claim 1 wherein

W represents hydrogen, fluorine, chlorine, bromine, methyl, ethyl, methoxy or ethoxy, X represents fluorine, chlorine, bromine, $C_1$-$C_4$-alkyl, $C_1$-$C_4$-alkoxy, $C_3$-$C_4$-alkenyloxy, $C_1$-$C_4$-haloalkyl, $C_1$-$C_4$-haloalkoxy, $C_3$-$C_4$-haloalkenyloxy, nitro or cyano, Y represents hydrogen, fluorine, chlorine, bromine, $C_1$-$C_4$-alkyl, $C_1$-$C_2$-haloalkyl, $C_1$-$C_4$-alkoxy or $C_1$-$C_2$-haloalkoxy, Z represents one of the radicals

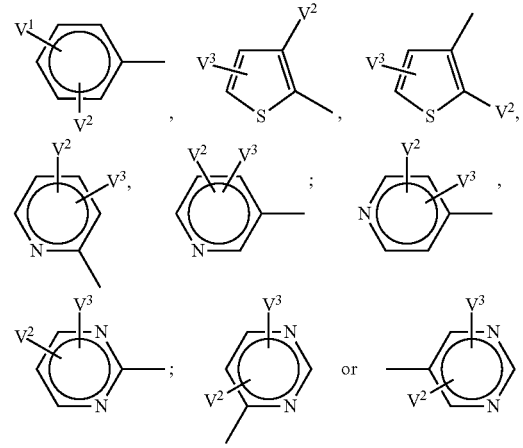

$V^1$ represents fluorine, chlorine, bromine, $C_1$-$C_6$-alkyl, $C_1$-$C_4$-alkoxy, $C_1$-$C_4$-alkylthio, $C_1$-$C_4$-alkylsulphonyl, $C_1$-$C_2$-haloalkyl, $C_1$-$C_2$-haloalkoxy, nitro, cyano or represents phenyl, phenoxy, phenoxy-$C_1$-$C_2$-alkyl, phenyl-$C_1$-$C_2$-alkoxy, phenylthio-$C_1$-$C_2$-alkyl or phenyl-$C_1$-$C_2$-alkylthio, each of which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A represents $C_1$-$C_6$-alkyl, $C_3$-$C_6$-alkenyl or $C_3$-$C_6$-cycloalkyl, D represents hydrogen, $C_1$-$C_6$-alkyl or $C_3$-$C_6$-alkenyl, A and D together represent optionally substituted $C_4$-$C_5$-alkanediyl in which optionally one methylene group may be replaced by a carbonyl group, oxygen or sulphur, possible substitutents being hydroxyl, $C_1$-$C_6$-alkyl, $C_1$-$C_4$-alkoxy or a further $C_1$-$C_4$-alkanediyl grouping, or which optionally contains one of the following groups

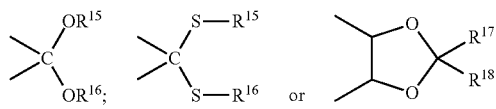

or represent $C_3$-alkanediyl which is optionally mono- or disubstituted by fluorine, chlorine, trifluoromethyl, methyl, ethyl or methoxy, G represents hydrogen (a) or represents one of the groups

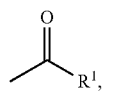 (b)

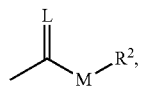 (c)

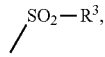 (d)

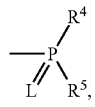 (e)

E, or (f)

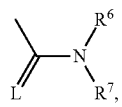 (g)

in which

E represents a metal ion or an ammonium ion,

L represents oxygen or sulphur and

M represents oxygen or sulphur, $R^1$ represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, represents $C_3$-$C_6$-cycloalkyl which is optionally monosubstituted by $C_1$-$C_2$-alkyl or $C_1$-$C_2$-alkoxy or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ represents $C_1$-$C_6$-alkyl which is optionally mono- to trisubstituted by fluorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine, or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ represents $C_1$-$C_6$-alkoxy or $C_1$-$C_6$-alkylthio, $R^6$ represents hydrogen, represents $C_1$-$C_6$-alkyl, $C_3$-$C_6$-cycloallyl, $C_1$-$C_6$-alkoxy, $C_3$-$C_6$-alkenyl, $C_1$-$C_6$-alkoxy-$C_1$-$C_4$-alkyl, each of which is optionally mono- to trisubstituted by fluorine, represents phenyl which is optionally mono- or disubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ represents $C_1$-$C_6$-alkyl, $C_3$-$C_6$-alkenyl or $C_1$-$C_6$-alkoxy-$C_1$-$C_4$-alkyl, $R^6$ and $R^7$ together represent a $C_4$-$C_5$-alkylene radical which is optionally mono- or disubstituted by methyl or ethyl and in which optionally one methylene group is replaced by oxygen or sulphur, $R^{15}$ and $R^{16}$ are identical and represent $C_1$-$C_4$-alkyl, $R^{15}$ and $R^{16}$ together represent a $C_2$-$C_3$-alkanediyl radical which is optionally mono- or disubstituted by methyl, ethyl, propyl or isopropyl, $R^{17}$ and $R^{18}$ independently of one another represent hydrogen, represent methyl, ethyl, propyl, isopropyl, butyl, isobutyl or tert-butyl, each of which is optionally mono- to trisubstituted by fluorine and/or chlorine or $R^{17}$ and $R^{18}$ together with the carbon to which they are attached represent a carbonyl group or represent optionally methyl-, ethyl-, methoxy- or ethoxy-substituted $C_5$-$C_6$-cycloalkyl in which optionally one methylene group is replaced by oxygen.

4. The method according to claim 1 wherein
W represents hydrogen, methyl, ethyl or chlorine,
X represents chlorine, methyl, ethyl, propyl, methoxy, ethoxy, propoxy or trifluoromethyl,
Y represents hydrogen, chlorine or methyl,
Z represents one of the radicals

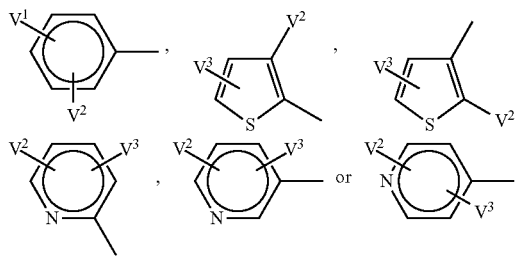

$V^1$ represents fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, $SO_2C_2H_5$, $SCH_3$, phenoxy, nitro or cyano,
$V^2$ and $V^3$ independently of one another represent hydrogen, fluorine, chlorine, methyl, methoxy or trifluoromethyl,
A represents methyl, ethyl, propyl or butyl,
D represents hydrogen, methyl or ethyl,
A and D together represent optionally substituted $C_4$-$C_5$-alkanediyl in which optionally one methylene group is replaced by oxygen or sulphur and which is optionally substituted by hydroxyl, methyl, ethyl, methoxy, ethoxy or by a further $C_1$-$C_4$-alkanediyl grouping or represent $C_3$-alkanediyl which is optionally mono- or disubstituted by fluorine, methyl, trifluoromethyl or methoxy,
G represents hydrogen (a) or represents one of the groups

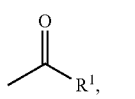 (b)

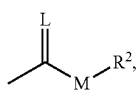 (c)

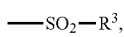 (d)

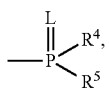 (e)

 (f)

E, or

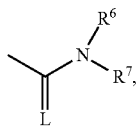 (g)

in which
E represents a metal ion equivalent or an ammonium ion,
L represents oxygen or sulphur and
M represents oxygen or sulphur, $R^1$ represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally mono- to trisubstituted by fluorine, or represents cyclopropyl or cyclohexyl, each of which is optionally monosubstituted by fluorine, chorine, methyl or methoxy,
represents phenyl which is optionally monosubstituted by fluorine, chlorine, bromine, cyano, nitro, methyl, methoxy, trifluoromethyl or trifluoromethoxy,
$R^2$ represents $C_1$-$C_8$-alkyl, $C_2$-$C_6$-alkenyl or $C_1$-$C_4$-alkoxy-$C_2$-$C_3$-alkyl, each of which is optionally monosubstituted by fluorine,
or represents phenyl or benzyl, each of which is optionally monosubstituted by fluorine, chlorine, cyano, nitro, methyl, ethyl, n-propyl, i-propyl, methoxy, ethoxy, trifluoromethyl or trifluoromethoxy,
$R^3$ represents methyl, ethyl, n-propyl, isopropyl, each of which is optionally mono- to trisubstituted by fluorine, or represents phenyl or benzyl, each of which is optionally monosubstituted by fluorine, chlorine, bromine, methyl, tert-butyl, methoxy, trifluoromethyl, trifluoromethoxy, cyano or nitro,
$R^4$ represents $C_1$-$C_4$-alkyl, $C_1$-$C_4$-alkoxy, $C_1$-$C_4$-alkyl amino, di-($C_1$-$C_4$-alkyl)amino, $C_1$-$C_4$-alkylthio, each of which is optionally mono- to trisubstituted by fluorine, or represents phenyl, phenoxy or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl,
$R^5$ represents methoxy, ethoxy, propoxy, butoxy, methylthio, ethylthio, propylthio or butylthio,
$R^6$ represents hydrogen, represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, each of which is optionally mono- to trisubstituted by fluorine, represents phenyl which is optionally monosubstituted by fluorine, chlorine, bromine, trifluoromethyl, methyl or methoxy, represents benzyl which is optionally monosubstituted by fluorine, chlorine, bromine, methyl, trifluoromethyl or methoxy,
$R^7$ represents methyl, ethyl, propyl, isopropyl, butyl, isobutyl or allyl,
$R^6$ and $R^7$ represent a $C_4$-$C_5$-alkylene radical in which optionally one methylene group is replaced by oxygen or sulphur.

5. The method according to claim 1 wherein
W represents hydrogen or methyl,
X represents chlorine or methyl,
Y represents hydrogen or methyl,
Z represents one of the radicals

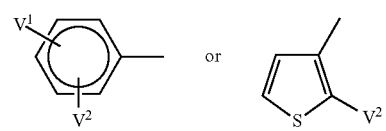

$V^1$ represents fluorine, chlorine, methyl, isopropyl, methoxy, trifluoromethyl, trifluoromethoxy, $SO_2C_2H_5$, $SCH_3$, phenoxy or nitro,
$V^2$ represents hydrogen, fluorine, chlorine or trifluoromethyl, A represents methyl or ethyl,
D represents methyl or ethyl,
A and D together represent optionally substituted $C_4$-$C_5$-alkanediyl in which optionally one methylene group is replaced by oxygen and which is optionally substituted by a further $C_1$-$C_2$-alkanediyl grouping, or represents $C_3$-alkanediyl which is optionally mono- or disubstituted by fluorine, methyl or trifluoromethyl,
G represents hydrogen (a) or represents one of the groups

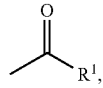
(b)

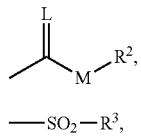
(c)

—$SO_2$—$R^3$, (d)

in which
L represents oxygen and
M represents oxygen,
$R^1$ represents $C_1$-$C_6$-alkyl or cyclopropyl,
$R^2$ represents $C_1$-$C_8$-alkyl or $C_1$-$C_4$-alkoxy-$C_2$-$C_3$-alkyl,
$R^3$ represents methyl, ethyl or isopropyl.

* * * * *